(12) United States Patent
Jordan et al.

(10) Patent No.: US 9,732,325 B2
(45) Date of Patent: Aug. 15, 2017

(54) MVA VIRUS AND USES THEREOF

(71) Applicant: Probiogen AG, Berlin (DE)

(72) Inventors: Ingo Jordan, Berlin (DE); Volker Sandig, Berlin (DE)

(73) Assignee: PROBIOGEN AG, Berlin (DE)

( * ) Notice: Subject to any disclaimer, the term of this patent is extended or adjusted under 35 U.S.C. 154(b) by 104 days.

(21) Appl. No.: 14/431,814

(22) PCT Filed: Sep. 28, 2012

(86) PCT No.: PCT/EP2012/069256
§ 371 (c)(1),
(2) Date: Mar. 27, 2015

(87) PCT Pub. No.: WO2014/048500
PCT Pub. Date: Apr. 3, 2014

(65) Prior Publication Data
US 2015/0299666 A1    Oct. 22, 2015

(51) Int. Cl.
*C12N 7/00*     (2006.01)
*C07K 14/005*   (2006.01)

(52) U.S. Cl.
CPC .............. *C12N 7/00* (2013.01); *C07K 14/005* (2013.01); *C12N 2710/24021* (2013.01); *C12N 2710/24022* (2013.01); *C12N 2710/24064* (2013.01); *C12N 2710/24121* (2013.01)

(58) Field of Classification Search
None
See application file for complete search history.

(56) References Cited

FOREIGN PATENT DOCUMENTS

WO    2005048957 A2    6/2005
WO    2006076003 A2    7/2006

OTHER PUBLICATIONS

Blasco et al. Dissociation of progeny vaccinia virus from the cell membrane is regulated by a viral envelope glycoprotein: effect of a point mutation in the lectin homology domain of the A34R gene. J Virol. Jun. 1993;67(6):3319-25.*
Husain et al., "Resistance of a vaccinia virus A34R deletion mutant to spontaneous rupture of the outer membrane of progeny virions on the surface of infected cells", Virology, 2007, vol. 366, pp. 424-432.
Jordan et al., "An avian cell designed for production of highly attenuated viruses", Vaccine, 2009, vol. 27, pp. 7448-7756.
Jordan et al., "A chemically defined production process for highly attenuated poxviruses", Biologicals, 2011, vol. 39, pp. 50-58.
European Examination Report, Application No. EP 12769398.4, dated Jan. 30, 2017.
Suter et al., "Modified vaccinia Ankara strains with identical coding sequences actually represent complex mixtures of viruses that determine the biological properties of each strain", Vaccine, 2009, pp. 7442-7450.

* cited by examiner

*Primary Examiner* — Michelle S Horning
(74) *Attorney, Agent, or Firm* — MacMillan, Sobanski & Todd, LLC

(57) ABSTRACT

The present invention relates to a novel Modified Vaccinia Ankara (MVA) virus. The present invention also relates to a method for culturing said MVA virus and to a method for producing said MVA virus. Further, the present invention relates to a pharmaceutical composition comprising said MVA virus and one or more pharmaceutical acceptable excipient(s), diluent(s), and/or carrier(s). Furthermore, the present invention relates to a vaccine comprising said MVA virus. In addition, the present invention relates to said MVA virus for use in medicine.

17 Claims, 11 Drawing Sheets

FIGURE 5

MVA VIRUS AND USES THEREOF

This application claims priority to PCT application No. PCT/EP2012/069256 filed Sep. 28, 2012, the disclosures of which are hereby incorporated by reference in their entirety.

The present invention relates to a novel Modified Vaccinia Ankara (MVA) virus. The present invention also relates to a method for culturing said MVA virus and to a method for producing said MVA virus. Further, the present invention relates to a pharmaceutical composition comprising said MVA virus and one or more pharmaceutical acceptable excipient(s), diluent(s), and/or carrier(s). Furthermore, the present invention relates to a vaccine comprising said MVA virus. In addition, the present invention relates to said MVA virus for use in medicine.

BACKGROUND OF THE INVENTION

Vaccines are one of the most efficacious human health interventions available and protect against a very broad spectrum of infectious diseases. However, protective or therapeutic immunity still can not be raised against a number of latent and chronic pathogens. Conventional approaches that mainly elicit antibody responses have not been successful. Reasons include that epitopes may be variable, frequently masked or protected by microbial decoys, or because the pathogen hides in a way not accessible to antibodies.

Compared to vaccination with inactivated virions or purified subunits, live vaccines induce a broad response that also involves the cellular compartment of the immune system. However, due to the increased numbers of immunocompromised individuals and expansion of international mobility, the use of replication-competent strains can be associated with risks such as reversion to more pathogenic forms (Zurbriggen et al. 2008 in Appl Environ Microbiol 74, 5608-5614) or are severe adverse events both in recipients and contact persons of vaccinees (Kemper et al. 2002 in Eff Clin Pract 5, 84-90; Parrino and Graham 2006 in J Allergy Clin Immunol 118, 1320-1326).

Modern vectored vaccines (Excler et al. 2010 in Biologicals 38, 511-521; Plotkin 2009 in Clin Vaccine Immunol 16, 1709-1719) combine the advantages of an attenuated infection with the strong safety profile inherent to host-restricted vectors that can not replicate in the human or animal recipient. Especially promising hyperattenuated vectors are host-restricted poxviruses including the Modified Vaccinia Ankara (MVA) virus. The hyperattenuated poxviruses have demonstrated safety in clinical trials (Cebere et al. 2006 in Vaccine 24, 417-425; Dorrell et al. 2007 in Vaccine 25, 3277-3283; Gilbert et al. 2006 in Vaccine 24, 4554-4561; Mayr 2003 in Comp Immunol Microbiol Infect Dis 26, 423-430; Webster et al. 2005 in Proc Natl Acad Sci USA 102, 4836-4841) and yet are efficient stimulators of the immune response (Drillien et al. 2004 in J Gen Virol 85, 2167-2175; Liu et al. 2008 in BMC Immunol 9, 15; Ryan et al. 2007 in Vaccine 25, 3380-3390; Sutter and Moss 1992 in Proc Natl Acad Sci USA 89, 10847-10851; Sutter et al. 1994 in Vaccine 12, 1032-1040). Particularly, the MVA virus is related to Vaccinia virus, a member of the genera Orthopoxvirus in the family of Poxviridae. The MVA virus has been generated by 516 serial passages on chicken embryo fibroblasts of the Chorioallantois Vaccinia Ankara (CVA) virus. In the course of the attenuation process by repeated passaging to chicken derived material as production substrate, the MVA virus has lost approximately 15% of the genomic DNA at multiple sites (Mayr and Munz 1964 in Zentralbl Bakteriol Orig 195, 24-35; Meyer et al. 1991 in J Gen Virol 72 (Pt 5), 1031-1038). The MVA virus has been analysed to determine alterations in the genome relative to the wild-type CVA strain. Six major deletions of genomic DNA (deletion I, II, III, IV, V, and VI), totalling 31.000 base pairs, have been identified (Meyer, et al. 1991 in J Gen Virol 72 (Pt 5), 1031-1038). It became severely host cell restricted to avian cells. Whereas parental vaccinia virus has a broad host range, the MVA virus has a very narrow host range. For example, MVA does not replicate in human and non-human primate cells. In the human HeLa cell line, the replication block appears to occur at a defined step in genome packaging (Sancho et al. 2002 in J Virol 76, 8318-8334). In addition, the cells lines HEK 293 and Vero are not a preferred production system. It was further shown in a variety of animal models that the resulting MVA virus was significantly avirulent (Mayr and Danner 1978 in Dev Biol Stand 41, 225-234). Additionally, the MVA strain has been tested in clinical trials as vaccine to immunize against the human smallpox disease (Mayr 2003 in Comp Immunol Microbiol Infect Dis 26, 423-430). These studies involved over 120.000 humans, including high risk patients, and proved that, compared to CVA, MVA had diminished virulence or infectiousness while it maintained good immunogenicity.

However, the provision of adequate supply of the MVA virus is challenging. On the one hand, the MVA virus has to be given at high doses because it replicates at very low levels or not at all in the recipient. On the other hand, the MVA virus production systems which are presently available are time-consuming and expensive and can not satisfy the needs of the pharmaceutical industry.

As mentioned above, research on and production of MVA depends on avian cells. Currently, vaccine strains adapted to avian hosts are produced only in embryonated chicken eggs or on fibroblasts prepared from such eggs. This technology is associated with further disadvantages including continuous flow of primary animal-derived material into a demanding clinical production process and costs for maintenance of SPF (specific pathogen free) donor flocks. Because time from collection of the embryonated eggs to production of the vaccine is short, testing for extraneous agents is performed on the final bulk (Philipp and Kolla 2010 in Biologicals 38, 350-351). Occasionally, complete vaccine lots have to be discarded when contamination is confirmed by quality testing (Enserink 2004 in Science 306, 385).

Recently, to facilitate industrial application and vaccine programs in developing or newly industrialized countries, the inventors of the present invention designed and generated a host cell line fully permissive for vaccine strains depending on avian substrates (Jordan et al. 2009 in Vaccine 27, 748-756). They also developed a highly efficient and fully scalable chemically-defined production process for these viruses (Jordan et al. 2011 in Biologicals 39, 50-58).

Here, for the first time and with the above technology at hand, the inventors characterized stable isolates of subsequent generations of an already adapted and hyperattenuated MVA virus on a cell substrate fully permissive for the same hyperattenuated virus under highly artificial conditions imposed by virus production in a chemically defined suspension culture. This is an unusual experiment and the result is surprising. As described in the Principles of Virology (ISBN-10: 1555814433), the motivation of serial passaging is generally to adapt viruses to substrates with initially low permissivity: "Less virulent (attenuated) viruses can be selected by growth in cells other than those of the normal host, or by propagation at non-physiological temperatures.

Mutants able to propagate better under these selective conditions arise during viral replication. When such mutants are isolated, purified, and subsequently tested for pathogenicity in appropriate models, some may be less pathogenic than their parent".

The above characterization resulted in the identification of novel MVA viruses with point mutations in structural proteins. This result is consistent with virus propagation under artificial culturing conditions rather than selection within a certain host cell. The novel MVA viruses show beneficial properties in a chemically defined suspension culture compared to known MVA virus strains such as an increased infectious activity and a greater number of infectious units in the extracellular space. Said beneficial properties improve the industrial production of said MVA viruses. Particularly, they allow the production of the novel MVA virus strains in high yields. In addition, the novel MVA virus strains can be isolated directly from the cell-free supernatant which facilitates purification and, thus, the logistic and the operation of bioreactors producing said MVA viruses. This, in turn, reduces the costs of MVA virus production.

SUMMARY OF THE INVENTION

In a first aspect, the present invention relates to a Modified Vaccinia Ankara (MVA) virus comprising a nucleic acid sequence encoding an A3L gene product and/or an A34R gene product, wherein said nucleic acid sequence comprises at least one mutation resulting in an amino acid sequence modification of said gene product(s).

In a second aspect, the present invention relates to a genome of the MVA virus according to the first aspect.

In a third aspect, the present invention relates to a cell comprising a MVA virus according to the first aspect or a genome according to the second aspect.

In a fourth aspect, the present invention relates to a method for culturing a MVA virus according the first aspect comprising the steps of:
(i) providing a cell according to the third aspect,
(ii) culturing the cell, and
(iii) isolating the MVA virus.

In a fifth aspect, the present invention relates to a method for producing a MVA virus according to the first aspect comprising the steps of:
(i) infecting a cell with a MVA virus,
(ii) culturing the cell,
(iii) isolating the MVA virus, and
(iv) repeating steps (i) to (iii) with the MVA virus isolated in step (iii) until a MVA virus comprising a nucleic acid sequence encoding an A3L gene product and/or an A34R gene product, wherein said nucleic acid sequence comprises at least one mutation resulting in an amino acid sequence modification of said gene product(s), is detected.

In a sixth aspect, the present invention relates to a pharmaceutical composition comprising a MVA virus according to the first aspect or a genome according to the second aspect and one or more pharmaceutical acceptable excipient(s), diluent(s), and/or carrier(s).

In a seventh aspect, the present invention relates to a vaccine comprising a MVA virus according to the first aspect or a genome according to the second aspect.

In an eighth aspect, the present invention relates to a MVA virus according to the first aspect or a genome according to the second aspect for use in medicine.

In a ninth aspect, the present invention relates to a MVA virus comprising a nucleic acid sequence, wherein the A3L gene and/or A9L gene is functionally deleted.

In a tenth aspect, the present invention relates to a cell comprising an A3L gene, A9L gene, and/or A34R gene of a MVA virus and expressing said gene(s).

In an eleventh aspect, the present invention relates to a nucleic acid molecule comprising an A3L gene, A9L gene, and/or A34R gene of a MVA virus, wherein said gene(s) is (are) operably linked to a heterologous nucleic acid sequence.

In a twelfth aspect, the present invention relates to a method for producing a recombinant MVA virus comprising the following steps:
(i) providing a cell,
(ii) introducing a MVA virus according to the ninth aspect and a nucleic acid molecule according to the eleventh aspect into the cell, and
(iii) cultivating the cell under conditions allowing homologous recombination between the nucleic acid sequence of the MVA virus and the nucleic acid molecule thereby obtaining the recombinant MVA virus.

This summary of the invention does not describe all features of the invention.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. As used in this specification and the appended claims, the singular forms "a", "an", and "the" include plural referents, unless the content clearly dictates otherwise.

The term "attenuated virus", as used herein, refers to a virus with compromised virulence in the intended recipient, e.g. human or animal recipient. Such a property can be achieved by adaptation of a virus to narrow temperature ranges or narrow host ranges and to other artificial replication environments, including chemically defined media. Replication of such a virus is restricted in cells derived from the intended recipient, e.g. human or animal recipient, or in cells removed from the tissue environment. It may replicate to high titers outside of the intended recipient (e.g. in a permissive cell culture or laboratory animal). An example of an attenuated virus strain is the Ender's attenuated measles virus Edmonston strain given to protect against serious measles disease or the vaccinia virus strain used in the pox eradication campaign of the World Health Organisation (WHO) in the 1970s.

The term "highly attenuated virus", as used herein, refers to a virus with blocked virulence in the intended recipient, e.g. human or animal recipient. Such a property can be achieved by adaptation of a virus to narrow temperature ranges or narrow host ranges and to other artificial replication environments, including chemically defined media. Replication of such a virus is blocked in cells derived from the intended recipient, e.g. human or animal recipient, or in cells removed from the tissue environment. It may replicate to high titers outside of the intended recipient (e.g. in a permissive cell/cell culture or laboratory animal). The MVA virus of the present invention is a highly attenuated virus. It does not replicate in human or non-human primate cells.

The term "host-restricted virus", as used herein, refers to a virus which (only or mainly) replicates in a specific host organism, e.g. in a cell such as an avian cell or in an animal such as a laboratory animal. It does not replicate or only replicates at very low levels in other organisms, e.g. in other cells than avian cells. A host-restricted virus may be achieved by "(serial) virus passaging" of a virus in a host organism, e.g. in avian cells. The MVA virus of the present invention is restricted to avian cells. It does not replicate in human cells.

The term "virus passaging", as used herein, refers to a process which involves infecting a series of host organisms, e.g. cells or animals such as laboratory animals, with a virus. Each time the virus is given some time to incubate, and then the next host organism is infected with the incubated virus. This process can also be designated as "serial virus passaging". For example, serial virus passaging allows the generation of (highly) attenuated and/or host-restricted viruses. The MVA virus of the present invention is a highly attenuated virus. It is restricted to avian cells. It does not replicate in human or non-human primate cells.

When a host organism, e.g. a cell such as an avian cell or an animal such as a laboratory animal, is defined by the term "permissive", it refers to the fact that the virus is able to circumvent defenses of said organism and is able to invade a cell, replicate in said cell, and escape from said cell. Usually this occurs when the virus has modulated one or several of the cellular intrinsic defenses of said organism and/or the immune system of said organism.

The term "recipient", as used herein, refers to a subject which may receive a virus, e.g. which may be vaccinated with a virus. The subject may be a human or an animal. Said animal may be a member of the mammalian species such as a canine, feline, lupine, mustela, rodent (e.g. a mouse, rat or hamster), an equine, a bovine, an ovine, a caprine, pig, bat (e.g. a megabat or microbat), or a non-human primate (e.g. a monkey such as a great ape). Particularly, the MVA virus of the present invention does not replicate in human or non-human primate recipients.

The term "host organism", as used herein, refers to an organism which may be used for virus production and/or adaptation. The host organism may be a cell or an animal such as a laboratory animal. The cell may be an avian cell (e.g. a chicken, quail, goose, or duck cell such as a duck retina (CR) cell). The animal, particularly laboratory animal, may be a bird (e.g. a chicken, quail, goose, or duck), canine, mustela, rodent (e.g. a mouse, rat or hamster), an ovine, a caprine, pig, bat (e.g. a megabat or microbat) or a non-human primate (e.g. a monkey such as a great ape). Particularly, the MVA virus of the present invention replicates in an avian cell (e.g. in a chicken, quail, goose, or duck cell) or in a bird (e.g. in a chicken, quail, goose, or duck).

The term "infectious", as used herein, refers to the ability of a virus to replicate in a cell and to produce viral particles. Infectivity can be evaluated either by detecting the virus load or by observing disease progression in a human or in an animal.

The term "vaccine", as used herein, refers to an agent that can be used to elicit protective immunity in a recipient, e.g. human or animal recipient. To be effective, a vaccine can elicit immunity in a portion of the immunized population, as some individuals may fail to mount a robust or protective immune response or, in some cases, any immune response. This inability may stem from the genetic background of the recipient or because of an immunodeficiency condition (either acquired or congenital) or immunosuppression (e.g., due to treatment with chemotherapy or use of immunosuppressive drugs). Vaccine efficacy can be established in animal models. The vaccine of the present invention comprises the MVA virus according to the first aspect or the genome according to the second aspect. In this respect, it should be noted that the MVA virus itself may be the vaccine. It confers protection against pox. However, said virus may further comprise a heterologous nucleic acid sequence, e.g. a sequence coding for an antigen, particularly an epitope of an antigen, against which an additional protective immunity in the recipient may be elicited. A MVA virus comprising a heterologous nucleic acid sequence can also be designated as recombinant MVA virus.

The term "vaccination", as used herein, means that a recipient, e.g. human or animal recipient, is challenged with an infectious virus, e.g. in an attenuated or inactivated form of said infectious virus, to induce a specific immunity. In the present invention, the recipient is challenged with the MVA virus according to the first aspect or with the genome according to the second aspect to induce immunity against pox. However, in the context of the present invention, the term "vaccination" also covers the challenge of a recipient with a MVA virus which further comprises a heterologous nucleic acid sequence. The heterologous sequence is a sequence against which an additional protective immunity should be elicited. It may code for an antigen, particularly an epitope of an antigen. A MVA virus comprising a heterologous nucleic acid sequence can also be designated as recombinant MVA virus.

Examples of such epitopes which are heterologous to said virus cover, e.g. epitopes from proteins of other viruses such as the Influenza virus, Hepatitis virus, e.g. Hepatitis C virus, Human immunodeficiency virus (HIV), Flavivirus, Paramyxovirus, Hantavirus or Filovirus, or epitopes derived from proteins that are associated with the development of tumours and cancer. After the administration of the vaccine into the body of the recipient, the epitopes are expressed and are presented to the immune system and a specific immune response against these epitopes may be induced. The recipient is, thus, immunized against the protein containing the epitope.

The term "heterologous nucleic acid sequence", as used herein, refers to a nucleic acid sequence that is not normally found intimately associated with the virus, particularly with the MVA virus according to the present invention, in nature. A virus comprising a heterologous nucleic acid sequence may also be designated as recombinant virus.

The term "protect", as used herein, means to prevent or treat, or both, as appropriate, the development or continuance of a disease (e.g. pox) in a recipient, e.g. human.

The term "protective immunity", as used herein, comprises a humoral (antibody) immunity or cellular immunity, or both, effective to, e.g. eliminate or reduce the load of a pathogen (e.g. virus, such as pox virus) or infected cell or produce any other measurable alleviation of the infection in an immunized (vaccinated) subject.

As mentioned above, the inventors of the present invention characterized stable isolates of subsequent generations of an already adapted and hyperattenuated MVA virus on a cell substrate fully permissive for the same hyperattenuated virus under highly artificial conditions imposed by virus production in a chemically defined suspension culture. The above characterization resulted in the identification of novel MVA viruses with point mutations in structural proteins. The novel MVA viruses show beneficial properties in a chemically defined suspension culture compared to known MVA virus strains such as an increased infectious activity and a greater number of infectious units in the extracellular space. Said beneficial properties improve the industrial production of said MVA viruses. Particularly, they allow the production of the novel MVA virus strains in high yields. In addition, the novel MVA virus strains can be isolated directly from the cell-free supernatant which facilitates purification and, thus, the logistic and the operation of bioreactors producing said MVA viruses. This, in turn, reduces the costs of MVA virus production.

Accordingly, the first aspect of the present invention relates to a (mutated) Modified Vaccinia Ankara (MVA) virus comprising a nucleic acid sequence encoding an A3L gene product and/or an A34R gene product, wherein said nucleic acid sequence comprises at least one mutation (e.g. 1, 2, 3, 4, 5, or 6 mutation(s)) resulting in an/at least one amino acid sequence modification (e.g. 1, 2, 3, 4, 5, or 6 amino acid sequence modification(s)) of said gene product(s) (i.e. said A3L gene product and/or said A34R gene product).

It should be noted that the nucleic acid sequence encoding the above gene products comprises at least one mutation (e.g. 1, 2, or 3 mutation(s)) resulting in an/at least one amino acid modification (e.g. 1, 2, or 3 amino acid sequence modification(s)) of each of said gene products.

Said amino acid sequence modification(s) (e.g. 1, 2, 3, 4, 5, or 6 amino acid modification(s)) may be (an) amino acid deletion(s) (e.g. 1, 2, 3, 4, 5, or 6 amino acid deletion(s)), amino acid insertion(s) (e.g. 1, 2, 3, 4, 5, or 6 amino acid insertion(s)), amino acid addition(s) (e.g. 1, 2, 3, 4, 5, or 6 amino acid additions(s)) and/or amino acid replacement(s) (e.g. 1, 2, 3, 4, 5, or 6 amino acid replacement(s)). An "amino acid replacement" may also be designated herein as an "amino acid substitution". The term "amino acid insertion", as used herein, refers to an amino acid modification which takes place within the amino acid sequence of the A3L, A34R, and/or A9L gene product(s), while the term "amino acid addition", as used herein, refers to an amino acid modification which takes place at the N- or C-terminus of the A3L, A34R, and/or A9L gene product(s).

In one embodiment, the MVA virus comprises a nucleic acid sequence encoding an A3L gene product, wherein said nucleic acid sequence comprises at least one mutation (e.g. 1, 2, or 3 mutation(s)) resulting in an/at least one amino acid sequence modification (e.g. 1, 2, or 3 amino acid modification(s)) of said A3L gene product. In another embodiment, the MVA virus comprises a nucleic acid sequence encoding an A34R gene product, wherein said nucleic acid sequence comprises at least one mutation (e.g. 1, 2, or 3 mutation(s)) resulting in an/at least one amino acid sequence modification (e.g. 1, 2, or 3 amino acid modification(s)) of said A34R gene product.

Preferably, the nucleic acid sequence further encodes an A9L gene product, wherein said nucleic acid sequence comprises at least one mutation (e.g. 1, 2, or 3 mutation(s)) resulting in an/at least one amino acid sequence modification (e.g. 1, 2, or 3 amino acid modification(s)) of said gene product.

More preferably,
(i) the virus comprises a nucleic acid sequence encoding an A3L gene product and an A9L gene product, wherein said nucleic acid sequence comprises at least one mutation (e.g. 1, 2, 3, 4, 5, or 6 mutation(s)) resulting in an/at least one amino acid sequence modification (e.g. 1, 2, 3, 4, 5, or 6 amino acid modification(s)) of said gene products (i.e. said A3L gene product and said A9L gene product),
(ii) the virus comprises a nucleic acid sequence encoding an A34R gene product and an A9L gene product, wherein said nucleic acid sequence comprises at least one mutation (e.g. 1, 2, 3, 4, 5, or 6 mutation(s)) resulting in an/at least one amino acid sequence modification (e.g. 1, 2, 3, 4, 5, or 6 amino acid modification(s)) of said gene products (i.e. said A34R gene product and said A9L gene product), or
(iii) the virus comprises a nucleic acid sequence encoding an A3L gene product, an A34R gene product and an A9L gene product, wherein said nucleic acid sequence comprise at least one mutation (e.g. 1, 2, 3, 4, 5, 6, 7, 8, or 9 mutation(s)) resulting in an/at least one amino acid sequence modification (e.g. 1, 2, 3, 4, 5, 6, 7, 8, or 9 amino acid modification(s)) of said gene products (i.e. said A3L gene product, said A34R gene product and said A9L gene product).

It should be noted that the nucleic acid sequence encoding the above gene products comprises at least one mutation (e.g. 1, 2, or 3 mutation(s)) resulting in an/at least one amino acid sequence modification (e.g. 1, 2, or 3 amino acid modification(s)) of each of said gene products.

Said amino acid sequence modification(s) (e.g. 1, 2, 3, 4, 5, 6, 7, 8, or 9 amino acid modification(s)) may be (an) amino acid deletion(s) (e.g. 1, 2, 3, 4, 5, 6, 7, 8, or 9 amino acid deletion(s)), amino acid insertion(s) (e.g. 1, 2, 3, 4, 5, 6, 7, 8, or 9 amino acid insertion(s)), amino acid addition(s) (e.g. 1, 2, 3, 4, 5, 6, 7, 8, or 9 amino acid additions(s)) and/or amino acid replacement(s) (e.g. 1, 2, 3, 4, 5, 6, 7, 8, or 9 amino acid replacement(s)).

The inventors of the present invention surprisingly found that such a mutated MVA virus can be produced in higher yields than a non-mutated MVA virus.

It is preferred that (i) the amino acid sequence modification (e.g. amino acid deletion or amino acid replacement) is in a region spanning amino acid positions 634 to 644, preferably amino acid positions 636 to 642, of the A3L gene product according to SEQ ID NO: 1, or amino acid positions corresponding thereto, (ii) the amino acid sequence modification (e.g. amino acid deletion or amino acid replacement) is in a region spanning amino acid positions 81 to 91, preferably amino acid positions 83 to 89, of the A34R gene product according to SEQ ID NO: 2, or amino acid positions corresponding thereto, and/or (iii) the amino acid sequence modification (e.g. amino acid deletion or amino acid replacement) is in a region spanning amino acid positions 70 to 80, preferably amino acid positions 72 to 78, of the A9L gene product according to SEQ ID NO: 3, or amino acid positions corresponding thereto.

Thus, the amino acid sequence modification (e.g. amino acid deletion or amino acid replacement) may be (i) at amino acid position 634, 635, 636, 637, 638, 639, 640, 641, 642, 643, or 644 of the A3L gene product according to SEQ ID NO: 1, or at an amino acid position corresponding thereto, (ii) at amino acid position 81, 82, 83, 84, 85, 86, 87, 88, 89, 90, or 91 of the A34R gene product according to SEQ ID NO: 2, or at an amino acid position corresponding thereto, and/or (iii) at amino acid position 70, 71, 72, 73, 74, 75, 76, 77, 78, 79, or 80 of the A9L gene product according to SEQ ID NO: 3, or at an amino acid position corresponding thereto.

In the context of the present invention, amino acid residues in two or more gene products are said to "correspond" to each other if the residues occupy an analogous position in the gene product structures. As is well known in the art, analogous positions in two or more gene products can be determined by aligning the gene product sequences based on amino acid sequence or structural similarities. Such alignment tools are well known to the person skilled in the art and can be, for example, obtained on the World Wide Web, e.g., ClustalW or Align using standard settings, preferably for Align EMBOSS::needle, Matrix: Blosum62, Gap Open 10.0, Gap Extend 0.5. Those skilled in the art understand that it may be necessary to introduce gaps in either sequence to produce a satisfactory alignment Amino acid residues in two or more gene products are said to "correspond" if the residues are aligned in the best sequence alignment. The "best sequence alignment" between two gene products is defined as the alignment that produces the largest number of aligned identical residues. The "region of best sequence alignment" ends and, thus, determines the metes and bounds of the length of the comparison sequence for the purpose of the determination of the similarity score, if the sequence similarity, preferably identity, between two aligned sequences drops to less than 30%, preferably less than 20%, more preferably less than 10% over a length of 10, 20 or 30 amino acids.

It is further preferred that (i) the amino acid sequence modification (e.g. amino acid deletion or amino acid replacement) is at amino acid position 639 of the A3L gene product or at an amino acid position corresponding thereto, (ii) the amino acid sequence modification (e.g. amino acid deletion or amino acid replacement) is at amino acid position 638 of the A3L gene product or at an amino acid position corresponding thereto, (iii) the amino acid sequence modification (e.g. amino acid deletion or amino acid replacement) is at amino acid position 86 of the A34R gene product or at an amino acid position corresponding thereto, (iv) the amino acid sequence modification (e.g. amino acid deletion or amino acid replacement) is at amino acid position 75 of the A9L gene product or at an amino acid position corresponding thereto, and/or (v) the amino acid sequence modification (e.g. amino acid deletion or amino acid replacement) is at amino acid position 74 of the A9L gene product or at an amino acid position corresponding thereto.

It is more preferred that the amino acid sequence modification is an amino acid deletion or amino acid replacement, wherein (i) H at amino acid position 639 of the A3L gene product or at an amino acid position corresponding thereto is deleted or replaced by a hydrophobic amino acid, preferably A, V, I, L, M, F, Y or W, a negative amino acid, preferably D or E, or a polar uncharged amino acid, preferably S, T, N or Q, (ii) R at amino acid position 638 of the A3L gene product or at an amino acid position corresponding thereto is deleted or replaced by a hydrophobic amino acid, preferably A, V, I, L, M, F, Y or W, a negative amino acid, preferably D or E, or a polar uncharged amino acid, preferably S, T, N or Q, (iii) D at amino acid position 86 of the A34R gene product or at an amino acid position corresponding thereto is deleted or replaced by a hydrophobic amino acid, preferably A, V, I, L, M, F, Y or W, a positive amino acid, preferably R, H or K, or a polar uncharged amino acid, preferably S, T, N or Q, (iv) K at amino acid position 75 of the A9L gene product or at an amino acid position corresponding thereto which is deleted or replaced by a hydrophobic amino acid, preferably A, V, I, L, M, F, Y or W, a negative amino acid, preferably D or E, or a polar uncharged amino acid, preferably S, T, N or Q, and/or (v) K at amino acid position 74 of the A9L gene product or at an amino acid position corresponding thereto which is deleted or replaced by a hydrophobic amino acid, preferably A, V, I, L, M, F, Y or W, a negative amino acid, preferably D or E, or a polar uncharged amino acid, preferably S, T, N or Q.

It is even more preferred that the amino acid replacement is an amino acid replacement of (i) H at amino acid position 639 of the A3L gene product or at an amino acid position corresponding thereto by Y (H639Y A3L gene product mutant), (ii) R at amino acid position 638 of the A3L gene product or at an amino acid position corresponding thereto by Y (R638Y A3L gene product mutant), (iii) D at amino acid position 86 of the A34R gene product or at an amino acid position corresponding thereto by Y (D86Y A34R gene product mutant), (iv) K at amino acid position 75 of the A9L gene product or at an amino acid position corresponding thereto by E (K75E A9L gene product mutant), and/or (v) K at amino acid position 74 of the A9L gene product or at an amino acid position corresponding thereto by E (K74E A9L gene product mutant).

It is further even more preferred that the amino acid replacement is an amino acid replacement of (i) H at amino acid position 639 of the A3L gene product or at an amino acid position corresponding thereto by Y and D at amino acid position 86 of the A34R gene product or at an amino acid position corresponding thereto by Y (H639Y A3L/D86Y A34R gene product mutant),
(ii) H at amino acid position 639 of the A3L gene product or at an amino acid position corresponding thereto by Y and K at amino acid position 75 of the A9L gene product or at an amino acid position corresponding thereto by E (H639Y A3L/K75E A9L gene product mutant),
(iii) D at amino acid position 86 of the A34R gene product or at an amino acid position corresponding thereto by Y and K at amino acid position 75 of the A9L gene product or at an amino acid position corresponding thereto by E (D86Y A34R/K75E A9L gene product mutant), or
(iv) H at amino acid position 639 of the A3L gene product or at an amino acid position corresponding thereto by Y, D at amino acid position 86 of the A34R gene product or at an amino acid position corresponding thereto by Y, and K at amino acid position 75 of the A9L gene product or at an amino acid position corresponding thereto by E (H639Y A3L/D86Y A34R/K75E A9L gene product mutant).

It is most preferred that
(i) the A3L gene product with the H639Y mutation has an amino acid sequence according to SEQ ID NO: 4 or is a variant thereof which is at least 85%, preferably 90%, more preferably 95%, and most preferably 99%, e.g. at least 85, 86, 87, 88, 89, 90, 91, 92, 93, 94, 95, 96, 97, 98, or 99%, identical to said amino acid sequence, wherein said variant (still) comprises the amino acid Y at amino acid position 639 or at an amino acid position corresponding thereto,
(ii) the A34R gene product with the D86Y mutation has an amino acid sequence according to SEQ ID NO: 5 or is a variant thereof which is at least 85%, preferably 90%, more preferably 95%, and most preferably 99%, e.g. at least 85, 86, 87, 88, 89, 90, 91, 92, 93, 94, 95, 96, 97, 98, or 99%, identical to said amino acid sequence, wherein said variant (still) comprises the amino acid Y at amino acid position 86 or at an amino acid position corresponding thereto, and/or
(iii) the A9L gene product with the K75E mutation has an amino acid sequence according to SEQ ID NO: 6 or is a variant thereof which is at least 85%, preferably 90%, more preferably 95%, and most preferably 99%, e.g. at least 85, 86, 87, 88, 89, 90, 91, 92, 93, 94, 95, 96, 97, 98, or 99%, identical to said amino acid sequence, wherein said variant (still) comprises the amino acid E at amino acid position 75 or at an amino acid position corresponding thereto.

It is particularly preferred that the sequence identity is (i) at least 85%, 90%, 95%, or 99% over a continuous stretch of at least 50, 60, 70, 80, 90, 100, 120, 150, 180, 200, 300, 400, 500, 600, or more amino acids of the respective reference amino acid sequence according to SEQ ID NO: 4, (ii) at least 85%, 90%, 95%, or 99% over a continuous stretch of at least 20, 30, 40, 50, 60, 70, 80, 90, 100, 110, 120, 130, 140, 150, 160, or more amino acids of the respective reference amino acid sequence according to SEQ ID NO: 5, or (iii) at least 85%, 90%, 95%, or 99% over a continuous stretch of at least 20, 30, 40, 50, 60, 70, 80, 90, or more amino acids of the respective reference amino acid sequence according to SEQ ID NO: 6. It is further particularly preferred that the sequence identity is at least 85% over the whole length, is at least 90% over the whole length, is at least 95% over the whole length, or is at least 99% over the whole length of the respective reference amino acid sequence according to SEQ ID NO: 4, SEQ ID NO: 5, or SEQ ID NO: 6.

Preferably, the above variants are functionally active variants. This means that the (additional) variation(s) in the amino acid sequence does/do not negatively affect the beneficial properties of the MVA virus according to the present invention compared to known MVA viruses such as an increased infectious activity and/or a greater number of infectious units in the extracellular space during culturing. Said beneficial properties allow, for example, the production of the MVA virus according to the present invention in high yields. Experiments to test that said beneficial properties are still present in the above variants are described in the experimental section.

The above mentioned A3L gene product (also designated as P4b protein) of MVA is one of three major core proteins and is processed by the I7L-encoded viral protease during the maturation of the spherical and non-infectious immature virion (IV) to the intracellular mature virion (IMV). The A3L gene product of MVA contributes to virion morphogenesis at a very early step to allow correct condensation and membrane rearrangements in the transition towards the infectious IMV. Further, the above mentioned A34R gene product of MVA destabilizes the outer membrane of the extracellular enveloped virus (EEV) and is, thus, extremely important for infectious activity in the extracellular space and for virus spread. The EEV has evolved as a vehicle to allow virus to spread to distant sites. The additional membrane of the EEV is not equipped to mediate fusion with the target cell and must be disrupted to release the IMV, the actual virus infectious unit. In addition, the A34R gene product of MVA modulates the rate at which the cell-associated enveloped virus (CEV) detaches from the producing cell. Furthermore, the A9L gene product of MVA is, like the A3L gene product, involved in the early steps of MVA maturation. It is a factor important for correct condensation of the core of the IMV.

Preferably, the MVA virus is an isolated MVA virus. The term "isolated MVA virus", as used herein, refers to a virus that is removed from its native or culturing environment. Thus, an isolated MVA virus may be free of some or all cellular components, i.e. components of the cells in which the virus naturally occurs or in which it is cultured (e.g. cytoplasmic or membrane components). It may also be free of some or all culturing components (e.g. culture medium or culture-related impurities such as culture-remnants).

The isolated MVA virus may further be purified. Thus, more preferably, the MVA virus is a purified MVA virus. The term "purified MVA virus", as used herein, refers to a virus that has been isolated under conditions that reduce or eliminate the presence of unrelated materials, i.e. contaminants, including native materials, e.g. cellular debris, cellular remnants, cellular proteins, cellular DNA molecules, and/or cellular RNA molecules, from which the virus is obtained. The purified MVA virus is preferably substantially free of cell and/or culture components. As used herein, the term "substantially free" is used operationally, in the context of analytical testing of the material. A purified MVA virus which is substantially free of contaminants is preferably at least 50% pure, more preferably at least 90% pure, and even more preferably at least 99% or 100% pure. Purity can be evaluated by chromatography, gel electrophoresis, immunoassay, composition analysis, biological assay, and other methods known in the art.

It is preferred that the MVA virus further comprises a heterologous nucleic acid sequence. The term "heterologous nucleic acid sequence" is defined above. The expression of the heterologous nucleic acid sequence may be under the transcriptional control of a MVA virus promoter. The heterologous nucleic acid sequence is inserted into the nucleic acid sequence of the MVA virus. In a preferred embodiment of the present invention, the insertion of the heterologous nucleic acid sequence is into a non-essential region of the MVA virus nucleic acid sequence/genome. In a more preferred embodiment of the present invention, the heterologous nucleic acid sequence is inserted at a naturally occurring deletion site (e.g. deletion site I, II, III, IV, V, or VI) of the MVA nucleic acid sequence/genome. Methods how to insert heterologous nucleic acid sequences into the MVA virus genome are known to a skilled person.

It is more preferred that the heterologous nucleic acid sequence is selected from a sequence coding for an antigen, particularly an epitope of an antigen, a diagnostic compound, or a therapeutic compound. The term "epitope (also known as antigenic determinant)" refers to the part of an antigen that is recognized by the immune system, specifically by antibodies, B cells, or T cells.

The antigen or epitope may be useful as a vaccine to induce an immune response against said antigen or epitope. Examples of such antigens which are heterologous to said virus cover, e.g. proteins of other viruses such as the Influenza virus, Hepatitis virus, e.g. Hepatitis C virus, Human immunodeficiency virus (HIV), Flavivirus, Paramyxovirus, Hantavirus or Filovirus, or proteins that are associated with the development of tumours and cancer such as Her2/neu or MUC-1. Examples of such epitopes which are heterologous to said virus cover, e.g. epitopes from proteins derived from other viruses such as the Influenza virus, Hepatitis virus, e.g. Hepatitis C virus, Human immunodeficiency virus (HIV), Flavivirus, Paramyxovirus, Hantavirus or Filovirus, or epitopes derived from proteins that are associated with the development of tumours and cancer such as extracellular peptides of Her2/neu or MUC-1.

The therapeutic compound may be any compound with a therapeutic effect. For example, the therapeutic compound can be a compound that affects or participates in tissue growth, cell growth, cell differentiation, a compound that is able to invoke a biological action such as an immune response, or a compound that can play any other role in one or more biological processes. Particularly, said compound may be an anti-microbial compound, an anti-viral compound, an anti-fungal compound, an immunosuppressive compound, a growth factor, an enzyme, an anti-inflammatory compound, or an anti-allergic compound. The therapeutic compound may also be an antisense nucleic acid.

The diagnostic compound may be any compound with a diagnostic effect. For example, the diagnostic compound can be a marker/reporter protein such as an antibody, GFP, EGFP, β-Galactosidase, or an antibiotic resistance conferring protein such as bla (beta-lactamase) against ampicillin or npt (neomycin phosphotransferase) against neomycin or G418. Said marker/reporter protein may be used to identify or isolate the virus, e.g. by using hybridization technology, fluorescence microscopy, or ELISA assays. In addition, the antibiotic resistance conferring protein comprised in the virus confers resistance against antibiotic selection to the infected cell.

As already mentioned above, the MVA virus is a highly attenuated virus. In one embodiment of the present invention, the MVA virus is capable of productive replication in avian cells. The term "productive replication", as used herein, may mean that a virus causes a cytopathic effect and replicates to levels that eventually cause massive cell death in the infected culture. For reproductive replication, more virus can be recovered at least once from an infected culture than virus that has been added to infect the culture. As opposed to productive replication, reproductive replication can occur at very low levels without accompanying cytopathic effect and may eventually lead to loss of virus in a surviving culture.

Said avian cells are preferably chicken, quail, goose, or duck cells (e.g. duck somite or duck retina cells). Said avian cells (e.g. chicken, quail, goose, or duck cells such as duck somite or duck retina cells) may be primary cells (or cells from a primary cell culture), secondary cells (or cells from a secondary cell culture), or immortalized cells (or cells from a cell line). The terms a "primary cell" or "primary cell culture", as used herein, refer to a cell or culture which usually can not be passaged beyond 50 population doublings before suffering senescence, culture arrest, or cell death. The terms a "secondary cell" or "secondary cell culture", as used herein, refer to a cell or culture which is directly derived from a primary cell or primary cell culture. The population doubling limit still applies. The terms an "immortalized cell" or "immortalized cell culture", as used herein, refer to a cell or culture and its progeny that is not limited by the number of potential cell doublings. A cell culture may consist of primary cells, secondary cells, or immortalized cells (i.e. cells of a cell line). In preferred embodiments of the present invention, the cells are from a CR or CR.pIX cell line. The CR and CR.pIX cell lines are derived from immortalized Muscovy duck retina cells (Jordan, et al. 2009 in Vaccine 27, 748-756), designed for vaccine production. The CR.pIX cell line has further stably integrated into its genome a gene encoding the Adenovirus pIX protein and expresses said gene. In other preferred embodiments of the present invention, the cells are chicken embryo fibroblast (CEF) cells. Said cells are primary cells.

In another embodiment of the present invention, the MVA virus is not capable of productive replication in mammalian cells, wherein said mammalian cells are not Baby Hamster Kidney (BHK) cells, Fruit bat R05T cells, Fruit bat R05R cells, or Fruit bat R06E cells. R05T, R05R, and R06E cells are cells obtained by immortalization of primary cells from the Egyptian rousette. These are one of the very few mammalian cell lines permissive for MVA (Jordan et al. 2009 in Virus Res 145, 54-62). In a preferred embodiment of the present invention, the MVA virus is not capable of productive replication in primate cells, more preferably human cells.

The MVA virus according to the present invention may comprise a nucleic acid sequence encoding an A3L gene product having an amino acid sequence prior to amino acid modification according to SEQ ID NO: 1 and/or an A34R gene product having an amino acid sequence prior to amino acid modification according to SEQ ID NO: 2. Said nucleic acid sequence may further encode an A9L gene product having an amino acid sequence prior to amino acid modification according to SEQ ID NO: 3.

Further, the respective A3L gene may have a nucleic acid sequence prior to mutation according to SEQ ID NO: 7, the respective A34R gene may have a nucleic acid sequence prior to mutation according to SEQ ID NO: 8, and/or the respective A9L gene may have a nucleic acid sequence prior to mutation according to SEQ ID NO: 9.

Furthermore, the mutated A3L gene may have a nucleic acid sequence according to SEQ ID NO: 10, the mutated A34R gene may have a nucleic acid sequence according to SEQ ID NO: 11, and/or the mutated A9L gene may have a nucleic acid sequence according to SEQ ID NO: 12.

In addition, the MVA virus according to the present invention may comprise a nucleic acid sequence prior to mutation according to accession number AY603355 (version AY603355.1 and GI:47088326).

In a second aspect, the present invention relates to a genome of the (mutated) MVA virus according to the first aspect.

In a third aspect, the present invention relates to a cell comprising a (mutated) MVA virus according to the first aspect or a genome according to the second aspect. The cell comprising a MVA virus according to the first aspect or a genome according to the second aspect may also be designated as host cell. Said cell may be for culturing the MVA virus according to the first aspect. Said cell may be any cell in which the MVA virus according to the first aspect is capable to replicate. It is preferred that said cell is not a primate cell, particularly a human cell. It is further preferred that said cell is an avian cell. Said avian cell is preferably a chicken, quail, goose, or duck cell (e.g. a duck somite or duck retina cell). Said avian cell (e.g. chicken, quail, goose, or duck cell such as duck somite or duck retina cell) may be a primary cell (or a cell from a primary cell culture), a secondary cell (or a cell from a secondary cell culture), or an immortalized cell (or a cell from a cell line). As to the definition of the terms "primary cell", "primary cell culture", "secondary cell", "secondary cell culture", "immortalized cell", or "immortalized cell culture", it is referred to the first aspect of the present invention. In preferred embodiments of the present invention, the cell is from a CR or CR.pIX cell line. The CR and CR.pIX cell lines are derived from immortalized Muscovy duck retina cells (Jordan, et al. 2009 in Vaccine 27, 748-756), designed for vaccine production. The CR.pIX cell line has further stably integrated into its genome a gene encoding the Adenovirus pIX protein and expresses said gene. In other preferred embodiments of the invention, the cells are chicken embryo fibroblast (CEF) cells. Said cells are primary cells.

Preferably, the cell is an isolated cell. The term "isolated cell", as used herein, refers to a cell that is removed from its native or culturing environment. Thus, an isolated cell may be free of some or all native or culture components, i.e. components of the organism in which the cell naturally occurs (e.g. organ particularly tissue) or in which it is cultured (e.g. culture medium or culture-related impurities such as culture remnants).

The cell may be infected with a MVA virus according to the first aspect or transfected with a genome according the second aspect. Techniques how to infect or transfect a cell are known to the skilled person.

It is further preferred that the cell is a non-adherent/suspension cell. Generally, cells can be grown in suspension or adherent cultures. Some cells naturally live in suspension, without being attached to a surface, such as cells that exist in the bloodstream (e.g. hematopoietic cells). Adherent cells (e.g. primary cells) require a surface, such as tissue culture plastic carrier or micro-carrier, which may be coated with extracellular matrix components to increase adhesion properties and provide other signals needed for growth and differentiation. Most cells derived from solid tissues are adherent. Adherent cells are usually used in their original form for cell biology research. There are also cells that have been modified to be able to survive in suspension cultures so that they can be grown to a higher density than adherent conditions would allow. Under adherent conditions, growth is namely limited by surface area, which may limit product yields. Such suspension adapted cells or cells adapted to non-adherent grow are usually used for bulk protein production or batch harvesting. Under non-adherent conditions, growth is limited by concentration of cells in the culture medium, which allows easier scale-up.

The terms "non-adherent" and "suspension" are used interchangeable herein. In the context of the present invention, the terms "non-adherent cell" and "suspension cell" refer to a cell that is able to survive in a suspension culture without being attached to a surface (e.g. tissue culture plastic carrier or micro-carrier). Said cell may be a cell which can naturally live in suspension without being attached to a surface. Said cell may also be a cell which has been modified or adapted to be able to survive in a suspension culture without being attached to a surface (e.g. tissue culture plastic carrier or micro-carrier). As mentioned above, most cells are in their original, non-modified or non-adapted form, adherent cells. A non-adherent cell can usually be grown to a higher density than adherent conditions would allow. It is, thus, more suited for culturing in an industrial scale, e.g. in a bioreactor setting or in an agitated culture. Cells have usually to be adapted to a non-adherent cell culture. Because the original cells would undergo apoptosis under serum-free conditions and/or in the absence of a suitable surface, this adaptation is a prolonged process requiring passaging with diminishing amounts of serum (e.g. dilution rows from 10% to 0% Fetal Calve Serum (FCS)), thereby selecting an irreversibly modified cell population. Adapted non-adherent cells are known in the art. The skilled person is aware of protocols for transferring a cell from an adherent state into a non-adherent state (see, for example, Appl Microbiol Biotechnol. 2008 March; 78(3):391-9. Epub 2008 Jan. 9).

In contrast thereto, the term "adherent cell", as used herein, refers to a cell which requires a surface, such as tissue culture plastic carrier or micro-carrier. Said surface may be coated with extracellular matrix components to increase adhesion properties and provide other signals needed for growth and differentiation. Said cells require periodic passaging, but allow easy visual inspection under inverted microscope. Said cells have to be dissociated enzymatically (e.g. with trypsin). In addition, the growth of adherent cells is limited by surface area, which may limit product yields.

In preferred embodiments of the present invention, the non-adherent/suspension cell grows under serum-free conditions. The term "serum-free conditions", as used herein, refers to conditions, wherein cells grow in medium which is devoid of animal serum. Instead, cells grow in medium devoid of any animal derived components and preferably in a medium without any complex mixtures of biologic components, a so called "chemically defined medium".

In a fourth aspect, the present invention relates to a method for culturing a (mutated) MVA virus according to the first aspect comprising the steps of:
(i) providing a cell according to the third aspect,
(ii) culturing the cell, and
(iii) isolating the (mutated) MVA virus.

The cell according to the third aspect comprises a (mutated) MVA virus according to the first aspect or a genome according to the second aspect. The cell may be cultured in step (ii) in cell proliferation medium and subsequently in virus production medium, or the cell may be (solely) cultured in step (ii) in cell proliferation medium. Preferably, the cell is (solely) cultured in step (ii) in cell proliferation medium. The use of a single medium has the advantage that it facilitates the MVA virus culturing process, particularly the industrial MVA virus culturing process. For example, it facilitates the logistic and the operation of bioreactors producing said MVA virus.

It is preferred that the cell is cultured in cell proliferation medium between 1 day and 3 days, e.g. 1, 2, or 3 day(s), and that the cell is subsequently cultured in virus production medium between 1 to 10 days, e.g. 1, 2, 3, 4, 5, 6, 7, 8, 9, or 10 days. It is also preferred that the cell is solely cultured in proliferation medium between 1 to 10 days, e.g. 1, 2, 3, 4, 5, 6, 7, 8, 9, or 10 days.

The term "cell proliferation medium", as used herein, refers to a medium that supports cell division for at least 10 cell doublings so that, for example, a seed of 8×10^5 cells by passage in that medium can be brought to approximately 4×10^8 cells, e.g. sufficient for a 200 Liter bioreactor. The term "proliferating cells", as used herein, refers to dividing cells, i.e. cells that can divide for another at least 10 cell doublings with a doubling rate of at least once in 48 hours or less.

It is preferred that the cell proliferation medium is serum-free. A serum-free medium is particularly devoid of animal serum. Instead, cells grow in medium devoid of any animal derived components and preferably in a medium without any complex mixtures of biologic components, a so called "chemically defined medium". It is further preferred that the cell proliferation medium has a low protein content and/or a low salt content. Preferably, the (low) protein content is in a range of between 10 and 250 ng/ml, more preferably between 50 and 200 ng/ml, even more preferably between 50 and 150 ng/ml, and most preferably between 50 and 100 ng/ml, e.g. 10, 20, 30, 40, 50, 60, 70, 80, 90, 100, 110, 120, 130, 140, 150, 160, 170, 180, 190, 200, 210, 220, 230, 240, or 250 ng/ml. Preferably, the (low) salt content is in a range of between 150 and 350 mOsm/kg, more preferably between 180 and 350 mOsm/kg, even more preferably between 200 and 320 mOsm/kg, and most preferably between 250 and 300 mOsm/kg, e.g. 150, 160, 170, 180, 190, 200, 210, 220, 230, 240, 250, 260, 270, 280, 290, 300, 310, 320, 330, 340, or 350 mOsm/kg. It is preferred that the above cell proliferation medium further includes glucose. Preferably, the glucose content is in a range of between 1 and 6 g/l, more preferably between 2.5 and 5.5 g/l, even more preferably between 3.5 and 5 g/l, and most preferably between 4 and 4.5 g/l, e.g. 1, 1.5, 2, 2.5, 3, 3.5, 4, 4.5, 5, 5.5, or 6 g/l. Thus, in one embodiment of the present invention, the cell proliferation medium is serum-free, has a low protein content, and has a low salt content. In another preferred embodiment of the invention, the cell proliferation medium is serum-free, has a low protein content, has a low salt content and further comprises glucose. The preferred amounts are described above.

The term "virus production medium", as used herein, refers to a medium that enhances production of a virus in a culture of proliferating cells. With the addition of a virus production medium, cell aggregates are induced and cell proliferation in the culture decreases by a factor of at least 2 or is stopped completely. It is preferred that the virus production medium comprises $CaCl_2$, $MgSO_4$ and/or NaCl. Preferably, the $CaCl_2$ content is in a range of between 150 and 250 mg/l, more preferably between 180 and 250 mg/l, and most preferably between 200 and 220 mg/l, e.g. 150, 155, 160, 165, 170, 175, 180, 185, 190, 195, 200, 205, 210, 215, 220, 225, 230, 235, 240, 245, or 250 mg/l, the $MgSO_4$ content is in a range of between 50 and 150 mg/l, more preferably between 70 and 150 mg/l, and most preferably between 90 and 120 mg/l, e.g. 50, 55, 60, 65, 70, 75, 80, 85, 90, 95, 100, 105, 110, 115, 120, 125, 130, 135, 140, 145, or 150 mg/l, and/or the NaCl content is in a range of between 5000 and 7500 mg/l, more preferably between 6000 and 7000 mg/l, and most preferably between 6500 and 6800 mg/l, e.g. 5000, 5500, 6000, 6500, 7000, or 7500 mg/l. For example, the virus production medium may include a salt content of 205 mg/l $CaCl_2$, 100 mg/l $MgSO_4$ and/or 6500 mg/l NaCl.

Preferably, the cell is cultured in step (ii) in an agitated culture or in a bioreactor. Bioreactors are generally categorized similarly to chemical reactors according to their mixing characteristics. Said bioreactor may be a (well mixed) stirred tank reactor or a plug flow (tubular) reactor. In an ideal well-mixed bioreactor, the mixing is assumed to be intense enough that the fluid (cells and culture medium) is homogenous through the reactor. In preferred embodiments, the bioreactor is a fed-batch, batch, or continuous bioreactor or the culturing is a batch, fed-batch or continuous culturing process. A bioreactor is usually called continuous, when the feed and product streams are continuously being fed and withdrawn from the system. In principal, a reactor can have a continuous recirculating flow, but no continuous feeding of nutrient or product harvest; it is still a batch bioreactor. A fed-batch bioreactor usually has intermittent feed. It may or may not have medium withdrawal during the run. The term "fed-batch culture", as used herein, may refer to a process of culturing cells in which a defined amount of cells is provided in a suitable culture medium and cultivated in suspension for a prolonged time (typically 4-10 days) during which time no medium is removed. However, additional components are provided to the culture at some time subsequent to the beginning of the culture process. The provided components typically comprise nutritional supplements for the cells that have been depleted during the culturing process. A fed-batch culture is typically stopped at a point where the ratio of living to dead cells drops below a critical value.

The MVA virus according to the first aspect may be isolated from the cell-free supernatant and/or cell lysate. The isolation of the MVA virus according to the first aspect from the cell-free supernatant and/or cell lysate may be performed according to standard procedures readily available to the skilled person. Preferably, the MVA virus according to the first aspect is isolated from the cell-free supernatant. The inventors of the present invention have namely shown that the MVA virus according to the first aspect can be isolated directly from the cell-free supernatant which facilitates the MVA virus isolation process, particularly the industrial MVA virus isolation process. This, in turn, reduces the costs of MVA virus production. For example, cell lyses for MVA virus isolation is not required anymore. In this way, the contamination of the MVA virus isolate with cellular material, particularly cellular DNA, can be reduced. As a consequence, the DNA-limit values of the World Health Organisation for virus preparations can easier be obtained.

Various isolation procedures for viruses are known in the art. An isolation procedure which is useful according to the invention does not interfere with the viruses to be isolated. For example, extended exposure to impeller shear forces and other factors that occur during isolation should be avoided. It is preferred that the isolation in step (iii) is achieved by separating the virus from the cells via centrifugation, sedimentation and/or filtration, e.g. via centrifugation and filtration, via sedimentation and filtration, via sedimentation and centrifugation, or via centrifugation, sedimentation and filtration. The person skilled in the art is able to easily adapt/adjust the appropriate separation parameters, e.g. the acceleration-force/G-force and/or time using centrifugation for separation, filter size using filtration for separation, and/or sedimentation time using sedimentation for separation, in order to isolate the virus cultured in said cells.

In a fifth aspect, the present invention relates to a method for producing a (mutated) MVA virus according to the first aspect comprising the steps of:
(i) infecting a cell with a MVA virus,
(ii) culturing the cell,
(iii) isolating the MVA virus, and
(iv) repeating steps (i) to (iii) with the MVA virus isolated in step (iii) until a (mutated) MVA virus comprising a nucleic acid sequence encoding an A3L gene product and/or an A34R gene product, wherein said nucleic acid sequence comprises at least one mutation (e.g. 1, 2, 3, 4, 5, or 6 mutation(s)) resulting in an/at least one amino acid sequence modification (e.g. 1, 2, 3, 4, 5, or 6 amino acid sequence modification(s)) of said gene product(s) (i.e. said A3L gene product and/or said A34R gene product), is detected.

It should be noted that the nucleic acid sequence encoding the above gene products comprises at least one mutation (e.g. 1, 2, or 3 mutation(s)) resulting in an/at least one amino acid modification (e.g. 1, 2, or 3 amino acid sequence modification(s)) of each of said gene products.

Said amino acid sequence modification(s) (e.g. 1, 2, 3, 4, 5, or 6 amino acid modification(s)) may be (an) amino acid deletion(s) (e.g. 1, 2, 3, 4, 5, or 6 amino acid deletion(s)), amino acid insertion(s) (e.g. 1, 2, 3, 4, 5, or 6 amino acid insertion(s)), amino acid addition(s) (e.g. 1, 2, 3, 4, 5, or 6 amino acid additions(s)) and/or amino acid replacement(s) (e.g. 1, 2, 3, 4, 5, or 6 amino acid replacement(s)).

Preferably, steps (i) to (iii) are repeated until a MVA virus comprising a nucleic acid sequence further encoding an A9L gene product, wherein said nucleic acid sequence comprises at least one mutation (e.g. 1, 2, or 3 mutations(s)) resulting in an/at least one amino acid sequence modification (e.g. 1, 2, or 3 amino acid sequence modification(s)) of said gene product, is detected.

More preferably,
(i) a MVA virus comprising a nucleic acid sequence encoding an A3L gene product and an A9L gene product, wherein said nucleic acid sequence comprises at least one mutation (e.g. 1, 2, 3, 4, 5, or 6 mutation(s)) resulting in an/at least one amino acid sequence modification (e.g. 1, 2, 3, 4, 5, or 6 amino acid modification(s)) of said gene products (i.e. said A3L gene product and said A9L gene product), is detected,
(ii) a MVA virus comprising a nucleic acid sequence encoding an A34R gene product and an A9L gene product, wherein said nucleic acid sequence comprises at least one mutation (e.g. 1, 2, 3, 4, 5, or 6 mutation(s)) resulting in an/at least one amino acid sequence modification (e.g. 1, 2, 3, 4, 5, or 6 amino acid modification(s)) of said gene products (i.e. said A34R gene product and said A9L gene product), is detected, or (iii) a MVA virus comprising a nucleic acid sequence encoding an A3L gene product, an A34R gene product and an A9L gene product, wherein said nucleic acid sequence comprise at least one mutation (e.g. 1, 2, 3, 4, 5, 6, 7, 8, or 9 mutation(s)) resulting in an/at least one amino acid sequence modification (e.g. 1, 2, 3, 4, 5, 6, 7, 8, or 9 amino acid modification(s)) of said gene products (i.e. said A3L gene product, said A34R gene product and said A9L gene product), is detected.

It should be noted that the nucleic acid sequence encoding the above gene products comprises at least one mutation (e.g. 1, 2, or 3 mutation(s)) resulting in an/at least one amino acid sequence modification (e.g. 1, 2, or 3 amino acid modification(s)) of each of said gene products.

Said amino acid sequence modification(s) (e.g. 1, 2, 3, 4, 5, 6, 7, 8, or 9 amino acid modification(s)) may be (an) amino acid deletion(s) (e.g. 1, 2, 3, 4, 5, 6, 7, 8, or 9 amino acid deletion(s)), amino acid insertion(s) (e.g. 1, 2, 3, 4, 5, 6, 7, 8, or 9 amino acid insertion(s)), amino acid addition(s) (e.g. 1, 2, 3, 4, 5, 6, 7, 8, or 9 amino acid additions(s)) and/or amino acid replacement(s) (e.g. 1, 2, 3, 4, 5, 6, 7, 8, or 9 amino acid replacement(s)).

As to the preferred embodiments of the amino acid modifications, it is referred to the first aspect of the present invention.

The MVA virus provided in step (i) particularly comprises a nucleic acid sequence encoding an A3L gene product, an A34R gene product, and an A9L gene product, wherein said nucleic acid sequence does not comprise a mutation resulting in an amino acid sequence modification of said gene products. It particularly does not comprise the preferred amino acid modifications referred to in the first aspect of the present invention.

The MVA virus in step (i) may comprise a nucleic acid sequence according to accession number AY603355 (version AY603355.1 and GI:47088326).

It is preferred that steps (i) to (iii) are repeated at least 2 times, preferably at least 7 times, more preferably at least 14 times, most preferably at least 20 times, e.g. at least 2, 3, 4, 5, 6, 7, 8, 9, 10, 11, 12, 13, 14, 15, 16, 17, 18, 19, or 20 times.

It is further preferred that the cell is cultivated in virus production medium. As to the definition of the term "virus production medium" and as to preferred embodiments of the "virus production medium", it is referred to the fourth aspect of the present invention.

The virus may be cultured in step (ii) in virus production medium between 1 to 10 days, e.g. 1, 2, 3, 4, 5, 6, 7, 8, 9, or 10 days. As to preferred culturing conditions and isolation forms, it is also referred to the fourth aspect of the present invention.

The cell in step (i) may be any cell in which the MVA virus is capable to replicate. It is preferred that said cell is not a primate cell, particularly a human cell. It is further preferred that said cell is an avian cell. Said avian cell is preferably a chicken, quail, goose, or duck cell (e.g. a duck somite or duck retina cell). Said avian cell (e.g. chicken, quail, goose, or duck cell such as duck somite or duck retina cell) may be a primary cell (or a cell from a primary cell culture), a secondary cell (or a cell from a secondary cell culture), or an immortalized cell (or a cell from a cell line). As to the definition of the terms "primary cell", "primary cell culture", "secondary cell", "secondary cell culture", "immortalized cell", or "immortalized cell culture", it is referred to the first aspect of the present invention. In preferred embodiments of the present invention, the cell is from a CR or CR.pIX cell line. The CR and CR.pIX cell lines are derived from immortalized Muscovy duck retina cells (Jordan, et al. 2009 in Vaccine 27, 748-756). The CR.pIX cell line has further stably integrated into its genome a gene encoding the Adenovirus pIX protein and expresses said gene. In other preferred embodiments of the invention, the cells are chicken embryo fibroblast (CEF) cells. Said cells are primary cells.

In a sixth aspect, the present invention also relates to a pharmaceutical composition comprising a MVA virus according to the first aspect or a genome according to the second aspect and one or more pharmaceutical acceptable excipient(s), diluent(s), and/or carrier(s).

As mentioned above, the (mutated) MVA virus according to the first aspect is highly host-restricted and, thus, highly attenuated. It is, therefore, ideal to treat a wide range of recipients.

The terms "host-restricted", "highly attenuated", and "recipient" are defined above. Preferably the recipients are primates, more preferably humans.

The term "excipient", when used herein, is intended to indicate all substances in a pharmaceutical composition which are not active ingredients. Examples of excipients include, but are not limited to, binders, lubricants, thickeners, surface active agents, preservatives, emulsifiers, buffers, flavoring agents, and/or colorants. Acceptable carrier(s) and/or diluent(s) for therapeutic use are well known in the pharmaceutical art and are described, for example, in Remington's Pharmaceutical Sciences, Mack Publishing Co. (A. R Gennaro edit. 1985). Examples of suitable carriers include, but are not limited to, magnesium carbonate, magnesium stearate, talc, sugar, lactose, pectin, dextrin, starch, gelatin, tragacanth, methylcellulose, sodium carboxymethylcellulose, a low melting wax, and/or cocoa butter. Examples of suitable diluents include, but are not limited to, ethanol, glycerol, and/or water. The pharmaceutical excipient(s), diluent(s), and/or carrier(s) can be selected with regard to the intended route of administration and standard pharmaceutical practice. The pharmaceutical compositions may further comprise suitable binder(s), lubricant(s), suspending agent(s), coating agent(s), and/or solubilising agent(s). Examples of suitable binders include, but are not limited to, starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose, and/or polyethylene glycol. Examples of suitable lubricants include, but are not limited to, sodium oleate, sodium stearate, magnesium stearate, sodium benzoate, sodium acetate, and/or sodium chloride. Preservatives, stabilizers, dyes, antioxidants, suspending agents and/or flavoring agents may also be comprised in the pharmaceutical composition. Examples of preservatives include, but are not limited to, sodium benzoate, sorbic acid, and/or esters of p-hydroxybenzoic acid.

The pharmaceutical composition contemplated by the present invention may be formulated and/or administered in various ways well known to the skilled person. Preferably, the pharmaceutical composition of the present invention is in liquid form, e.g. in form of a solution such as an injection solution. Said solution may be injected, e.g. intramuscular or parenteral. The mode of administration, the dose, and the number of administrations of the pharmaceutical composition can be optimized by the skilled person in a known manner.

In a seventh aspect, the present invention further relates to a vaccine comprising a MVA virus according to the first aspect or a genome according to the second aspect.

As mentioned above, the (mutated) MVA virus according to the first aspect is highly host-restricted and, thus, highly attenuated. It is, therefore, an ideal vaccine to treat a wide range of recipients. The terms "host-restricted", "highly attenuated", "recipient", and "vaccine" are defined above. Preferably the recipients are primates, more preferably humans. In this respect, it should be noted that the MVA virus itself may be the vaccine. It confers protection against pox. However, said virus or said genome may further comprise a heterologous nucleic acid sequence, e.g. a sequence coding for an antigen, particularly an epitope of an antigen, against which a protective immunity, particularly an additional protective immunity, in the recipient may be elicited. The term "heterologous nucleic acid sequence" is defined above. Examples of such antigens cover, e.g. proteins of other viruses such as the Influenza virus, Hepatitis virus, e.g. Hepatitis C virus, Human immunodeficiency virus (HIV), Flavivirus, Paramyxovirus, Hantavirus or Filovirus, or proteins that are associated with the development of tumours and cancer such as Her2/neu or MUC-1. Examples of such epitopes cover, e.g. epitopes from proteins derived from other viruses such as the Influenza virus, Hepatitis virus, e.g. Hepatitis C virus, Human immunodeficiency virus (HIV), Flavivirus, Paramyxovirus, Hantavirus or Filovirus, or epitopes derived from proteins that are associated with the development of tumours and cancer such as extracellular peptides of Her2/neu or MUC-1. A MVA virus comprising a heterologous nucleic acid sequence can also be designated as recombinant MVA virus. After the administration of the vaccine into the body of the recipient, the antigens, particularly epitopes, are expressed and are presented to the immune system and a specific immune response against said antigens, particularly epitopes, may be induced. The recipient is, thus, immunized against said antigens, particularly epitopes.

Preferably, the vaccine comprising a MVA virus according to the first aspect or a genome according to the second aspect is a pox virus, an Influenza virus, a Hepatitis virus, e.g. a Hepatitis C virus, a Human immunodeficiency virus (HIV), a Flavivirus, a Paramyxovirus, a Hantavirus, and/or a Filovirus vaccine. It may also be used in vaccination against breast cancer, melanoma, pancreatic cancer or prostate cancer.

The vaccine contemplated by the present invention may be formulated and administered in various ways well known to the skilled person. Preferably, the vaccine of the present invention is in liquid form, e.g. in form of a solution such as an injection solution. Said solution may be injected, e.g. intramuscular or parenteral. The mode of administration, the dose, and the number of administrations of the vaccine can be optimized by the skilled person in a known manner. For the formulation or preparation of the vaccine, the MVA virus, particularly the recombinant MVA virus, according to the first aspect is converted into a physiologically acceptable form. This can be done based on the experience in the preparation of poxvirus vaccines used for vaccination against pox (as described by (Stickl et al. 1974 in Dtsch Med Wochenschr 99, 2386-2392)). Said vaccine is particularly useful to induce immune responses in immuno-compromised recipients such as primates including humans. The term "immuno-compromised", as used herein, describes the status of the immune system of a recipient, which shows only incomplete immune responses or has a reduced efficiency in the defense against infectious agents.

In an eight aspect, the present invention relates to a MVA virus according to the first aspect or a genome according to the second aspect for use in medicine. Preferably, the MVA virus according to the first aspect or the genome according to the second aspect is for use in vaccination and/or therapy. Particularly, the recipient is challenged with the MVA virus according to the first aspect or with the genome according to the second aspect to induce a specific immunity. Preferably the recipients are primates, more preferably humans. Said primates such as humans may be immuno-compromised. In this respect, it should be noted that the MVA virus itself may be the vaccine. It confers protection against pox. However, said virus or said genome may further comprise a heterologous nucleic acid sequence, e.g. a sequence coding for an antigen, particularly an epitope of an antigen, against which a protective immunity, particularly an additional protective immunity, in the recipient may be elicited. The terms "vaccination", "recipient", "heterologous nucleic acid sequence" are defined above. Preferred antigens, particularly epitopes, are described in the first and seventh aspect of the present invention. Preferably, said MVA virus or genome is for use in vaccination against pox virus, Influenza virus, Hepatitis virus, e.g. Hepatitis C virus, Human immunodeficiency virus (HIV), Flavivirus, Paramyxovirus, Hantavirus, Filovirus, tumours and/or cancer such as breast cancer, melanoma, pancreatic cancer or prostate cancer.

Alternatively or additionally, the recipient is challenged with the MVA virus according to the first aspect or with the genome according to the second aspect to elicit a therapeutic effect. As mentioned above, the heterologous sequence comprised in said virus or genome may code for a therapeutic compound. For example, the therapeutic compound can be a compound that affects or participates in tissue growth, cell growth, cell differentiation, a compound that is able to invoke a biological action such as an immune response, or a compound that can play any other role in one or more biological processes. Particularly, said compound may be an anti-microbial compound, an anti-viral compound, an anti-fungal compound, an immunosuppressive compound, a growth factor, an enzyme, an anti-inflammatory compound, or an anti-allergic compound. The therapeutic compound may also be an antisense nucleic acid.

The mode of vaccination, the vaccination dose, and the vaccination number can be optimized by the skilled person in a known manner. The vaccine may be formulated and administered in various ways well known to the skilled person. Preferably, the vaccine is administered in liquid form. Preferably, the vaccine is injected, e.g. intramuscular or parenteral. It is preferred that the MVA virus according to the first aspect or the genome according to the second aspect is administered at a pharmaceutically effective amount to the recipient. The term "pharmaceutically effective amount" refers to an amount of MVA virus or genome that is effective in a particular route of administration to elicit an immune response.

In a ninth aspect, the present invention relates to a MVA virus comprising a nucleic acid sequence, wherein the A3L gene and/or A9L gene is functionally deleted. Preferably, the A34R gene is further functionally deleted.

More preferably,
(i) the A3L gene and the A9L gene are functionally deleted,
(ii) the A3L gene and the A34R gene are functionally deleted,
(iii) the A9L gene and the A34R gene are functionally deleted, or
(iv) the A3L gene, the A9L gene, and the A34R gene are functionally deleted.

The (non-deleted) A3L gene may have a nucleic acid sequence according to SEQ ID NO: 7, the (non-deleted) A34R gene may have a nucleic acid sequence according to SEQ ID NO: 8, and/or the (non-deleted) A9L gene may have a nucleic acid sequence according to SEQ ID NO: 9. Further, the MVA virus may comprise a nucleic acid sequence prior to deletion according to accession number AY603355 (version AY603355.1 and GI:47088326).

In the context of the present invention, the term "functionally deletion" of the above mentioned A3L, A9L, and/or A34R gene(s) is to be understood that the gene(s) is (are) deleted to such an extent that the biological activity of the respective A3L, A9L, and/or A34R gene product(s) is reduced, preferably abolished, or is modified. For example, the biological activity may be reduced by at least 10, 20, 30, 40, 50, 60, 70, 80, 90, 100, 150 or 200% compared to (a) biological active (non-deleted) A3L, A9L, and/or A34R gene product(s).

Such a functionally deletion may be accomplished by partially deleting the A3L, A9L, and/or A34R gene(s), by completely deleting the A3L, A9L, and/or A34R gene(s), and/or by introducing one or more stop codon(s) into the A3L, A9L, and/or A34R gene(s).

The reduction or disappearance of the biological activity of the respective A3L, A9L, and/or A34R gene product(s) compared to (a) biological active (non-deleted) A3L, A9L, and/or A34R gene product(s) can be tested with a variety of experiments known to the skilled person. One way of detecting the reduction or disappearance of the biological activity of the respective A3L, A9L, and/or A34R gene product(s) compared to (a) biological active (non-deleted) A3L, A9L, and/or A34R gene product(s) is the conduction of a comet assay as described in Example 6. For the comet assay, a cell monolayer of adherent permissive cells is infected with a suitably low number of virus such as 0.01 to 0.001 virus per host cell. Progeny derived from a virus deleted in the A3L, A9L, and/or A34R gene(s) will not escape the initially infected cell and will cause small and confined circular plaques (a neighbouring collection of cells exhibiting cytopathic effect) or will not cause any plaques at all. A virus equipped with active A3L, A9L, and/or A34R gene products will cause plaques clearly visible also to the unaided eye; the plaques will expand within 2-7 days and eventually completely consume the cell monolayer.

Regarding the description of the gene products of the A3L gene, A9L gene and A34R gene, it is referred to the first aspect of the present invention.

Preferably, the MVA virus is an isolated MVA virus. The term "isolated MVA virus", as used herein, refers to a virus that is removed from its native or culturing environment. Thus, an isolated MVA virus may be free of some or all cellular components, i.e. components of the cells in which the virus naturally occurs or in which it is cultured (e.g. cytoplasmic or membrane components). It may also be free of some or all culturing components (e.g. culture medium or culture-related impurities such as culture-remnants).

The isolated MVA virus may further be purified. Thus, more preferably, the MVA virus is a purified MVA virus. The term "purified MVA virus", as used herein, refers to a virus that has been isolated under conditions that reduce or eliminate the presence of unrelated materials, i.e. contaminants, including native materials, e.g. cellular debris, cellular remnants, cellular proteins, cellular DNA molecules, and/or cellular RNA molecules, from which the virus is obtained. The purified MVA virus is preferably substantially free of cell and/or culture components. As used herein, the term "substantially free" is used operationally, in the context of analytical testing of the material. A purified MVA virus which is substantially free of contaminants is preferably at least 50% pure, more preferably at least 90% pure, and even more preferably at least 99% or 100% pure. Purity can be evaluated by chromatography, gel electrophoresis, immunoassay, composition analysis, biological assay, and other methods known in the art.

It is further preferred that the functionally deleted gene(s) is (are) replaced by a heterologous nucleic acid sequence. For example, the functionally deleted A3L gene is replaced by a heterologous nucleic acid sequence, the functionally deleted A9L gene is replaced by a heterologous nucleic acid sequence, and/or the functionally deleted A34R gene is replaced by a heterologous nucleic acid sequence. Methods how to insert heterologous nucleic acid sequences into the MVA virus genome are known to a skilled person. The expression of the heterologous nucleic acid sequence may be under the transcriptional control of a MVA virus promoter.

The term "heterologous nucleic acid sequence" is defined above. Preferably, the heterologous nucleic acid sequence is selected from a sequence coding for an antigen, particularly an epitope of an antigen, a diagnostic compound, or a therapeutic compound.

The antigen or epitope may be useful as a vaccine to induce an immune response against said antigen or epitope. Examples of such antigens which are heterologous to said virus cover, e.g. proteins of other viruses such as the Influenza virus, Hepatitis virus, e.g. Hepatitis C virus, Human immunodeficiency virus (HIV), Flavivirus, Paramyxovirus, Hantavirus or Filovirus, or proteins that are associated with the development of tumours and cancer such as Her2/neu or MUC-1. Examples of such epitopes which are heterologous to said virus cover, e.g. epitopes from proteins derived from other viruses such as the Influenza virus, Hepatitis virus, e.g. Hepatitis C virus, Human immunodeficiency virus (HIV), Flavivirus, Paramyxovirus, Hantavirus or Filovirus, or epitopes derived from proteins that are associated with the development of tumours and cancer such as extracellular peptides of Her/2 or MUC-1.

The therapeutic compound may be any compound with a therapeutic effect. For example, the therapeutic compound can be a compound that affects or participates in tissue growth, cell growth, cell differentiation, a compound that is able to invoke a biological action such as an immune response, or a compound that can play any other role in one or more biological processes. Particularly, said compound may be an anti-microbial compound, an anti-viral compound, an anti-fungal compound, an immunosuppressive compound, a growth factor, an enzyme, an anti-inflammatory compound, or an anti-allergic compound. The therapeutic compound may also be an antisense nucleic acid.

The diagnostic compound may be any compound with a diagnostic effect. For example, the therapeutic compound can be a marker/reporter protein such as an antibody, GFP, EGFP, β-Galactosidase, or an antibiotic resistance conferring protein such as bla (beta-lactamase) against ampicillin or npt (neomycin phosphotransferase) against neomycin or G418. Said marker/reporter protein may be used to identify or isolate the virus, e.g. by using hybridization technology, fluorescence microscopy, or ELISA assays. In addition, the antibiotic resistance conferring protein comprised in the virus confers resistance against antibiotic selection to the infected cell.

In preferred embodiments of the present invention, the virus comprises an A3L gene product, an A9L gene product, and/or an A34R gene product, wherein the gene product(s) preferably comprise(s) an/at least one amino acid sequence modification (e.g. 1, 2, 3, 4, 5, 6, 7, 8, or 9 amino acid sequence modification(s)). In one embodiment of the present invention, the virus comprises an A3L gene product, wherein the gene product comprises an/at least one amino acid modification (e.g. 1, 2, or 3 amino acid modification(s)). In another embodiment of the present invention, the virus comprises an A9L gene product, wherein the gene product comprises an/at least one amino acid modification (e.g. 1, 2, or 3 amino acid modification(s)). In a further embodiment of the present invention, the virus comprises an A34R gene product, wherein the gene product comprises an/at least one amino acid modification (e.g. 1, 2, or 3 amino acid modification(s)).

In a more preferred embodiment of the present invention, the virus comprises (i) an A9L gene product, wherein the gene product comprises an/at least one amino acid modification (e.g. 1, 2, or 3 amino acid modification(s)) and an A34R gene product, wherein the gene product, comprises an/at least one amino acid modification (e.g. 1, 2, or 3 amino acid modification(s)), (ii) an A9L gene product, wherein the gene product comprises an/at least one amino acid modification (e.g. 1, 2, or 3 amino acid modification(s)) and an A3L gene product, wherein the gene product comprises an/at least one amino acid modification (e.g. 1, 2, or 3 amino acid modification(s)), (iii) an A34R gene product, wherein the gene product comprises an/at least one amino acid modification (e.g. 1, 2, or 3 amino acid modification(s)) and A3L gene product, wherein the gene product comprises an/at least one amino acid modification (e.g. 1, 2, or 3 amino acid modification(s)), or (iv) an A9L gene product, wherein the gene product comprises an/at least one amino acid modification (e.g. 1, 2, or 3 amino acid modification(s)), an A34R gene product, wherein the gene product comprises an/at least one amino acid modification (e.g. 1, 2, or 3 amino acid modification(s)) and an A3L gene product, wherein the gene product comprises an/at least one amino acid modification (e.g. 1, 2, or 3 amino acid modification(s)).

Said amino acid sequence modification(s) (e.g. 1, 2, 3, 4, 5, 6, 7, 8, or 9 amino acid modification(s)) may be (an) amino acid deletion(s) (e.g. 1, 2, 3, 4, 5, 6, 7, 8, or 9 amino acid deletion(s)), amino acid insertion(s) (e.g. 1, 2, 3, 4, 5, 6, 7, 8, or 9 amino acid insertion(s)), amino acid addition(s) (e.g. 1, 2, 3, 4, 5, 6, 7, 8, or 9 amino acid additions(s)) and/or amino acid replacement(s) (e.g. 1, 2, 3, 4, 5, 6, 7, 8, or 9 amino acid replacement(s)). An "amino acid replacement" may also be designated herein as an "amino acid substitution". The term "amino acid insertion", as used herein, refers to an amino acid modification which takes place within the amino acid sequence of the A3L, A34R, and/or A9L gene product(s), while the term "amino acid addition", as used herein, refers to an amino acid modification which takes place at the N- or C-terminus of the A3L, A34R, and/or A9L gene product(s). As to the preferred embodiments of the amino acid modifications, it is referred to the first aspect of the present invention.

In a tenth aspect, the present invention relates to a cell comprising an A3L gene, A9L gene, and/or A34R gene of a MVA virus and expressing said gene(s).

It is preferred that the cell comprises (i) an A3L gene and an A9L gene,
(ii) an A3L gene and an A34R gene,
(iii) an A9L gene and an A34R gene, or
(iv) an A3L gene, an A9L gene, and an A34R gene.

Said cell may also be designated as recombinant cell. Particularly, said genes are isolated from the MVA virus/MVA virus genome, i.e. said genes are not comprised in/part of the MVA virus/MVA virus genome.

Said cell may be transfected with the A3L gene, A9L gene, and/or A34R gene of the MVA virus. The A3L gene, A9L gene, and/or A34R gene of the MVA virus may be stably maintained or transiently present in said cell. Preferably, the A3L gene, A9L gene, and/or A34R gene of the MVA virus is (are) stably maintained in said cell.

The A3L gene may have a nucleic acid sequence according to SEQ ID NO: 7, the A34R gene may have a nucleic acid sequence according to SEQ ID NO: 8, and/or the A9L gene may have a nucleic acid sequence according to SEQ ID NO: 9.

It is preferred that the cell further comprises a MVA virus according to the ninth aspect. Said cell is capable of providing in trans the gene product(s) (i.e. the A3L, A9L, and/or A34R gene product(s)) of the functionally deleted gene(s) (i.e. the A3L, A9L, and/or A34R genes (s)) of the MVA virus according to the ninth aspect. For example, (i) if the A3L gene is functionally deleted in the MVA virus according to the ninth aspect, the cell comprising the A3L gene and expressing said gene is capable of providing in trans the A3L gene product, (ii) if the A9L gene is functionally deleted in the MVA virus according to the ninth aspect, the cell comprising the A9L gene and expressing said gene is capable of providing in trans the A9L gene product, and/or (iii) if the A34R gene is functionally deleted in the MVA virus according to the ninth aspect, the cell comprising the A34R gene and expressing said gene is capable of providing in trans the A34R gene product.

The A3L gene product may have an amino acid sequence according to SEQ ID NO: 1, the A34R gene product may have an amino acid sequence according to SEQ ID NO: 2, and/or the A9L gene product may have an amino acid sequence according to SEQ ID NO: 3.

It is further preferred that
(i) the A3L gene of the MVA virus comprises at least one mutation (e.g. 1, 2, or 3 mutation(s)) resulting in an/at least one amino acid sequence modification (e.g. 1, 2, or 3 amino acid sequence modification(s)) of the gene product,
(ii) the A9L gene of the MVA virus comprises at least one mutation (e.g. 1, 2, or 3 mutation(s)) resulting in an amino acid sequence modification (e.g. 1, 2, or 3 amino acid sequence modification(s)) of the gene product, and/or
(iii) the A34R gene of the MVA virus comprises at least one mutation (e.g. 1, 2, or 3 mutation(s)) resulting in an amino acid sequence modification (e.g. 1, 2, or 3 amino acid sequence modification(s)) of the gene product.

Said amino acid sequence modification(s) (e.g. 1, 2, 3, 4, 5, 6, 7, 8, or 9 amino acid modification(s)) may be (an) amino acid deletion(s) (e.g. 1, 2, 3, 4, 5, 6, 7, 8, or 9 amino acid deletion(s)), amino acid insertion(s) (e.g. 1, 2, 3, 4, 5, 6, 7, 8, or 9 amino acid insertion(s)), amino acid addition(s) (e.g. 1, 2, 3, 4, 5, 6, 7, 8, or 9 amino acid additions(s)) and/or amino acid replacement(s) (e.g. 1, 2, 3, 4, 5, 6, 7, 8, or 9 amino acid replacement(s)). As to the preferred embodiments of the amino acid modifications, it is referred to the first aspect of the present invention.

Thus, said cell is not only capable of providing in trans the gene product(s) (i.e. the A3L gene product, A9L gene product, and/or A34R gene product) of the functionally deleted gene(s) (i.e. the A3L gene, A9L gene, and/or A34R gene) of the MVA virus according to the ninth aspect (see above). It is also (alternatively) capable of providing in trans gene product(s) having an/at least one amino acid sequence modification (i.e. the A3L gene product, wherein the gene product comprises an/at least one amino acid modification (e.g. 1, 2, or 3 amino acid modification(s)), A9L gene product, wherein the gene product comprises an/at least one amino acid modification (e.g. 1, 2, or 3 amino acid modification(s)), and/or A34R gene product, wherein the gene product comprises an/at least one amino acid modification (e.g. 1, 2, or 3 amino acid modification(s)) of the functionally deleted gene(s) (i.e. the A3L gene, A9L gene, and/or A34R gene) of the MVA virus according to the ninth aspect. Accordingly, said cell is for producing a (non-mutated) MVA virus comprising an A3L gene product, an A9L gene product, and/or an A34R gene product not having amino acid sequence modification(s) or for producing a (mutated) MVA virus comprising an A3L gene product, an A9L gene product, and/or an A34R gene product having amino acid sequence modification(s). As to the preferred embodiments of the amino acid modifications, it is referred to the first aspect of the present invention.

Said cell may be a mammalian cell such as a human or primate cell, or an avian cell. Said avian cell is preferably a chicken, quail, goose, or duck cell (e.g. a duck somite or duck retina cell). Said avian cell (e.g. chicken, quail, goose, or duck cell such as duck somite or duck retina cell) may be a primary cell (or a cell from a primary cell culture), a secondary cell (or a cell from a secondary cell culture), or an immortalized cell (or a cell from a cell line). As to the definition of the terms "primary cell", "primary cell culture", "secondary cell", "secondary cell culture", "immortalized cell", or "immortalized cell culture", it is referred to the first aspect of the present invention. In preferred embodiments of the present invention, the cell is from a CR or CR.pIX cell line. The CR and CR.pIX cell lines are derived from immortalized Muscovy duck retina cells (Jordan, et al. 2009 in Vaccine 27, 748-756). The CR.pIX cell line has further stably integrated into its genome a gene encoding the Adenovirus pIX protein and expresses said gene. In other preferred embodiments of the invention, the cells are chicken embryo fibroblast (CEF) cells. Said cells are primary cells.

In an eleventh aspect, the present invention relates to a nucleic acid molecule comprising an A3L gene, A9L gene, and/or A34R gene of a MVA virus, wherein preferably said gene(s) is (are) operably linked to a heterologous nucleic acid sequence. In one embodiment of the present invention, the nucleic acid molecule comprises an A3L gene, wherein preferably said gene is operably linked to a heterologous nucleic acid sequence. In another embodiment of the present invention, the nucleic acid molecule comprises an A9L gene, wherein preferably said gene is operably linked to a heterologous nucleic acid sequence. In a further embodiment of the invention, the nucleic acid molecule comprises an A34R gene, wherein preferably said gene is operably linked to a heterologous nucleic acid sequence.

It is preferred that the nucleic acid molecule comprises
(i) an A3L gene, wherein preferably said gene is operably linked to a heterologous nucleic acid sequence, and an A9L gene, wherein preferably said gene is operably linked to a heterologous nucleic acid sequence,
(ii) an A3L gene, wherein preferably said gene is operably linked to a heterologous nucleic acid sequence, and an A34R gene, wherein preferably said gene is operably linked to a heterologous nucleic acid sequence,
(iii) an A9L gene, wherein preferably said gene is operably linked to a heterologous nucleic acid sequence, and an A34R gene, wherein preferably said gene is operably linked to a heterologous nucleic acid sequence, or
(iv) an A3L gene, wherein preferably said gene is operably linked to a heterologous nucleic acid sequence, an A9L gene, wherein preferably said gene is operably linked to a heterologous nucleic acid sequence, and an A34R gene, wherein preferably said gene is operably linked to a heterologous nucleic acid sequence.

The nucleic acid molecule may also be designated as recombinant nucleic acid molecule. Particularly, the above mentioned gene(s) are isolated from the MVA virus/MVA virus genome, i.e. said gene(s) are not comprised in/part of the MVA virus/MVA virus genome.

The A3L gene may have a nucleic acid sequence according to SEQ ID NO: 7, the A34R gene may have a nucleic acid sequence according to SEQ ID NO: 8, and/or the A9L gene may have a nucleic acid sequence according to SEQ ID NO: 9.

The term "operably linked" means that the A3L, A9L, or A34R gene is linked to the heterologous nucleic acid sequence in such a way that in-frame expression of a corresponding construct can be affected, e.g. by avoidance of frame-shifts or stop codons, or by separation of the heterologous nucleic acid via an internal ribosomal entry site that allows translation to initiate independence of the 5' cap structure of the mRNA. Such internal ribosomal entry sites are known in the art and can be derived, for example, from poliovirus or encephalomyocarditis virus genomic RNA.

The term "heterologous nucleic acid sequence" is defined above. Preferably, the heterologous nucleic acid sequence is selected from a sequence coding for an antigen, an epitope, a diagnostic compound, or a therapeutic compound. More preferably, the heterologous nucleic acid sequence is a sequence coding for a diagnostic compound. The diagnostic compound may be any compound with a diagnostic effect. For example, the therapeutic compound can be a marker/reporter protein such as an antibody, GFP, EGFP, β-Galactosidase, or an antibiotic resistance conferring protein such as bla (beta-lactamase) against ampicillin or npt (neomycin phosphotransferase) against neomycin or G418. Said marker/reporter protein may be used to identify or isolate the virus, e.g. by using hybridization technology, fluorescence microscopy, or ELISA assays. In addition, the antibiotic resistance conferring protein comprised in the virus confers resistance against antibiotic selection to the infected cell. As to the preferred embodiments of the antigen, epitope, or therapeutic compound, it is referred to the first aspect of the present invention.

Preferably,
(i) the A3L gene of the MVA virus comprises at least one mutation (e.g. 1, 2, or 3 mutation(s)) resulting in an/at least one amino acid sequence modification (e.g. 1, 2, or 3 amino acid sequence modification(s)) of the gene product,
(ii) the A9L gene of the MVA virus comprises at least one mutation (e.g. 1, 2, or 3 mutation(s)) resulting in an/at least one amino acid sequence modification (e.g. 1, 2, or 3 amino acid sequence modification(s)) of the gene product, and/or
(iii) the A34R gene of the MVA virus comprises at least one mutation (e.g. 1, 2, or 3 mutation(s)) resulting in an/at least one amino acid sequence modification (e.g. 1, 2, or 3 amino acid sequence modification(s)) of the gene product.

Said amino acid sequence modification(s) (e.g. 1, 2, 3, 4, 5, 6, 7, 8, or 9 amino acid modification(s)) may be (an) amino acid deletion(s) (e.g. 1, 2, 3, 4, 5, 6, 7, 8, or 9 amino acid deletion(s)), amino acid insertion(s) (e.g. 1, 2, 3, 4, 5, 6, 7, 8, or 9 amino acid insertion(s)), amino acid addition(s) (e.g. 1, 2, 3, 4, 5, 6, 7, 8, or 9 amino acid additions(s)) and/or amino acid replacement(s) (e.g. 1, 2, 3, 4, 5, 6, 7, 8, or 9 amino acid replacement(s)). As to the preferred embodiments of the amino acid modifications, it is referred to the first aspect of the present invention.

In a twelfth aspect, the present invention relates to a method for producing a recombinant MVA virus comprising the steps of:
(i) providing a cell,
(ii) introducing a MVA virus according to ninth aspect and a nucleic acid molecule according to the eleventh aspect into the cell, and
(iii) cultivating the cell under conditions allowing homologous recombination between the nucleic acid sequence of the MVA virus and the nucleic acid molecule thereby obtaining the recombinant MVA virus.

Said cell may be a mammalian cell such as a human or primate cell, or an avian cell. Said avian cell is preferably a chicken, quail, goose, or duck cell (e.g. a duck somite or duck retina cell). Said avian cell (e.g. chicken, quail, goose, or duck cell such as duck somite or duck retina cell) may be a primary cell (or a cell from a primary cell culture), a secondary cell (or a cell from a secondary cell culture), or an immortalized cell (or a cell from a cell line). As to the definition of the terms "primary cell", "primary cell culture", "secondary cell", "secondary cell culture", "immortalized cell", or "immortalized cell culture", it is referred to the first aspect of the present invention. In preferred embodiments of the present invention, the cell is from a CR or CR.pIX cell line. The CR and CR.pIX cell lines are derived from immortalized Muscovy duck retina cells (Jordan, et al. 2009 in Vaccine 27, 748-756). The CR.pIX cell line has further stably integrated into its genome a gene encoding the Adenovirus pIX protein and expresses said gene. In other preferred embodiments of the invention, the cells are chicken embryo fibroblast (CEF) cells. Said cells are primary cells.

Preferably, said cell is infected with the MVA virus according to the ninth aspect and/or said cell is transfected with the nucleic acid molecule according to the eleventh aspect. The skilled person is aware of conditions allowing homologous recombination between the nucleic acid sequence of the MVA virus and the nucleic acid molecule in order to obtain a recombinant MVA virus. In addition, the skilled person is aware of experimental test to evaluate whether the homologous recombination was successful.

Various modifications and variations of the invention will be apparent to those skilled in the art without departing from the scope of invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art in the relevant fields are intended to be covered by the present invention.

The following Figures and Examples are merely illustrative of the present invention and should not be construed to limit the scope of the invention as indicated by the appended claims in any way.

BRIEF DESCRIPTION OF THE FIGURES

FIG. 5: Macroscopic plaque phenotypes of MVA-A2 and MVA-CR19 in cell monolayers stained with crystal violet. Note appearance of comets in MVA-CR19 already 72 h post infection at a time where MVA-A2 infected CR cells appear dotted with circular plaques. 96 h post infection the culture is in fulminant CPE after infection with MVA-CR19 and the overall stain intensity therefore appears weaker due to extensive loss of cell mass. At this time point comets are visible also after infection with MVA-A2. An inverse relationship is visible in the mammalian R05T culture: plaques are prominent and shaped like comets 120 h post infection only after infection with parental MVA-A2. The MVA-CR19 isolate appears to be highly attenuated for this cell line. The left panel shows plaques as visible with the unaided eye (scale bar of 0.5 cm), the right panel shows cells after initial 40× magnification (scale bar of 100 µm).

Figure 3:
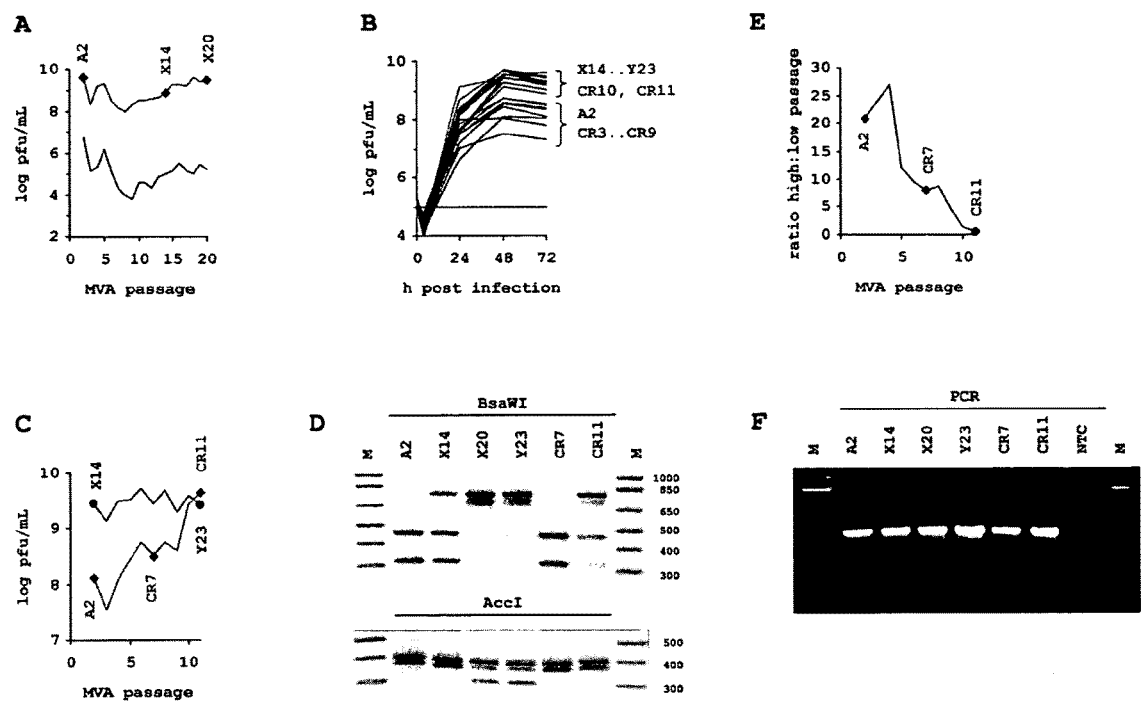
FIG. 3: Nomenclature of the different lineages added to data partially shown in FIG. 1. (A) Blind passage of MVA where concentration of input virus of the previous passage was not known. Intended MOI was 0.01 to 0.1 or $2 \times 10^4$ to $2 \times 10^5$ pfu/mL input virus at $2 \times 10^6$ cells/mL at the time of infection. In this experiment, MVA-A2 has been passaged into lineage MVA-X, leading to isolates MVA-X14 and MVA-X20. (B) Repeat of experiment shown in (A) with exception that each passage was initiated with defined MOI of 0.05, and that high and low passage MVA were always investigated in parallel: the low passage thread was started with MVA-A2, the reference high passage thread was started with MVA-X14. Note sudden increase in yields again starting with passage 10 of MVA demonstrating reproducibility. (C) Peak titers usually were obtained 48 h post infection. Only these yields are shown in this chart. Note constant yields in the reference passage of the individual experiments (within variation of the titration method, bold symbols) and gradual to sudden improvements in yields as passage number increases. In this controlled experiment MVA-A2 leads into lineage MVA-CR, and MVA-X14 leads into lineage MVA-Y. The genomic DNA of isolates MVA-A2, MVA-CR7 and MVA-CR11 were sequenced. (D) Genotype G256T in A34R is enriched by the inventors: note suddenly appearing and continuously accumulating resistance to BsaWI in MVA-X14, MVA-Y23 and MVA-CR11. The undigested PCR amplicons together with a non-template control is shown in (F). (E) Ratio of yields in high to low passage MVA 48 h post infection. Calculation was performed with data from panel (C). A ratio of 1 indicates similar properties and is observed for MVA of passage 10 to passage 23.

(C): No emergence of the D86Y A34R phenotype in MVA populations passaged on adherent cells. Compare to FIG. 3D for restriction fragment length polymorphism where the D86Y genotype in A34R accumulates. Maintenance of wild type sequence in the complete genes A3L, A9L and A34R was also confirmed by conventional sequencing, with the relevant region shown for MVA-B20 in FIG. 10.

Figure 10:
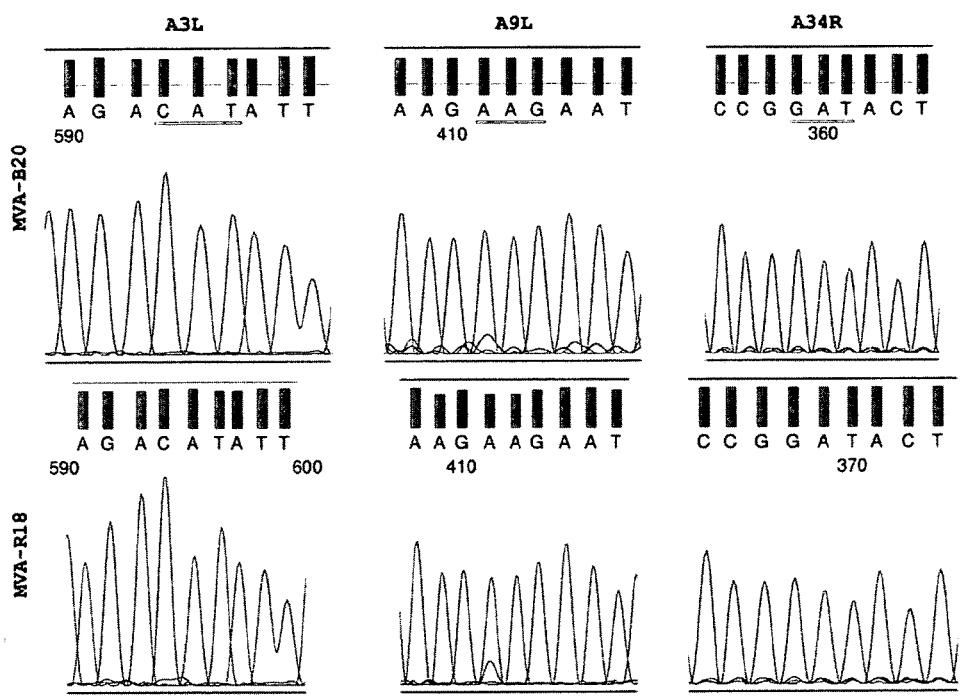

FIG. 10: Excellent specificity for the chemically-defined suspension environment. Sequence of the A3L C1915T, A9L A223G and A34R G256T region in strains MVA-B and MVA-R. The two lineages passaged on adherent cultures of duck or fruit bat origin maintain wild-type sequence without any signs at all of genotype changes in the here described open reading frames.

Figure 11:
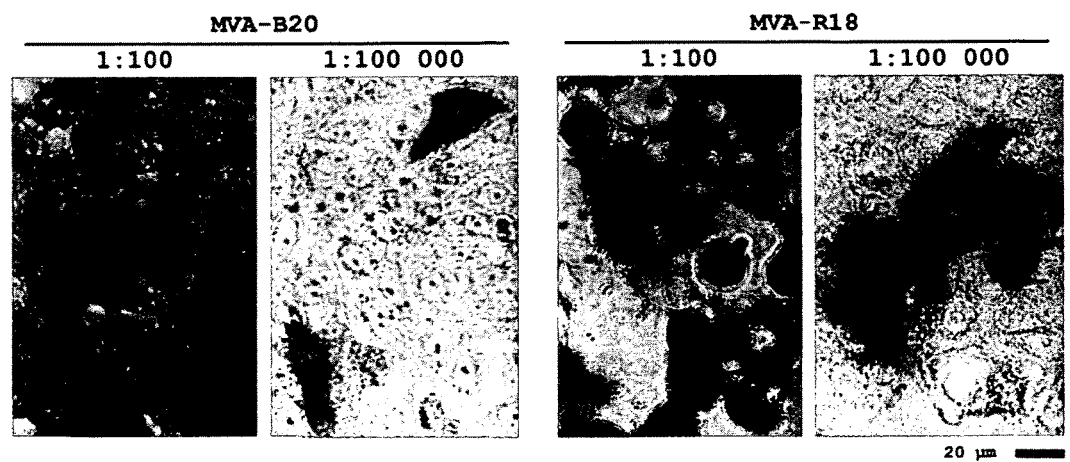

FIG. 11: Appearance of Vero cells after staining for microfocus assay. Foci are more prominent in titrations of MVA-R18 (virus strain or lineage obtained by passaging on cells from the Egyptian rousette) than MVA-B20 (obtained from the adherent Muscovy duck cell line) that was isolated in parallel. A newly gained limited replication in cells of primate origin indicates potential for greater immune stimulation as vaccine strain.

Figure 12:
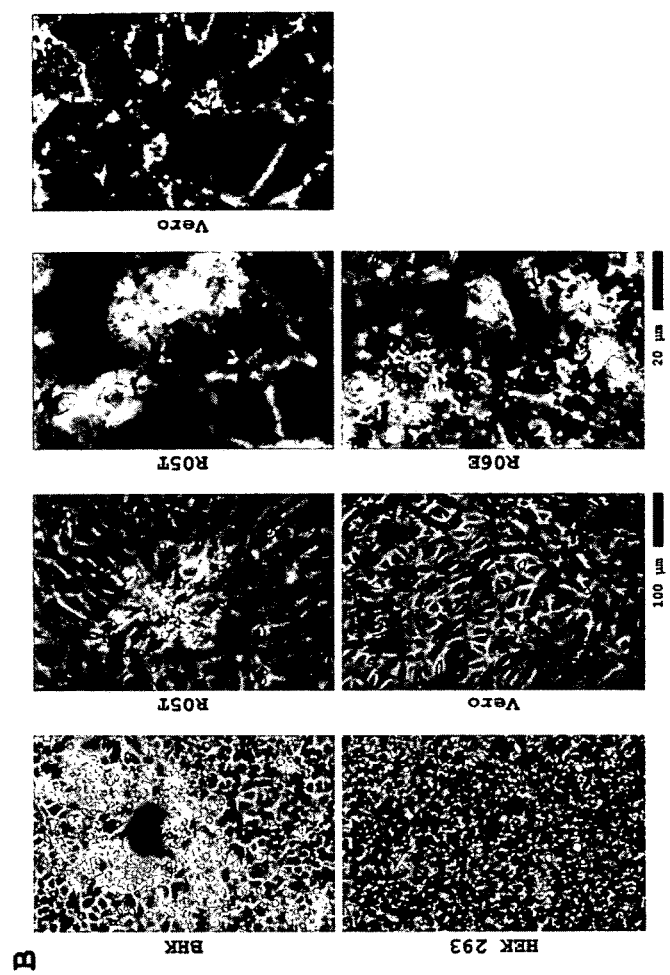

FIG. 12: Attenuation of MVA-CR isolates MVA-CR11 and MVA-CR19. Panel (A') shows replication properties of isolate MVA-CR11, again in an intermediate position to isolate MVA-CR19 shown in (A). Panel (B) shows examples of cytopathic effect (or absence of cytopathic effect) in infected non-avian cells caused by MVA-CR19. The images at 200-fold initial magnification (with scale bar of 20 µm) show cells at day 9 of the chart (A).

REFERENCES

[1] Zurbriggen, S., Tobler, K., Abril, C. et al. Isolation of sabin-like polioviruses from wastewater in a country using inactivated polio vaccine. *Appl Environ Microbiol* 2008, 74(18), 5608-5614.

[2] Kemper, A. R., Davis, M. M. & Freed, G. L. Expected adverse events in a mass smallpox vaccination campaign. *Eff Clin Pract* 2002, 5(2), 84-90.

[3] Parrino, J. & Graham, B. S. Smallpox vaccines: Past, present, and future. *J Allergy Clin Immunol* 2006, 118(6), 1320-1326.

[4] Excler, J. L., Parks, C. L., Ackland, J., Rees, H., Gust, I. D. & Koff, W. C. Replicating viral vectors as HIV vaccines: Summary report from the IAVI-sponsored satellite symposium at the AIDS vaccine 2009 conference. *Biologicals* 2010, 38(4), 511-521.

[5] Plotkin, S. A. Vaccines: the fourth century. *Clin Vaccine Immunol* 2009, 16(12), 1709-1719.

[6] Cebere, I., Dorrell, L., McShane, H. et al. Phase I clinical trial safety of DNA- and modified virus Ankara-vectored human immunodeficiency virus type 1 (HIV-1) vaccines administered alone and in a prime-boost regime to healthy HIV-1-uninfected volunteers. *Vaccine* 2006, 24(4), 417-425.

[7] Dorrell, L., Williams, P., Suttill, A. et al. Safety and tolerability of recombinant modified vaccinia virus Ankara expressing an HIV-1 gag/multiepitope immunogen (MVA.HIVA) in HIV-1-infected persons receiving combination antiretroviral therapy. *Vaccine* 2007, 25(17), 3277-3283.

[8] Gilbert, S. C., Moorthy, V. S., Andrews, L. et al. Synergistic DNA-MVA prime-boost vaccination regimes for malaria and tuberculosis. *Vaccine* 2006, 24(21), 4554-4561.

[9] Mayr, A. Smallpox vaccination and bioterrorism with pox viruses. *Comp Immunol Microbiol Infect Dis* 2003, 26 (5-6), 423-430.

[10] Webster, D. P., Dunachie, S., Vuola, J. M. et al. Enhanced T cell-mediated protection against malaria in human challenges by using the recombinant poxviruses FP9 and modified vaccinia virus Ankara. *Proc Natl Acad Sci USA* 2005, 102(13), 4836-4841.

[11] Drillien, R., Spehner, D. & Hanau, D. Modified vaccinia virus Ankara induces moderate activation of human dendritic cells. *J Gen Virol* 2004, 85 (Pt 8), 2167-2175.

[12] Liu, L., Chavan, R. & Feinberg, M. B. Dendritic cells are preferentially targeted among hematolymphocytes by Modified Vaccinia Virus Ankara and play a key role in the induction of virus-specific T cell responses in vivo. *BMC Immunol* 2008, 9, 15.

[13] Ryan, E. J., Harenberg, A. & Burdin, N. The Canarypox-virus vaccine vector ALVAC triggers the release of IFN-gamma by Natural Killer (NK) cells enhancing Th1 polarization. *Vaccine* 2007, 25(17), 3380-3390.

[14] Sutter, G. & Moss, B. Nonreplicating vaccinia vector efficiently expresses recombinant genes. *Proc Natl Acad Sci USA* 1992, 89(22), 10847-10851.

[15] Sutter, G., Wyatt, L. S., Foley, P. L., Bennink, J. R. & Moss, B. A recombinant vector derived from the host range-restricted and highly attenuated MVA strain of vaccinia virus stimulates protective immunity in mice to influenza virus. *Vaccine* 1994, 12(11), 1032-1040.

[16] Mayr, A. & Munz, E. [Changes in the vaccinia virus through continuing passages in chick embryo fibroblast cultures]. *Zentralbl Bakteriol Orig* 1964, 195(1), 24-35.

[17] Meyer, H., Sutter, G. & Mayr, A. Mapping of deletions in the genome of the highly attenuated vaccinia virus MVA and their influence on virulence. *J Gen Virol* 1991, 72 (Pt 5), 1031-1038.

[18] Sancho, M. C., Schleich, S., Griffiths, G. & Krijnse-Locker, J. The block in assembly of modified vaccinia virus Ankara in HeLa cells reveals new insights into vaccinia virus morphogenesis. *J Virol* 2002, 76(16), 8318-8334.

[19] Mayr, A. & Danner, K. Vaccination against pox diseases under immunosuppressive conditions. *Dev Biol Stand* 1978, 41, 225-234.

[20] Philipp, H. C. & Kolla, I. Laboratory host systems for extraneous agent testing in avian live virus vaccines: problems encountered. *Biologicals* 2010, 38(3), 350-351.

[21] Enserink, M. Influenza. Crisis underscores fragility of vaccine production system. *Science* 2004, 306(5695), 385.

[22] Jordan, I., Vos, A., Beilfuss, S., Neubert, A., Breul, S. & Sandig, V. An avian cell line designed for production of highly attenuated viruses. *Vaccine* 2009, 27(5), 748-756.

[23] Jordan, I., Northoff, S., Thiele, M. et al. A chemically defined production process for highly attenuated poxviruses. *Biologicals* 2011, 39(1), 50-58.

[24] Jordan, I., Horn, D., Oehmke, S., Leendertz, F. H. & Sandig, V. Cell lines from the Egyptian fruit bat are permissive for modified vaccinia Ankara. *Virus Res* 2009, 145(1), 54-62.

[25] Stickl, H., Hochstein-Mintzel, V., Mayr, A., Huber, H. C., Schafer, H. & Holzner, A. [MVA vaccination against smallpox: clinical tests with an attenuated live vaccinia virus strain (MVA) (author's transl)]. *Dtsch Med Wochenschr* 1974, 99(47), 2386-2392.

[26] Rosel, J. L., Earl, P. L., Weir, J. P. & Moss, B. Conserved TAAATG sequence at the transcriptional and translational initiation sites of vaccinia virus late genes deduced by structural and functional analysis of the HindIII H genome fragment. *J Virol* 1986, 60(2), 436-449.

[27] Byrd, C. M., Bolken, T. C. & Hruby, D. E. The vaccinia virus I7L gene product is the core protein proteinase. *J Virol* 2002, 76(17), 8973-8976.

[28] Heljasvaara, R., Rodriguez, D., Risco, C., Carrascosa, J. L., Esteban, M. & Rodriguez, J. R. The major core protein P4a (A10L gene) of vaccinia virus is essential for correct assembly of viral DNA into the nucleoprotein complex to form immature viral particles. *J Virol* 2001, 75(13), 5778-5795.

[29] Kato, S. E., Strahl, A. L., Moussatche, N. & Condit, R. C. Temperature-sensitive mutants in the vaccinia virus 4b virion structural protein assemble malformed, transcriptionally inactive intracellular mature virions. *Virology* 2004, 330(1), 127-146.

[30] Yeh, W. W., Moss, B. & Wolffe, E. J. The vaccinia virus A9L gene encodes a membrane protein required for an early step in virion morphogenesis. *J Virol* 2000, 74(20), 9701-9711.

[31] Husain, M., Weisberg, A. S. & Moss, B. Resistance of a vaccinia virus A34R deletion mutant to spontaneous rupture of the outer membrane of progeny virions on the surface of infected cells. *Virology* 2007, 366(2), 424-432.

[32] Blasco, R., Sisler, J. R. & Moss, B. Dissociation of progeny vaccinia virus from the cell membrane is regulated by a viral envelope glycoprotein: effect of a point mutation in the lectin homology domain of the A34R gene. *J Virol* 1993, 67(6), 3319-3325.

[33] Katz, E., Wolffe, E. & Moss, B. Identification of second-site mutations that enhance release and spread of vaccinia virus. *J Virol* 2002, 76(22), 11637-11644.

[34] Meiser, A., Boulanger, D., Sutter, G. & Krijnse Locker, J. Comparison of virus production in chicken embryo fibroblasts infected with the WR, IHD-J and MVA strains of vaccinia virus: IHD-J is most efficient in trans-Golgi network wrapping and extracellular enveloped virus release. *J Gen Virol* 2003, 84 (Pt 6), 1383-1392.

[35] van Belkum, A., Tassios, P. T., Dijkshoorn, L. et al. Guidelines for the validation and application of typing methods for use in bacterial epidemiology. *Clin Microbiol Infect* 2007, 13 Suppl 3, 1-46.

[36] Coulibaly, S., Bruhl, P., Mayrhofer, J., Schmid, K., Gerencer, M. & Falkner, F. G. The nonreplicating smallpox candidate vaccines defective vaccinia Lister (dVV-L) and modified vaccinia Ankara (MVA) elicit robust long-term protection. *Virology* 2005, 341(1), 91-101.

[37] Rotz, L. D., Dotson, D. A., Damon, I. K. & Becher, J. A. Vaccinia (smallpox) vaccine: recommendations of the Advisory Committee on Immunization Practices (ACIP), 2001. *MMWR Recomm Rep* 2001, 50 (RR-10), 1-25; quiz CE21-27.

[38] Hess, R. D., Weber, F., Watson, K. & Schmitt, S. Regulatory, biosafety and safety challenges for novel cells as substrates for human vaccines. *Vaccine* 2012, 30(17), 2715-2727.

[39] McIntosh, A. A. & Smith, G. L. Vaccinia virus glycoprotein A34R is required for infectivity of extracellular enveloped virus. *J Virol* 1996, 70(1), 272-281.

[40] Attramadal, A. The effect of divalent cations on cell adhesion in vitro. *J Periodontal Res* 1969, 4(2), 166.

[41] Jordan, I., Munster, V. J. & Sandig, V. Authentication of the R06E Fruit Bat Cell Line. *Viruses* 2012, 4(5), 889-900.

EXAMPLES

Example 1: Serial Isolates of MVA in Chemically Defined Suspension Cultures

In this example, we investigated properties of successive generations of MVA on a cell line already fully permissive for this virus. The selective environment is imposed by the chemically defined media and the absence of virion-stabilizing components such as abundant extracellular protein and lipids contained in the minimally purified lysate of embryonated eggs or bovine serum supplements commonly found in vertebrate cell cultures.

With the motivation to confirm stability expected from a DNA virus, we passaged MVA on the CR cell line. For the experiment, we used the MVA strain according to accession number AY603355 (version AY603355.1 and GI:47088326). The suspension culture and chemically defined procedure employed is fully within the constrains suggested by regulatory authorities and was developed and presented previously (Jordan, et al. 2011 in Biologicals 39, 50-58). Briefly described here, to produce hyperattenuated poxvirus to high titers, CR or CR.pIX suspension cultures in CD-U3 medium were allowed to proliferate to $4 \times 10^{\wedge}6$ cells/mL. One volume of CD-VP4 virus production medium was added and the culture inoculated with virus to a multiplicity of infection (MOI) as indicated, usually within 0.01 and 0.1. The CR and CR.pIX cell lines are derived from immortalized muscovy duck retina cells (Jordan, et al. 2009 in Vaccine 27, 748-756) and were designed for vaccine production. The CD-U3 medium (PAA, catalog #T1250, 3001) is an improved version of the CD-U2 cell proliferation medium, and CD-VP4 (Biochrom catalog #F9127) is a virus production medium developed to complement the proliferation medium during virus replication (Jordan, et al. 2011 in Biologicals 39, 50-58). All cultures described in the following examples were performed at 37° C. in an atmosphere enriched to 8% CO2. Suspension cultures were incubated in a shaking incubator (Infors) with 5 cm amplitude and 180 rpm for shake tubes and 150 rpm for shake flasks.

Samples were removed from the suspension cultures at defined intervals and infectious virus therein usually was released by sonication for 45 s with a Branson S250-D® a unit powering a 3.2 mm sonifier tip with 10% energy.

Number of infectious units were determined by adding serial dilutions of a virus preparation to 80% confluent Vero monolayers in DMEM:F12 medium (Gibco) containing 5% FCS. MVA cannot replicate in Vero cells so using such a substrate allows to strictly quantify only the input virus. After 48 hours, the cells were fixed with methanol and incubated with polyclonal vaccinia virus antibodies (Quartett Immunodiagnostika, Berlin, Germany) at 1:1000 dilution in PBS containing 1% fetal calf serum. Two wash steps were performed with PBS containing 0.05% Tween 20® and secondary antibody to the vaccinia-specific antibody is added at 1:1000. This secondary antibody is coupled to the peroxidase enzyme that catalyzes a color reaction upon incubation with AEC reagent (3-amino-9-ethyl-carbozole; 0.3 mg/ml in 0.1 M acetate buffer pH 5.0 containing 0.015% $H_2O2$). Infected foci are identified by light microscopy and plaque units/nil are calculated from the maximum dilution of MVA suspension that yields a positive dye reaction. All titrations were performed in parallel replicates (giving a total of four titration values per sample).

This is the first time that MVA, already adapted to proliferation in primary chicken cells, has been serially exposed to an immortal (rather than primary) culture that at the same time is an avian production substrate not derived from chicken. Furthermore, we have performed the passaging in chemically-defined culture medium without the addition of serum, albumin, or other components expected to stabilize viruses.

Figure 1:
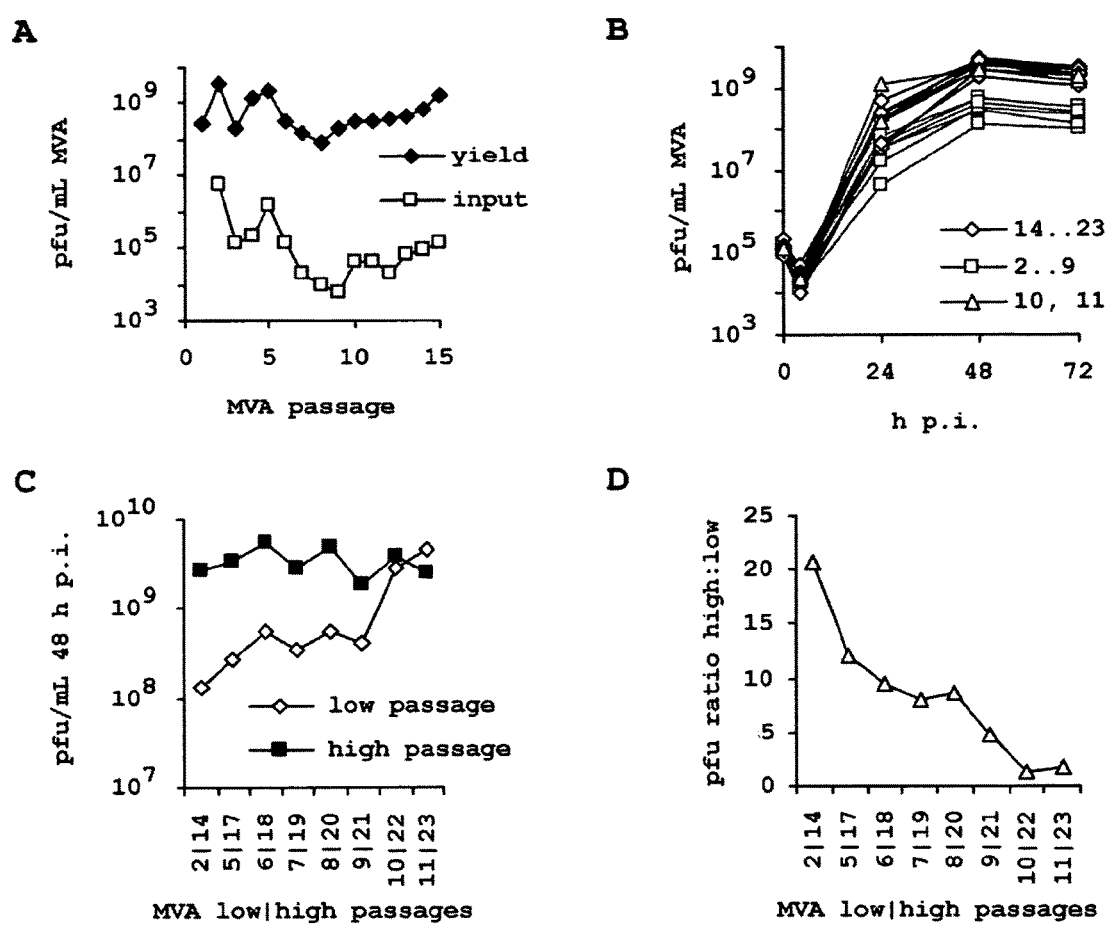
FIG. 1: (A) Blind passage of MVA where concentration of input virus of the previous passage was not known. Intended MOI was 0.01 to 0.1 or $2\times10^4$ to $2\times10^5$ pfu/mL input virus at $2\times10^6$ cells/mL at the time of infection. (B) Repeat of experiment shown in (A) with exception that each passage was initiated with defined MOI of 0.05, and that high and low passage MVA were always investigated in parallel. Note sudden increase in yields again starting with passage 10 of MVA demonstrating reproducibility. (C) Peak titers usually were obtained 48 h post infection. Only these yields are shown in this chart. Note constant yields in the reference passage of the individual experiments (within variation of the titration method, bold symbols) and gradual to sudden improvements in yields as passage number increases. (D) Ratio of yields in high to low passage MVA 48 h post infection. Calculation was performed with data from panel (C). A ratio of 1 indicates similar properties and is observed for MVA of passage 10 to passage 23.
Figure 2:
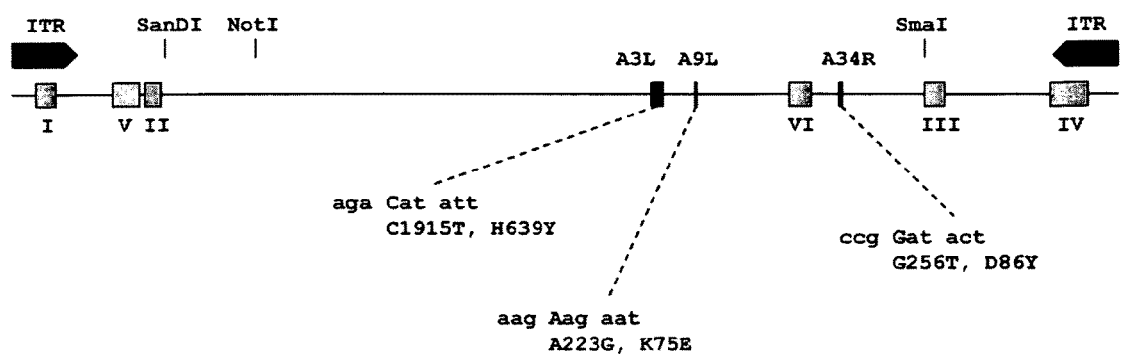
FIG. 2: Location of the here described mutations in the genome of chorioallantois vaccinia Ankara (CVA, Genbank entry AM501482), the parental virus of highly attenuated modified vaccinia Ankara (MVA). Shown are selected restriction enzyme sites for orientation, the inverted terminal repeats, and deletion sites (Meyer, et al. 1991 in J Gen Virol 72 (Pt 5), 1031-1038) (light boxes with roman numerals). The affected genes (A3L, A9L and A34R) are indicated with bold boxes. The dashed lines point to the associated sequence changes. Shown is the coding strand, the alphanumericals describe the mutation at DNA and amino acid level in the respective genes in strain MVA-CR.

As shown in FIG. 1A/3A, there is a gradual increase in yields with increasing passage. This initial experiment was performed such that virus yield from each immediately previous generation was estimated and with this estimate, we aimed to infect the subsequent culture with an MOI of 0.01 to 0.1. Because of the time required until titrations can be evaluated the true MOI varied from passage to passage and in our case (any passaging could also have an attenuating or dampening effect on virus replication) yields and MOI increased with increasing passage. After having discovered a surprising potential passage effect for MVA in a fully permissive cell line, we repeated the experiment under more stringent conditions.

The data shown in FIGS. 1B to 1C were obtained by adjusting MOI of each passage to 0.05 with virus isolated 48 h post infection of the respective previous passage. The penultimate passage 14 virus from the initial experiment of FIG. 1A/3A was used as high-passage reference. Any changes in MVA properties are, therefore, confirmed in this repeat experiment.

FIG. 1B shows the kinetics of the various passages superimposed. For each experiment, two independent parallel infections in independent duplicates were quantified starting with a low-passage and the high-passage MVA. At passage 10 and 11 of the thread initiated with low-passage virus we noticed a strong shift from (already high) yields in the range of 10^8 pfu/mL to beyond 10^9 pfu/mL.

To better visualize the effect, FIG. 1C depicts only the 48 h peak virus titers against passage numbers. MVA passages starting with passage 14 oscillate around 3.4×10^9 pfu/mL whereas MVA passages below 10 are in the range of 3.8×10^8 pfu/mL. Passage 10 and 11 virus suddenly replicates to a mean peak value of 3.66×10^9 pfu/mL. As determination of virus titers is associated with variations, FIG. 1D/3D depicts the ratios of low to high passage virus for each particular passage. As replication properties of high passage virus remain stable, this approach standardizes against titer deviations. A large number indicates an advantage of high passage virus, a ratio of 1 indicates that properties of low and high passage virus are highly similar or even identical.

The data in FIG. 1D show that with each generation yield of the lower passage virus approaches yield of high passage virus. Whereas 20-fold greater amount of high passage virus is being released at the onset of the experiment, this number decreases to parity after passage 10. In this particular experiment, an additional step towards high passage phenotype starts at passage 8. Stable ultra-high yield virus is obtained with passage 10, shown to be maintained in passage 11. Overall stability is demonstrated for over 8 passages starting with the independent reference lineage initiating with passage 14.

Example 2: Sequencing of MVA Genomic DNA

We next determined the DNA sequence of selected virus passages: 100 mL of AGE1.CR cultures at 2×10^6 cells/mL were infected with MVA at 0.01 MOI in a 1:1 mixture of CD-U3 and CD-VP4 media as described (Jordan, et al. 2011 in Biologicals 39, 50-58). 48 h post infection cells were removed by centrifugation with 200×g. Polyethylene glycol was added to 8% (from a 13% w/v stock solution in pure water) to the cleared supernatant. After incubation on ice for 30 min the suspension was centrifuged for 60 min with 6600×g and the translucent pellet containing viral particles was resuspended in 500 μL of PBS.

Extraviral DNA was digested with 8 units of Turbo DNase® (Ambion), then total DNA (predominately viral genome) was isolated with the DNA blood mini preparation kit (Qiagen®) and, both procedures according to the descriptions of the manufacturers.

To calculate expected yields: 178 kbp of MVA genome and 660 g/mol per DNA by correspond to 1.17×10^8 g of DNA per mol of virus. Divided by NA of 6.02×10^23 per mol this yields 1.95×10^(−16) g DNA per MVA particle. Assuming a yield of 10^8 pfu/mL, 1.95×10^(−8) g viral DNA/mL, or 19.5 ng/mL can be expected.

We obtained approx 8 μg total DNA in the preparations and performed multiplex qPCR to further estimate ratios of viral genomic DNA to cellular DNA. MVA levels were quantified with qPCR against the gene of membrane protein MVA128L of the intracellular mature virus, by 120811-120898 of GenBank #U94848, with CgTTTTgCATCATACCTCCATCTT (SEQ ID NO: 13), 6FAM-AggCATAAACgATTgCTgCTgTTCCTCTgT-BHQ1 (SEQ ID NO: 14), and gCgggTgCTggAgTgCTT (SEQ ID NO: 15). For detection of cellular DNA the E1A transgene was quantified with TgACTCCggTCCTTCTAACACA (SEQ ID NO: 16), YAK-CCCggTggTCCCgCTgTgC-BHQ1 (SEQ ID NO: 17), and TCACggCAACTggTTTAATgg (SEQ ID NO: 18). In a final reaction volume of 25 μL, 100 nM primers and 80 nM probes were mixed with dNTPs to 200 μM and Taq Man Universal® PCR Master Mix (#4324018, Applied Biosystems) to 1× concentration. Thermocycling was performed in a ABI Prism 7000 with 2 min at 50° C., 10 min at 95° C., and 40 cycles of 15 s at 95° C. and 1 min at 60° C. Typical Ct values were 16 for MVA and 33 for cellular DNA. Differences of Ct values indicate differences in relative molecule concentration so that ratio of viral to host DNA is 2^(33−16) or 130000:1, which is suitable for full genome sequencing.

Sequences were obtained with the Roche®/454 GS FLX+ technology. The genomic viral DNA of passages 2, 7, and 11 (shown in FIG. 1) were sequenced with 50-fold coverage for each genome and assembled using an unforced (without guide sequence) algorithm. Alignment of the three passages revealed extremely high sequence conservation as expected from pox viruses. A number of single-base deletions in nucleotide repeats most likely represent sequencing artefacts (for example tttttat-aaaataa versus tttttataaaaataa) and were not included in further analysis.

There were only three point mutations that fit the non-artefact definition and they were discovered in the examined passage 11 of the viral genome. All three point mutations were in coding regions, each affected a different structural protein, and each changed the amino acid composition. We consider these changes highly significant and completely unexpected. Thus, we have recovered a novel strain of MVA which we call MVA-CR in the remaining text.

The first of the three mutations discovered in MVA-CR is at by position 111561 of the CVA strain used here for orientation purposes (GeneBank #AM501482). This mutation is a C to T transition of nucleotide 1915 (abbreviated as C1915T) in the coding sequence of the gene called A3L according to one common poxvirus genomic notation (Meyer, et al. 1991 in J Gen Virol 72 (Pt 5), 1031-1038; Rosel et al. 1986 in J Virol 60, 436-449). The gene product is the major core protein P4b precursor. The C1915T mutation causes a change in the amino acid sequence from His (CAU) to Tyr (UAU) at codon 639. Note that the A3L gene is in antisense orientation in the poxvirus genome so that C1915T in the coding sequence corresponds to G111561A in the genomic DNA of CVA.

The second mutation is a A223G transition in the coding sequence of the 10.6 k virion membrane protein, encoded by A9L, a T119151C transition in the genome of CVA. The A223G mutation changes codon 75 from Lys (AAG) to Glu (GAG).

The third mutation is a G256T transversion in the coding sequence of the EEV membrane glycoprotein, encoded by A34R, a G144417T transversion in the genomic DNA of CVA. The G256T mutation changes codon 86 from Asp (GAT) to Tyr (UAU).

Location in the genome of MVA used in this experiment, accession number AY603355 (version AY603355.1 and GI:47088326): A3L, by 100334 to by 102268 on the complementary strand; A9L, by 107855 to by 108139 on the complementary strand; and A34R, 129078 . . . 129584 on the genomic strand. The strain used is the virus obtainable from the American Type Culture Collection (ATCC) under the number #VR-1508.

Figure 4A:
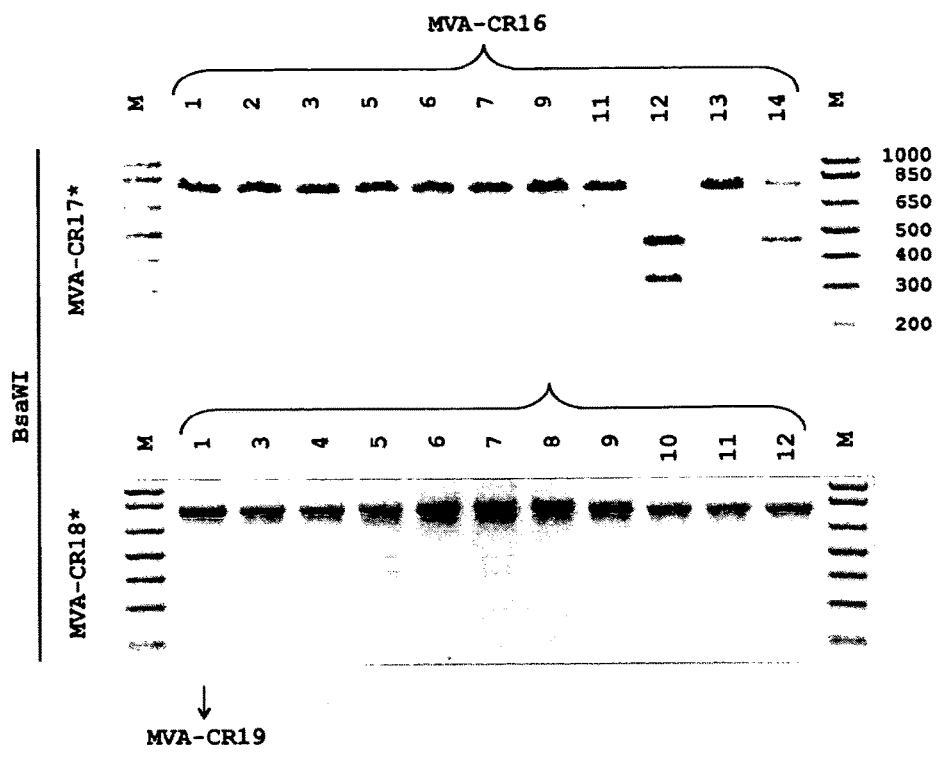
FIG. 4: MVA-CR is a novel strain and MVA-CR19 is a pure isolate of this strain. (A) Progress of plaque purification followed by diagnostic restriction enzyme digest. (B) Conventional sequencing chromatograms demonstrate that virus isolate MVA-CR19 has the novel pure genotype in all three genes A3L, A9L and A34R.
Figure 4A:
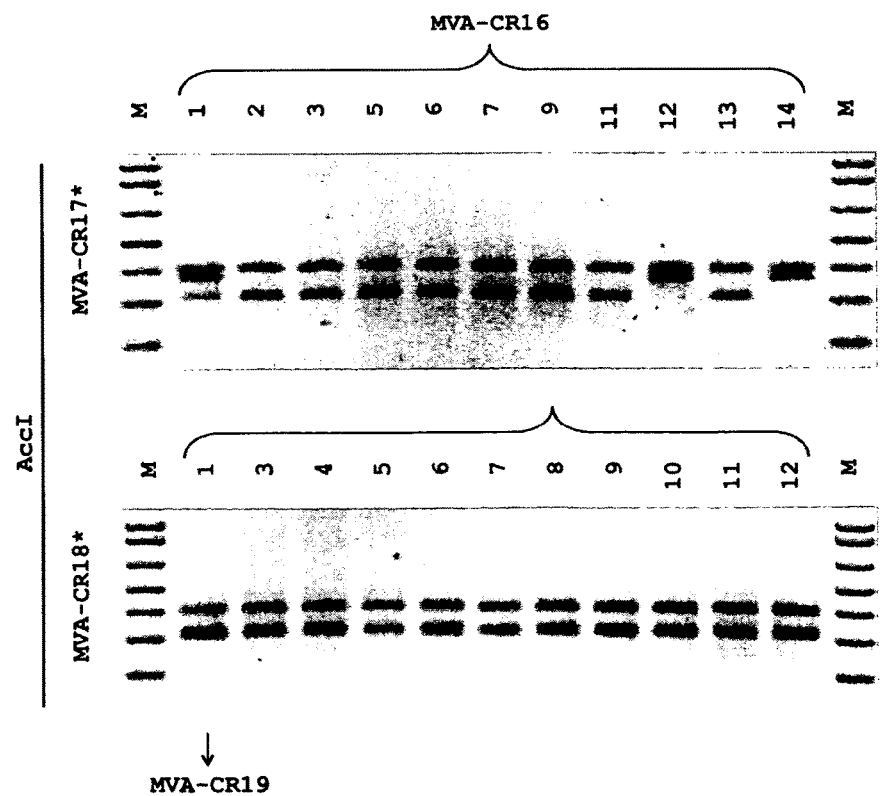
Figure 4B:
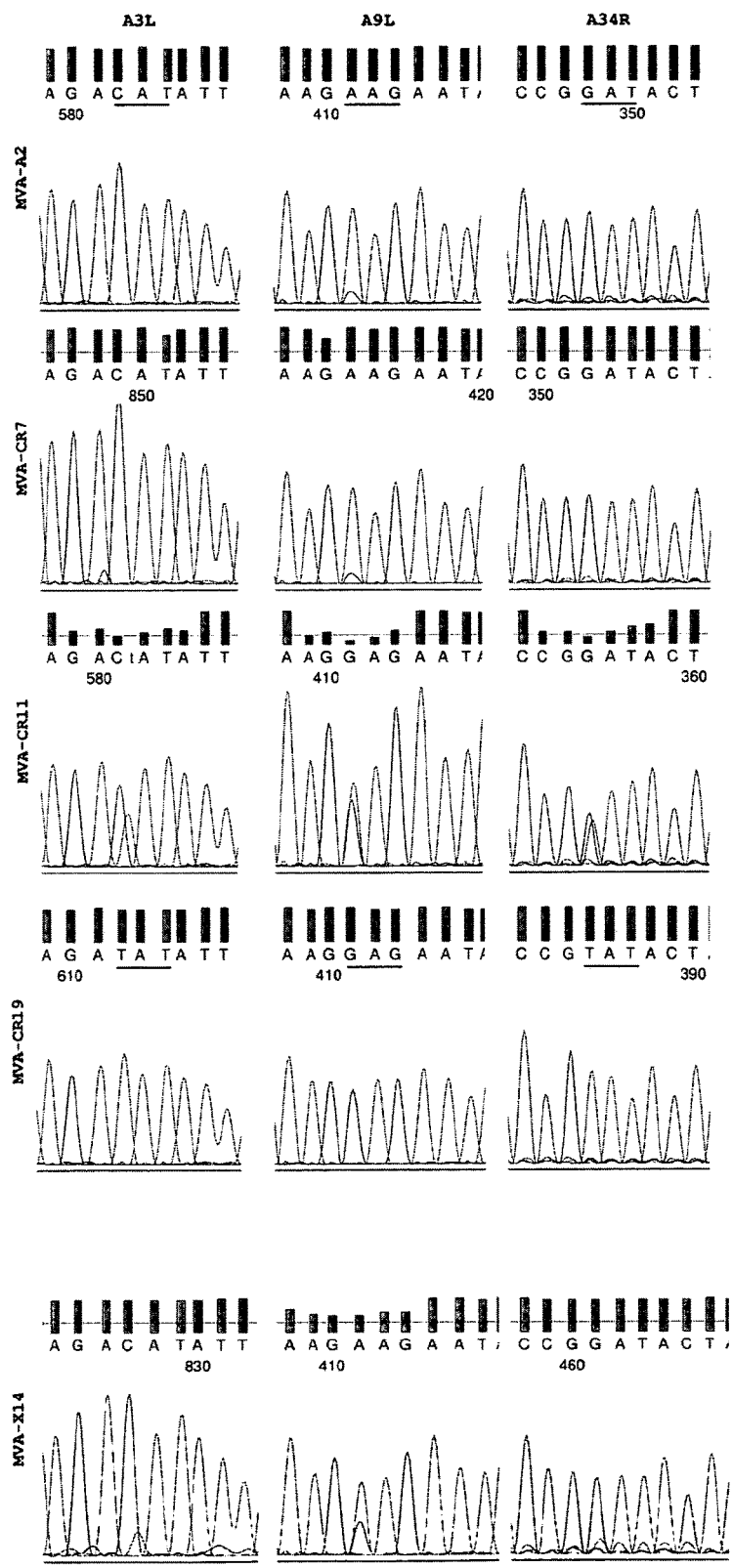

All three mutations affect proteins of MVA that are components of infectious particles. Functions of the affected proteins in greater detail are:

A3L gene product: The A3L gene product, P4b, is one of three major core proteins and processed by the I7L-encoded viral protease (Byrd et al. 2002 in J Virol 76, 8973-8976) during the maturation of the spherical and non-infectious immature virion (IV) to the intracellular mature virion (IMV). The P4b protein contributes to virion morphogenesis at a very early step. It is involved in the correct condensation and membrane rearrangements in the transition towards the infectious IMV (Heljasvaara et al. 2001 in J Virol 75, 5778-5795; Kato et al. 2004 in Virology 330, 127-146).

A9L gene product: This gene product, similar to P4b, is involved in the early steps of MVA maturation. It is a factor important for correct condensation of the core of the IMV (Yeh et al. 2000 in J Virol 74, 9701-9711).

A34R gene product: The extracellular enveloped virus (EEV) has evolved as a vehicle to allow virus to spread to distant sites. The additional membrane of the EEV is not equipped to mediate fusion with the target cell and must be disrupted to release the IMV, the actual infectious unit of vaccinia virus. Studies with A34R deletion mutants demonstrated that by destabilizing the EEV outer membrane, this factor is extremely important for infectious activity in the extracellular space and for spread of vaccinia virus (Husain et al. 2007 in Virology 366, 424-432). The A34R protein, together with the A33R and B5R proteins (Blasco et al. 1993 in J Virol 67, 3319-3325; Katz et al. 2002 in J Virol 76, 11637-11644; Meiser et al. 2003 in J Gen Virol 84, 1383-1392), modulates the rate at which the cell-associated enveloped virus (CEV) detaches from the producing cell.

A MVA virus with the above mutations has never been described before. Thus, passaging of MVA in chemically defined suspension cultures of a stable avian cell line improved the actual infectious entity, the mature virus, by changes in two integral proteins, the A3L and A9L gene products. These changes increase infectivity, improve maturation rates, and/or increase stability in such an environment that does not contain the expected stabilizing components of serum. In addition, a point mutation was detected in the A34R gene product that modulates properties of the extracellular form of the virus. This change increase detachment rates and decrease stability of the outer viral envelope that masks the infectivity of the mature particle.

Example 3: Confirmation Experiments

To preclude sequencing artifacts as explanation for our unexpected finding, we performed confirmation experiments. To confirm presence of MVA-CR in the preparation, we designed primers for amplification of all affected open reading frames for additional sequencing reactions. The PCR was performed with KOD HiFi® DNA polymerase (TOYOBO Novagen) 36 cycles of 20 s 55° C. annealing, 60 s 72° C. amplification (120 s for A3L), and 20 s 94° C. denaturation. The primers (f=forward and r=reverse) for amplification of the coding sequence of A9L were GCAAACGCGATAAGGATACG (a9lf) (SEQ ID NO: 19) and AAGCGGATGCAGAATAGACG (a9lr) (SEQ ID NO: 20), and of A34R were gCggAATCATCAACACTACCC (a34rf) (SEQ ID NO: 21) and TAATAACAAACgCg-gCgTCCATggC (a34rr) (SEQ ID NO: 22). Sequencing of the rather large A3L open reading frame was spanned with several primers: amplification was performed with GCA-GAAGAACACCGCTTAGG (a3lf) (SEQ ID NO: 23) and (a3lr) (SEQ ID NO: 24), sequencing was performed with TGAGAGCTCGCATCAATC (a3lf2) (SEQ ID NO: 25), ATCGGACTGTCGGATGTTGTG (a3lf3) (SEQ ID NO: 26), and CTAGAATCGGTGACCAACTC (a3lr3) (SEQ ID NO: 27).

Serendipitously, mutation D86Y in A34R introduces a target site for the AccI restriction enzyme: from ccggatact to ccG/TATACt (bold face for the mutation, uppercase letters for the restriction target site). At the same time, the BsaWI site of the wildtype is lost by the mutation D86Y, from agA/CCGGAt to agaccgtat. Digestion of the 772 bp A34R amplicon with AccI yields 399 and 373 bp for the parental MVA, and 399, 316 and 57 bp for MVA-CR. Conversely, digestion with BsaWI yields 452 and 320 bp for parental MVA and the full 772 bp for MVA-CR. The fragments were separated by 3% agarose gel electrophoresis in TAE buffer.

FIG. 3D shows that the D86Y mutation in A34R is part of the MVA-CR11 population. It was also independently obtained in the X14 lineages. This result confirms that the here discovered mutation is not a chance event but connected to the environment in effect during virus replication.

We also confirmed these surprising results by conventional sequencing of the amplified fragments. Because sequencing intentionally was performed directly on the purified PCR reactions without subcloning, the chromatograms shown in FIG. 4 are expected to reflect the average sequence, i.e. not merely the most abundant sequence but also presence of sequence variations. Purification of the PCR reaction was performed by resolving the PCR products by agarose gel electrophoresis, excision of the gel slice containing the single prominent signal, and isolation of the DNA mixture therein using the QIAquick Gel Extraction® kit (Qiagen®) according to the instructions of the manufacturer. Sequencing was performed with the same primers used also for amplification.

We confirmed the presence of all three observed mutations in MVA-CR11 and in the independent X14 lineage.

Example 4: Isolation and Purification of the Novel MVA-CR Strain

To obtain a pure MVA-CR virus, we next performed plaque purification: 1×10ˆ6 adherent CR cells were seeded per well of a 6-well plate in DMEM:F12 medium containing 5% FCS (Biochrom). After 24 h, only 10ˆ4 total pfu of MVA-CR16 was added, that is, a descendant of MVA-CR11 that had been passaged for additional 5 generations in chemically defined CR suspension cultures. To infect with low number of infectious units allows one to obtain well separated plaques. After 30 min, the culture medium was replaced with 0.8% of low-gelling agarose (Sigma #A9045) in DMEM:F12 medium containing 5% FCS. The agarose overlay prevents diffusion of progeny virus released by the infected monolayer so that individual plaques are not cross contaminated. The overlay also allows isolation of progeny virus by recovery of small (approximately 2 mm diameter) agarose cores with a hollow needle. Such agarose cores were picked from foci of cytopathic effect and transferred to a fresh adherent cell monolayer at 80% of maximum confluency in 12-well plates, each agarose core into a separate well. Virus diffuses out of the agarose core, infects the cells in the well, and virus obtained by this procedure is considered purified as it is (in theory) derived from a single initial plaque. However, some viruses tend to aggregate, a problem also encountered with poxviruses, so that a particular host culture may become infected with a mixture of viruses. As shown in FIG. 4, isolate #9 of this preparation removed by 17 generations from MVA-A2 (hence termed MVA-CR17*, with an asterisk to denote plaque purification as additional manipulation) is considered pure and was chosen for further plaque purification. The second round gave the desired A34R genotypes. Isolate #1 of this second round was chosen and amplified in chemically defined CR cultures. The A3L, A9L and A34R genes were sequenced directly out of PCR without any subcloning of the fragments and revealed a novel, pure and unique population.

In summary, by repeated isolation of virus derived from a chemically defined process on an immortal cell line, we obtained and further purified a novel vaccinia virus strain, with strain according to microbiological definition meaning "the descendants of a single isolation in pure culture [ . . . ] that can be distinguished from other isolates [ . . . ] by phenotypic and genotypic characteristics" (van Belkum et al. 2007 in Clin Microbiol Infect 13 Suppl 3, 1-46). We called this strain MVA-CR. The first fully purified, tangible member of this strain is MVA-CR19, and distinguishing features are at least one of the mutations selected from the group consisting of C1915T in A3L, A223G in A9L and G256T in A34R genes, all numbers referring to the coding strand.

Example 5: Properties of MVA-CR (Yield)

The yield of a preparation containing MVA-CR is greater by almost 10-fold compared to a population containing the parental strain. This is an extremely important property. Hyperattenuation of the MVA-based vaccines is an important safety feature but comes at the cost of dose requirement: $10^8$ infectious units of MVA per vaccination are estimated to be required for efficient stimulation of the immune system (Coulibaly et al. 2005 in Virology 341, 91-101; Gilbert, et al. 2006 in Vaccine 24, 4554-4561) and for global programs against infectious diseases hundreds of million of doses of the highly attenuated poxviruses may be required annually. For comparison, lesser attenuated strains with limited replication potential also produced on avian cells include vaccines against measles, mumps and yellow fever; these require only $10^3$ to $5.5 \times 10^4$ infectious units per dose (information from the package inserts of YF-VAX® from Sanofi Pasteur and M-M-R®II from Merck). The protective dose of the vaccinia strain Dryvax in routine vaccination against smallpox is $2.5 \times 10^5$ infectious units (Rotz et al. 2001 in MMWR Recomm Rep 50, 1-25; quiz CE21-27), 400 fold lower than the dose recommended for MVA-based vaccines. Hence, to reach all intended vaccinees, novel highly efficient and robust production systems for MVA-based vaccines will be required, and novel MVA strains are required to complement the technological advancements.

Example 6: Properties of MVA-CR (Escape from Host Cells)

Another, equally important property pertains to purity of the virus preparation. For any vaccine derived from a continuous cell line, purification of the preparation to deplete host cell derived components is required. With respect to residual DNA, a maximum level of 10 ng per dose (Hess et al. 2012 in Vaccine 30, 2715-2727) is considered acceptable. A considerable portion of conventional MVA is highly cell associated. The novel mutations which we have identified facilitate virus release and dissociation from the host cell. Destabilization of the external membrane of the EEV led to a greater fraction of actual infectious units of the virus (virions corresponding to the IMV) present in the extracellular volume.

Figure 5:
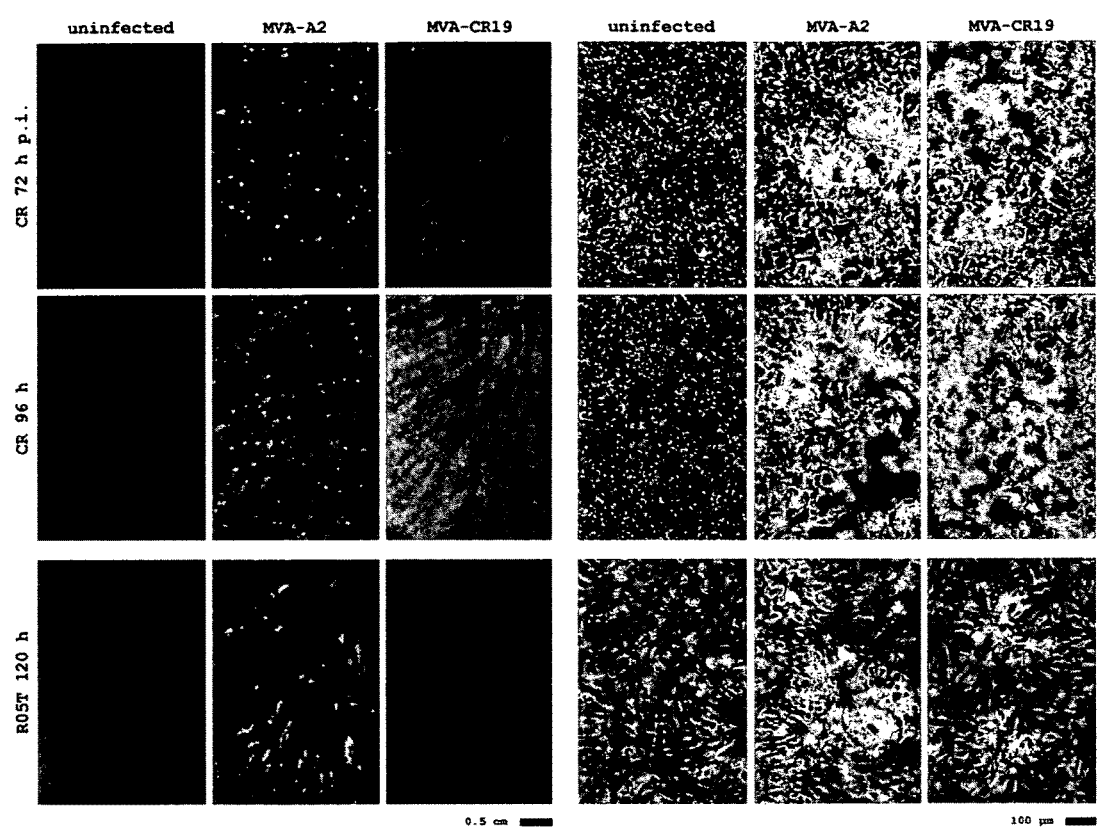

For confirmation purposes, a "comet assay" as described previously for the non-attenuated vaccinia viruses (McIntosh and Smith 1996 in J Virol 70, 272-281) was conducted. Such an assay visualizes the ability of a virus to escape the host cell: circular plaques indicate strong cell association, whereas elongated comet-like plaques suggest that progeny viruses dissociate from the host cell to initiate infection at more distant sites. In our experiments, $1 \times 10^6$ adherent CR or $1.5 \times 10^6$ R05T cells were seeded into a T25 flask. R05T is a cell line obtained by immortalization of primary cells from the Egyptian rousette. This is one of very few mammalian cell lines permissive for MVA (Jordan, et al. 2009 in Virus Res 145, 54-62) and serves as a reference in the here described experiments. After 24 h, 50000 pfu of MVA-A2 or MVA-CR19 were added. The flasks were put into an incubator and kept undisturbed for at least 72 h to ensure that released virus reinfects in the immediate vicinity so that it still can be associated with the primary plaque. The cell monolayer was fixed by addition of 0.2 volumes of 10% formaldehyde in PBS directly to the medium. As shown in FIG. 5, after staining with 0.05% crystal violet (Sigma) in water different plaque morphologies of MVA-A2 and MVA-CR19 are visible even by the unaided eye.

Figure 6:
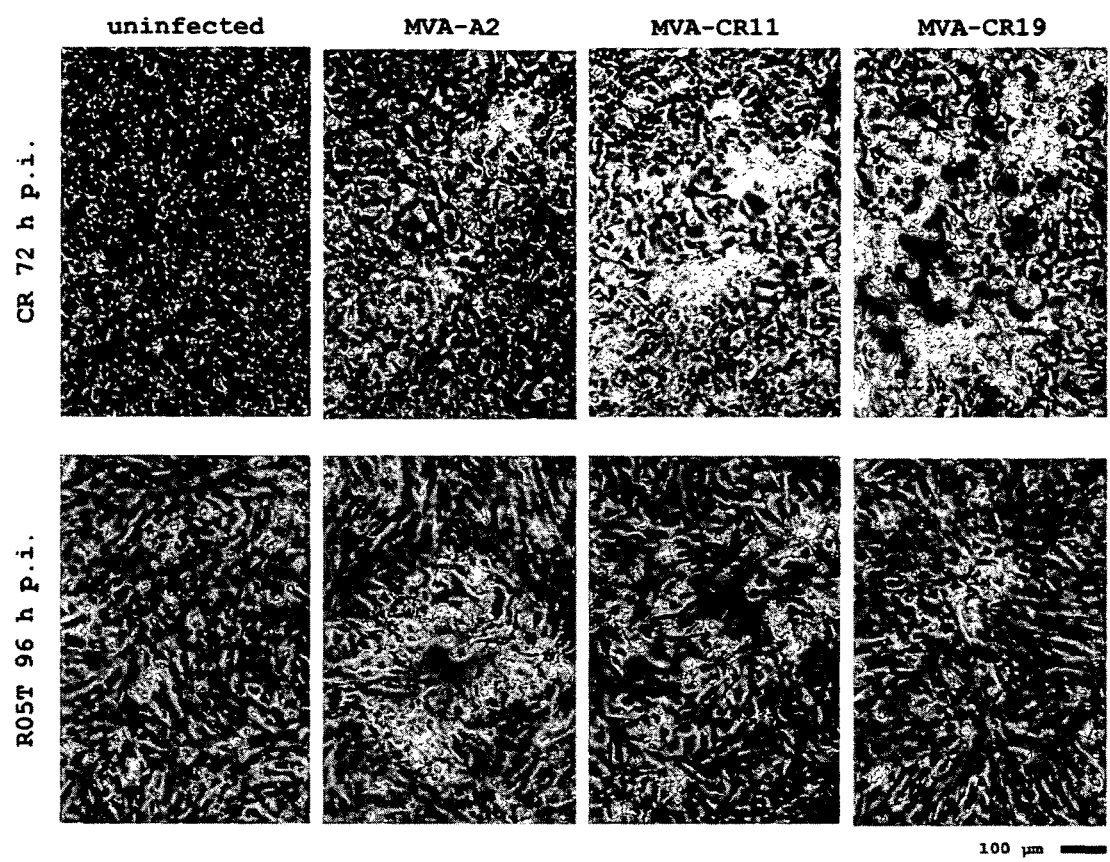
FIG. 6: Plaque phenotype at 40-fold initial magnification. Note that plaques are more pronounced in CR cells (top row) infected with MVA-CR19 compared to MVA-A2; plaque size caused by MVA-CR11 is intermediate as if the mutation excerpts a helper function already in a mixture of genotypes. The reverse situation was observed on R05T cells with MVA-CR19 appearing to be more attenuated than MVA-A2 (bottom row); again with MVA-CR11 in an intermediate position.

FIG. 6 shows typical plaques at 40× initial magnification in monolayers of CR and R05T cells infected with MVA-A2, MVA-CR11 or MVA-CR19. At this greater magnification, we more clearly observed the greater attenuation of MVA-CR19 on R05T and confirmed presence of the prominent plaques caused by MVA-CR19 in CR cells.

We next examined, whether plaque phenotype in adherent cultures is an indication of greater viral mobility also within chemically defined infected cell cultures. We, therefore, infected CR.pIX suspension cultures with isolates MVA-A2 and MVA-CR19 as described in example 1 but this time centrifuged samples for 5 min at 200×g to obtain a cell-free supernatant (abbreviated "SN"). The cell pellet was discarded and virus in the SN was subjected to three freeze/thaw cycles (−85° C./37° C.) to rupture the outer membrane of the EEV for increased infectivity.

Figure 7:
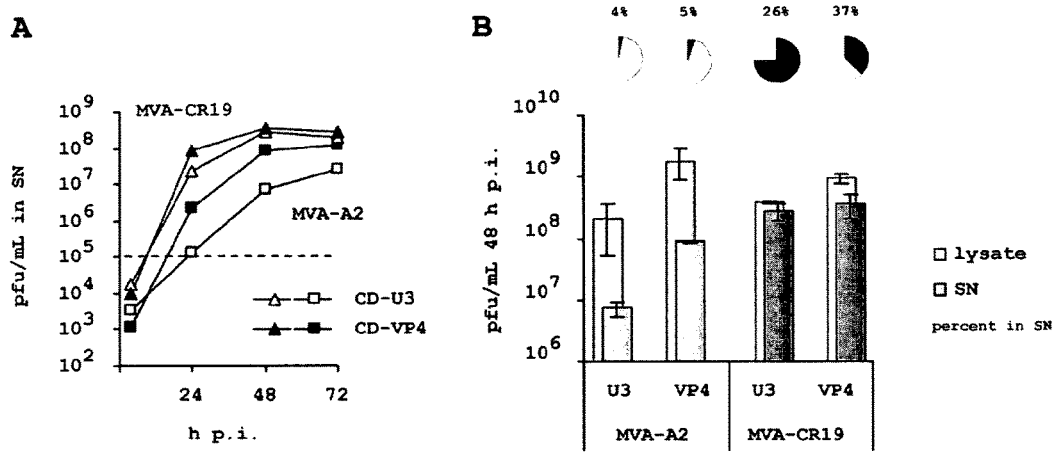
FIG. 7: Virus release from the CR producer cell in suspension cultures. A2 and CR19 refers to MVA isolate, CD-U3 and CD-VP4 refers to 1 volume of corresponding medium added for virus production, cell proliferation was always performed in CD-U3. (A) Kinetic of replication of isolates MVA-A2 and MVA-CR19 in cell proliferation medium with (bold symbols) or without (open symbols) addition of virus production medium. The dashed line at $10^5$ pfu/mL corresponds to input virus, MOI of 0.05. (B) Distribution of infectious units in supernatant or complete lysate (supernatant and cell-associated virus) 48 h post infection. Light columns indicate pfu/mL of the complete lysate, dark columns concentration of infectious units released into the cell supernatant. The pie charts on top of the columns refer to infectious units in cell free space (SN) in relation to complete lysate (LYS). The curves shown in (A) are the average of three independent parallel experiments, standard deviation is not shown to maintain clarity in a comparison of four independent curves. In (B) standard deviation of the three repeats is shown for the 48 h-values. The samples used to obtain these data points are from the kinetic of panel (A).

Furthermore, we tested virus replication also in a monophasic process only in CD-U3 cell proliferation medium without addition of CD-VP4 virus production medium. We have shown previously that a biphasic process where CD-VP4 is added at the time of infection increases yields of hyperattenuated poxviruses significantly (Jordan, et al. 2011 in Biologicals 39, 50-58). For this reason it was highly surprising that a comparison of replication kinetics as shown in FIG. 7A indicates that isolate MVA-CR19 replicates just as efficiently in the monophasic process as in the biphasic environment (gray curves). For MVA-A2, the expected at least 10-fold differences were confirmed (black curves, open symbols for the monophasic process).

Thus, we have obtained gain-of-function mutations that facilitate release of MVA from the host cell. This is confirmed in the data shown in FIG. 7 also when we compare infectious units in the supernatant (SN) and in the complete lysate. For the chart in panel B, 48 h post infection virus was assayed not only from SN but also from a sonicated lysate of the complete cell suspension. A greater percentage of infectious MVA-CR19 virus is in the cell-free compartment (74.0% in the monophasic process, 37.5% in the biphasic process) compared to MVA-A2 (3.6% and 4.9%, respectively).

Figure 8:
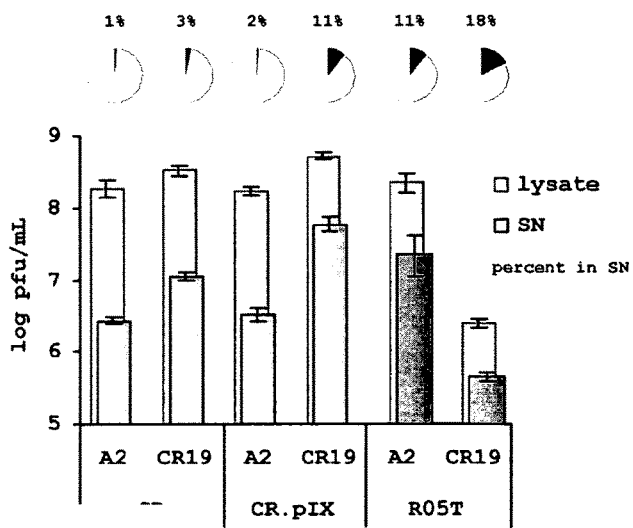
FIG. 8: Virus release from adherent producer cells cultivated in presence of serum. Light columns indicate pfu/mL of the complete lysate, dark columns concentration of infectious units released into the cell supernatant, and the pie charts on top of the columns the percentage of cell-free virus in the lysate. Cultures were assayed for MVA-A2 or MVA-CR19 48 h p.i. in infected CR or CR.pIX cells and 144 h p.i. in R05T cells.

The fact that more MVA-CR19 virus is trapped in host cells in presence of virus production medium is consistent with our intention of inducing cell aggregates to facilitate cell-to-cell spread of virus. This observation is also confirmed in adherent cultures shown in FIG. 8, where the release of MVA-CR19 compared to MVA-A2 is facilitated in all of the tested cultures, albeit with far less pronounced differences. As discussed earlier, the outer membrane of the EEV interferes with infectivity of MVA and one reason for increased extracellular infectivity of MVA-CR is due to the decreased stability of this component. Without agitation and in presence of virion-stabilizing fetal calf serum, this outer membrane of MVA-CR19 is retained for greater time intervals, levelling this potential advantage of MVA-CR19. Furthermore, concentrations of divalent cations are elevated in media designed for adherent cultures as these are known to promote cell adherence (Attramadal 1969 in J Periodontal Res 4, 166). Increased concentration of Mg2+ and Ca2+ probably also strengthens the association of virus envelopes to plasma membranes, again levelling any advantages that we observed for MVA-CR in chemically defined suspension cultures.

Thus, MVA-CR19 has gained an increased ability to escape the host cell. Completely unexpected and surprising, however, is the clear tendency that with increasing purity of the MVA-CR strain (that we have obtained with isolate MVA-CR19) attenuation in the R05T cell line appears to increase, manifested by small and fully confined foci in this cell line. The properties are extremely valuable: the novel MVA-CR strain remains highly attenuated and at the same time escapes more easily from the producer cell. An increase of the fraction of extracellular virus facilitates purification tremendously as cell-free supernatants instead of whole-cell lysates can be used as harvest bulk. Furthermore, true monophasic production processes are possible: MVA-CR can be produced to high titers in the same culture medium that is also used for cell proliferation. Except for addition of small volumes (less than 5 to 20% of the culture volume) of feed to provide glucose and other nutrients, or to regulate pH, no virus production medium is required anymore.

Example 7: Properties of MVA-CR (Specificity for the Chemically Defined Process)

To further characterize the selective pressures driving emergence of strain MVA-CR, we also isolated successive generations of MVA from adherent CR and R05T cell lines in an experiment that mirrors the initial experiment described in Example 1. The adherent CR cell line has been used to examine whether emergence of MVA-CR is also influenced by host cell characteristics in addition to culturing conditions. R05T as a mammalian, yet MVA-permissive cell line, serves as a reference, again testing specificity of the selection and stability of parental MVA.

Figure 9:
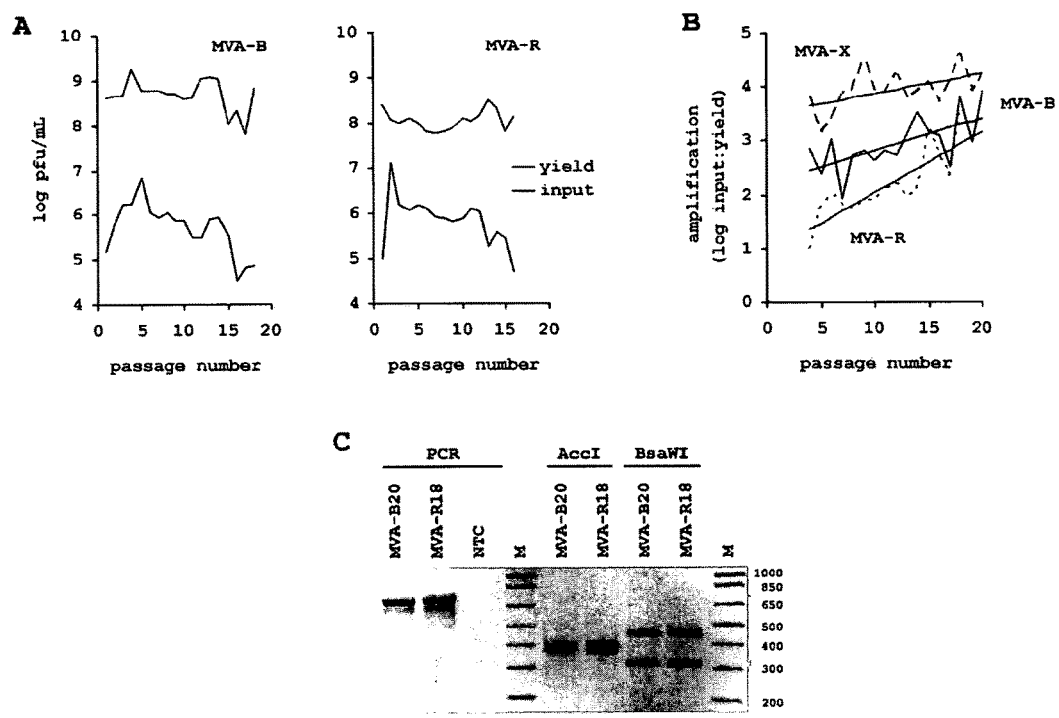
FIG. 9: Sequential generations of MVA on adherent serum-dependent CR cells and mammalian R05T cells. MVA-B is the lineage derived from adherent CR cells and MVA-R is the lineage derived from the R05T cells. (A) Sequential infection was performed without knowing the titer of the previous generation. The resulting fluctuations in input virus are shown in the lower (black) curve, the yield is shown in the upper curve. Units are log 10 of pfu/mL. (B) Dividing yield by input virus describes amplification of virus for each generation. MVA-X (broken upper curve) is the lineage that was derived from the chemically-defined suspension culture shown in FIG. 1. Higher generation numbers show greater amplification with peak value of 10000 infectious progeny viruses per pfu of input virus.

For this experiment, $1.5 \times 10^6$ CR.pIX and $1 \times 10^6$ R05T cells were seeded into T25 flasks for each generation. Infection was performed to an estimated MOI of 0.1. The actual input virus as determined by titration at later stages is shown in FIG. 9A. For the sequential virus generations, CR cultures with full cytopathic effect were recovered 48 h to 72 h post infection and R05T cultures between 72 h to 96 h. Virus was released from the lysate by sonication as described in example 1.

FIG. 9B depicts amplification of virus via ratio of input virus to released progeny virus for each generation obtained from suspension CR, adherent CR or adherent R05T cultures, respectively. Data for calculation of amplification in suspension is obtained from the first experiment described in example 1. Linear regression lines of the three experiments indicates that efficiency of virus replication increases with generation number suggesting some adaptation of MVA in all three systems. The effect appears to be greatest in the mammalian R05T cells, which are also farthest removed from the cognate chicken host of MVA.

However, truly surprising and an extremely strong confirmation of this study is the fact that although MVA is adapted to the serum-dependent cultures, the G256T genotype in A34R does not emerge and accumulate in any of these two systems. This is conclusively shown in panel C of FIG. 9, with the same method established in example 3.

The observations shown in FIG. 9C have been confirmed by sequencing of the A3L, A9L and A34R genes. As shown in FIG. 10, there are no indications at all that the novel MVA-CR genotype emerges or accumulates in the viruses passaged on adherent cell lines derived from duck or fruit bat.

Sequential increase of amplification rate is greatest for R05T-derived MVA. Furthermore, in determination of infectious units, we observed that MVA-R strain, for example MVA-R18 isolate shown in FIG. 11, produces a stronger signal and often foci involving more than one cell compared to MVA-B20 that was isolated in parallel (replication of MVA is faster in CR cells resulting in a lead of 2 generations at the end of the 12-weeks experiment). Foci involving several cells and stronger staining leads to the conclusion that replication is limited in the usually non-permissive Vero indicator cell line. MVA-R strain, as opposed to all of the CR-derived strains examined here (MVA-B, MVA-X, MVA-Y and MVA-CR proper) appears to be less attenuated in a mammalian system. Such a virus may have desirable properties other than strain MVA-CR: it may be more immunogenic due to limited replication at the site of infection and it may be extremely suitable as backbone for vectored vaccines in animals (especially chiropterans that are difficult to reach for rabies vaccination).

In summary, replication of MVA in a chemically defined suspension culture is the main driving force for emergence of MVA-CR. Usually, interactions of parasite (virus) and host shape a selective environment. However, here the artificial chemically-defined medium, the suspension culture, or the combination of both (which best meets the requirement for industrial production of a vaccine) clearly is the main driving force in the transformation of the initial wildtype MVA genotype towards MVA-CR.

Example 8: Properties of MVA-CR: Attenuation

Attenuation describes any loss of replication potential of a virus population compared to the parental population. Compared to vaccinia virus, MVA has lost the potential to replicate in most mammalian cells, especially in primate (including human) cells. This property is an important feature that allows application of MVA as vaccine vector also in immunocompromized human recipients.

To test whether attenuation of MVA-CR has been maintained, we infected adherent monolayers of CR, Vero and R05T cell lines with MVA-A2, MVA-CR11 and MVA-CR19. Cells were seeded with $5 \times 10^5$ (CR), $2 \times 10^5$ (R05T), and $1 \times 10^5$ (R06E and Vero), respectively, per well of a 6-well plate and MVA was added to an MOI of 0.1. Cell lysate was prepared by freezing the plates and sonicating a thawed lysate thereof at the indicated time points. All samples were stored at −85° C. and at the end of the experiment titered together in a microfocus assay on Vero cells as described above. The replication data in FIG. 12 confirms that strain MVA-CR is fully attenuated and does not replicate in Vero, replicates very slowly in R06E (also a cell line from the Egyptian rousette), moderately in R05T and with very high productivities CR cultures. A similar replication phenotype has been confirmed previously for MVA-A2 (Jordan et al. 2012 in Viruses 4, 889-900).

The invention claimed is:

1. A Modified Vaccinia Ankara (MVA) virus comprising a nucleic acid sequence encoding an A3L gene product and/or an A34R gene product, wherein said nucleic acid sequence comprises at least one mutation resulting in an amino acid sequence modification of said gene product(s);
   wherein the amino acid sequence modification is in a region spanning amino acid positions 634 to 644 of the A3L gene product according to SEQ ID NO: 1, or amino acid positions corresponding thereto, and/or
   wherein the amino acid sequence modification is in a region spanning amino acid positions 81 to 91 of the A34R gene product according to SEQ ID NO: 2, or amino acid positions corresponding thereto.

2. The MVA virus of claim 1, wherein the nucleic acid sequence further encodes an A9L gene product, wherein said nucleic acid sequence comprises at least one mutation resulting in an amino acid sequence modification of said gene product;
   wherein the amino acid sequence modification is in a region spanning amino acid positions 70 to 80 of the A9L gene product according to SEQ ID NO: 3, or amino acid positions corresponding thereto.

3. The MVA virus of claim 2, wherein
   (i) the virus comprises a nucleic acid sequence encoding an A3L gene product and an A9L gene product, wherein said nucleic acid sequence comprises at least one mutation resulting in an amino acid sequence modification of said gene products,
   wherein the amino acid sequence modification is in a region spanning amino acid positions 634 to 644 of the A3L gene product according to SEQ ID NO: 1, or amino acid positions corresponding thereto, and
   wherein the amino acid sequence modification is in a region spanning amino acid positions 70 to 80 of the A9L gene product according to SEQ ID NO: 3, or amino acid positions corresponding thereto; or (ii) the virus comprises a nucleic acid sequence encoding an A34R gene product and an A9L gene product, wherein said nucleic acid sequence comprises at least one mutation resulting in an amino acid sequence modification of said gene products,
wherein the amino acid sequence modification is in a region spanning amino acid positions 81 to 91 of the A34R gene product according to SEQ ID NO: 2, or amino acid positions corresponding thereto, and
wherein the amino acid sequence modification is in a region spanning amino acid positions 70 to 80 of the A9L gene product according to SEQ ID NO: 3, or amino acid positions corresponding thereto.

4. The MVA virus of claim 2, wherein the virus comprises a nucleic acid sequence encoding an A3L gene product, an A34R gene product and an A9L gene product, wherein said nucleic acid sequence comprise at least one mutation resulting in an amino acid sequence modification of said gene products;
wherein the amino acid sequence modification is in a region spanning amino acid positions 634 to 644 of the A3L gene product according to SEQ ID NO: 1, or amino acid positions corresponding thereto,
wherein the amino acid sequence modification is in a region spanning amino acid positions 81 to 91 of the A34R gene product according to SEQ ID NO: 2, or amino acid positions corresponding thereto, and
wherein the amino acid sequence modification is in a region spanning amino acid positions 70 to 80 of the A9L gene product according to SEQ ID NO: 3, or amino acid positions corresponding thereto.

5. The MVA virus of claim 2, wherein
(i) the amino acid sequence modification is at amino acid position 639 of the A3L gene product or at an amino acid position corresponding thereto,
(ii) the amino acid sequence modification is at amino acid position 638 of the A3L gene product or at an amino acid position corresponding thereto,
(iii) the amino acid sequence modification is at amino acid position 86 of the A34R gene product or at an amino acid position corresponding thereto,
(iv) the amino acid sequence modification is at amino acid position 75 of the A9L gene product or at an amino acid position corresponding thereto, and/or
(v) the amino acid sequence modification is at amino acid position 74 of the A9L gene product or at an amino acid position corresponding thereto.

6. The MVA virus of claim 5, wherein the amino acid sequence modification is an amino acid deletion or amino acid replacement, wherein
(i) H at amino acid position 639 of the A3L gene product or at an amino acid position corresponding thereto is deleted or replaced by a hydrophobic amino acid, preferably A, V, I, L, M, F, Y or W, a negative amino acid, preferably D or E, or a polar uncharged amino acid, preferably S, T, N or Q,
(ii) R at amino acid position 638 of the A3L gene product or at an amino acid position corresponding thereto is deleted or replaced by a hydrophobic amino acid, preferably A, V, I, L, M, F, Y or W, a negative amino acid, preferably D or E, or a polar uncharged amino acid, preferably S, T, N or Q,
(iii) D at amino acid position 86 of the A34R gene product or at an amino acid position corresponding thereto is deleted or replaced by a hydrophobic amino acid, preferably A, V, I, L, M, F, Y or W, a positive amino acid, preferably R, H or K, or a polar uncharged amino acid, preferably S, T, N or Q,
(iv) K at amino acid position 75 of the A9L gene product or at an amino acid position corresponding thereto which is deleted or replaced by a hydrophobic amino acid, preferably A, V, I, L, M, F, Y or W, a negative amino acid, preferably D or E, or a polar uncharged amino acid, preferably S, T, N or Q, and/or
(v) K at amino acid position 74 of the A9L gene product or at an amino acid position corresponding thereto which is deleted or replaced by a hydrophobic amino acid, preferably A, V, I, L, M, F, Y or W, a negative amino acid, preferably D or E, or a polar uncharged amino acid, preferably S, T, N or Q.

7. The MVA virus of claim 6, wherein the amino acid replacement is an amino acid replacement of
(i) H at amino acid position 639 of the A3L gene product or at an amino acid position corresponding thereto by Y (H639Y A3L gene product mutant),
(ii) R at amino acid position 638 of the A3L gene product or at an amino acid position corresponding thereto by Y (R638Y A3L gene product mutant),
(iii) D at amino acid position 86 of the A34R gene product or at an amino acid position corresponding thereto by Y (D86Y A34R gene product mutant),
(iv) K at amino acid position 75 of the A9L gene product or at an amino acid position corresponding thereto by E (K75E A9L gene product mutant), and/or
(v) K at amino acid position 74 of the A9L gene product or at an amino acid position corresponding thereto by E (K74E A9L gene product mutant).

8. The MVA virus of claim 7, wherein the amino acid replacement is an amino acid replacement of
(i) H at amino acid position 639 of the A3L gene product or at an amino acid position corresponding thereto by Y and D at amino acid position 86 of the A34R gene product or at an amino acid position corresponding thereto by Y (H639Y A3L/D86Y A34R gene product mutant),
(ii) H at amino acid position 639 of the A3L gene product or at an amino acid position corresponding thereto by Y and K at amino acid position 75 of the A9L gene product or at an amino acid position corresponding thereto by E (H639Y A3L/K75E A9L gene product mutant),
(iii) D at amino acid position 86 of the A34R gene product or at an amino acid position corresponding thereto by Y and K at amino acid position 75 of the A9L gene product or at an amino acid position corresponding thereto by E (D86Y A34R/K75E A9L gene product mutant), or
(iv) H at amino acid position 639 of the A3L gene product or at an amino acid position corresponding thereto by Y, D at amino acid position 86 of the A34R gene product or at an amino acid position corresponding thereto by Y, and K at amino acid position 75 of the A9L gene product or at an amino acid position corresponding thereto by E (H639Y A3L/D86Y A34R/K75E A9L gene product mutant).

9. The MVA virus of claim 7, wherein
(i) the A3L gene product with the H639Y mutation has an amino acid sequence according to SEQ ID NO: 4, wherein said variant comprises the amino acid Y at amino acid position 639 or at an amino acid position corresponding thereto,
(ii) the A34R gene product with the D86Y mutation has an amino acid sequence according to SEQ ID NO: 5, wherein said variant comprises the amino acid Y at amino acid position 86 or at an amino acid position corresponding thereto, and/or (iii) the A9L gene product with the K75E mutation has an amino acid sequence according to SEQ ID NO: 6 or is a variant thereof which is at least 95% identical to said amino acid sequence, wherein said variant comprises the amino acid E at amino acid position 75 or at an amino acid position corresponding thereto.

10. The MVA virus of claim 1, wherein the virus further comprises a heterologous nucleic acid sequence.

11. The MVA virus of claim 10, wherein the heterologous nucleic acid sequence is selected from a sequence coding for an antigen, particularly an epitope of an antigen, a diagnostic compound, or a therapeutic compound.

12. A genome of the MVA virus according to claim 1.

13. A cell comprising a MVA virus according to claim 1.

14. The cell of claim 13, wherein the cell is a non-adherent/suspension cell.

15. The cell of claim 13, wherein the cell is an avian cell.

16. A cell comprising a genome according to claim 12.

17. The cell of claim 14, wherein the cell is an avian cell.

* * * * *

```
                          SEQUENCE LISTING

<160> NUMBER OF SEQ ID NOS: 27

<210> SEQ ID NO 1
<211> LENGTH: 644
<212> TYPE: PRT
<213> ORGANISM: Vaccinia virus

<400> SEQUENCE: 1

Met Glu Ala Val Val Asn Ser Asp Val Phe Leu Thr Ser Asn Ala Gly
1               5                   10                  15

Leu Lys Ser Ser Tyr Thr Asn Gln Thr Leu Ser Leu Val Asp Glu Asp
            20                  25                  30

His Ile His Thr Ser Asp Lys Ser Leu Ser Cys Ser Val Cys Asn Ser
        35                  40                  45

Leu Ser Lys Ile Val Asp Asp Phe Ile Ser Ala Gly Ala Arg Asn
    50                  55                  60

Gln Arg Thr Lys Pro Lys Arg Ala Gly Asn Asn Gln Ser Gln Gln Pro
65                  70                  75                  80

Ile Lys Lys Asp Cys Met Val Ser Ile Asp Glu Val Ala Ser Thr His
                85                  90                  95

Asp Trp Ser Thr Arg Leu Arg Asn Asp Gly Asn Ala Ile Ala Lys Tyr
            100                 105                 110

Leu Thr Thr Asn Lys Tyr Asp Thr Ser Asn Phe Thr Ile Gln Asp Met
        115                 120                 125

Leu Asn Ile Met Asn Lys Leu Asn Ile Val Arg Thr Asn Arg Asn Glu
    130                 135                 140

Leu Phe Gln Leu Leu Thr His Val Lys Ser Thr Leu Asn Asn Ala Ser
145                 150                 155                 160

Val Ser Val Lys Cys Thr His Pro Leu Val Leu Ile His Ser Arg Ala
                165                 170                 175

Ser Pro Arg Ile Gly Asp Gln Leu Lys Glu Leu Asp Lys Ile Tyr Ser
            180                 185                 190

Pro Ser Asn His His Ile Leu Leu Ser Thr Thr Arg Phe Gln Ser Met
        195                 200                 205

His Phe Thr Asp Met Ser Ser Ser Gln Asp Leu Ser Phe Ile Tyr Arg
    210                 215                 220

Lys Pro Glu Thr Asn Tyr Tyr Ile His Pro Ile Leu Met Ala Leu Phe
225                 230                 235                 240

Gly Ile Lys Leu Pro Ala Leu Glu Asn Ala Tyr Val His Gly Asp Thr
                245                 250                 255

Tyr Ser Leu Ile Gln Gln Leu Tyr Glu Phe Arg Lys Val Lys Ser Tyr
            260                 265                 270

Asn Tyr Met Leu Leu Val Asn Arg Leu Thr Glu Asp Asn Pro Ile Val
        275                 280                 285

Ile Thr Gly Val Ser Asp Leu Ile Ser Thr Glu Ile Gln Arg Ala Asn
    290                 295                 300

Met His Thr Met Ile Arg Lys Ala Ile Met Asn Ile Arg Met Gly Ile
305                 310                 315                 320

Phe Tyr Cys Asn Asp Asp Ala Val Asp Pro His Leu Met Lys Ile
                325                 330                 335
```

```
Ile His Thr Gly Cys Ser Gln Val Met Thr Asp Glu Glu Gln Ile Leu
                340                 345                 350
Ala Ser Ile Leu Ser Ile Val Gly Phe Arg Pro Thr Leu Val Ser Val
            355                 360                 365
Ala Arg Pro Ile Asn Gly Ile Ser Tyr Asp Met Lys Leu Gln Ala Ala
        370                 375                 380
Pro Tyr Ile Val Val Asn Pro Met Lys Met Ile Thr Thr Ser Asp Ser
385                 390                 395                 400
Pro Ile Ser Ile Asn Ser Lys Asp Ile Tyr Ser Met Ala Phe Asp Gly
                405                 410                 415
Asn Ser Gly Arg Val Val Phe Ala Pro Pro Asn Ile Gly Tyr Gly Arg
            420                 425                 430
Cys Ser Gly Val Thr His Ile Asp Pro Leu Gly Thr Asn Val Met Gly
        435                 440                 445
Ser Ala Val His Ser Pro Val Ile Val Asn Gly Ala Met Met Phe Tyr
450                 455                 460
Val Glu Arg Arg Gln Asn Lys Asn Met Phe Gly Gly Glu Cys Tyr Thr
465                 470                 475                 480
Gly Phe Arg Ser Leu Ile Asp Asp Thr Pro Ile Asp Val Ser Pro Glu
            485                 490                 495
Ile Met Leu Asn Gly Ile Met Tyr Arg Leu Lys Ser Ala Val Cys Tyr
        500                 505                 510
Lys Leu Gly Asp Gln Phe Phe Asp Cys Gly Ser Ser Asp Ile Phe Leu
    515                 520                 525
Lys Gly His Tyr Thr Ile Leu Phe Thr Glu Asn Gly Pro Trp Met Tyr
530                 535                 540
Asp Pro Leu Ser Val Phe Asn Pro Gly Ala Arg Asn Ala Arg Leu Met
545                 550                 555                 560
Arg Ala Leu Lys Asn Gln Tyr Lys Lys Leu Ser Met Asp Ser Asp Asp
                565                 570                 575
Gly Phe Tyr Glu Trp Leu Asn Gly Asp Gly Ser Val Phe Ala Ala Ser
            580                 585                 590
Lys Gln Gln Met Leu Met Asn His Val Ala Asn Phe Asp Asp Asp Leu
        595                 600                 605
Leu Thr Met Glu Glu Ala Met Ser Met Ile Ser Arg His Cys Cys Ile
610                 615                 620
Leu Ile Tyr Ala Gln Asp Tyr Asp Gln Tyr Ile Ser Ala Arg His Ile
625                 630                 635                 640
Thr Glu Leu Phe

<210> SEQ ID NO 2
<211> LENGTH: 168
<212> TYPE: PRT
<213> ORGANISM: Vaccinia virus

<400> SEQUENCE: 2

Met Lys Ser Leu Asn Arg Gln Thr Val Ser Arg Phe Lys Lys Leu Ser
1               5                   10                  15
Val Pro Val Ala Ile Met Met Ile Leu Ser Thr Ile Ile Ser Gly Ile
            20                  25                  30
Gly Thr Phe Leu His Tyr Lys Glu Glu Leu Met Pro Ser Ala Cys Ala
        35                  40                  45
Asn Gly Trp Ile Gln Tyr Asp Lys His Cys Tyr Leu Asp Thr Asn Ile
    50                  55                  60
```

```
Lys Met Ser Thr Asp Asn Ala Val Tyr Gln Cys Arg Lys Leu Arg Ala
 65                  70                  75                  80

Arg Leu Pro Arg Pro Asp Thr Arg His Leu Arg Val Leu Phe Ser Ile
                 85                  90                  95

Phe Tyr Lys Asp Tyr Trp Val Ser Leu Lys Lys Thr Asn Asp Lys Trp
             100                 105                 110

Leu Asp Ile Asn Asn Asp Lys Asp Ile Asp Ile Ser Lys Leu Thr Asn
         115                 120                 125

Phe Lys Gln Leu Asn Ser Thr Thr Asp Ala Glu Ala Cys Tyr Ile Tyr
     130                 135                 140

Lys Ser Gly Lys Leu Val Lys Thr Val Cys Lys Ser Thr Gln Ser Val
145                 150                 155                 160

Leu Cys Val Lys Lys Phe Tyr Lys
                 165

<210> SEQ ID NO 3
<211> LENGTH: 94
<212> TYPE: PRT
<213> ORGANISM: Vaccinia virus

<400> SEQUENCE: 3

Met Ser Cys Tyr Thr Ala Ile Leu Lys Ser Val Gly Gly Leu Ala Leu
  1               5                  10                  15

Phe Gln Val Ala Asn Gly Ala Ile Asp Leu Cys Arg His Phe Phe Met
             20                  25                  30

Tyr Phe Cys Glu Gln Lys Leu Arg Pro Asn Ser Phe Trp Phe Val Val
         35                  40                  45

Val Arg Ala Ile Ala Ser Met Ile Met Tyr Leu Val Leu Gly Ile Ala
     50                  55                  60

Leu Leu Tyr Ile Ser Glu Gln Asp Asn Lys Lys Asn Thr Asn Asn Asp
 65                  70                  75                  80

Lys Arg Asn Glu Ser Ser Ile Asn Ser Asn Ser Ser Pro Lys
                 85                  90

<210> SEQ ID NO 4
<211> LENGTH: 644
<212> TYPE: PRT
<213> ORGANISM: Artificial Sequence
<220> FEATURE:
<223> OTHER INFORMATION: H639Y mutant of A3L gene prodcut

<400> SEQUENCE: 4

Met Glu Ala Val Val Asn Ser Asp Val Phe Leu Thr Ser Asn Ala Gly
  1               5                  10                  15

Leu Lys Ser Ser Tyr Thr Asn Gln Thr Leu Ser Leu Val Asp Glu Asp
             20                  25                  30

His Ile His Thr Ser Asp Lys Ser Leu Ser Cys Ser Val Cys Asn Ser
         35                  40                  45

Leu Ser Lys Ile Val Asp Asp Phe Ile Ser Ala Gly Ala Arg Asn
     50                  55                  60

Gln Arg Thr Lys Pro Lys Arg Ala Gly Asn Asn Gln Ser Gln Pro
 65                  70                  75                  80

Ile Lys Lys Asp Cys Met Val Ser Ile Asp Glu Val Ala Ser Thr His
                 85                  90                  95

Asp Trp Ser Thr Arg Leu Arg Asn Asp Gly Asn Ala Ile Ala Lys Tyr
             100                 105                 110

Leu Thr Thr Asn Lys Tyr Asp Thr Ser Asn Phe Thr Ile Gln Asp Met
```

```
            115                 120                 125
Leu Asn Ile Met Asn Lys Leu Asn Ile Val Arg Thr Asn Arg Asn Glu
130                 135                 140
Leu Phe Gln Leu Leu Thr His Val Lys Ser Thr Leu Asn Asn Ala Ser
145                 150                 155                 160
Val Ser Val Lys Cys Thr His Pro Leu Val Leu Ile His Ser Arg Ala
                165                 170                 175
Ser Pro Arg Ile Gly Asp Gln Leu Lys Glu Leu Asp Lys Ile Tyr Ser
                180                 185                 190
Pro Ser Asn His His Ile Leu Leu Ser Thr Thr Arg Phe Gln Ser Met
                195                 200                 205
His Phe Thr Asp Met Ser Ser Ser Gln Asp Leu Ser Phe Ile Tyr Arg
            210                 215                 220
Lys Pro Glu Thr Asn Tyr Tyr Ile His Pro Ile Leu Met Ala Leu Phe
225                 230                 235                 240
Gly Ile Lys Leu Pro Ala Leu Glu Asn Ala Tyr Val His Gly Asp Thr
                245                 250                 255
Tyr Ser Leu Ile Gln Gln Leu Tyr Glu Phe Arg Lys Val Lys Ser Tyr
                260                 265                 270
Asn Tyr Met Leu Leu Val Asn Arg Leu Thr Glu Asp Asn Pro Ile Val
            275                 280                 285
Ile Thr Gly Val Ser Asp Leu Ile Ser Thr Glu Ile Gln Arg Ala Asn
            290                 295                 300
Met His Thr Met Ile Arg Lys Ala Ile Met Asn Ile Arg Met Gly Ile
305                 310                 315                 320
Phe Tyr Cys Asn Asp Asp Ala Val Asp Pro His Leu Met Lys Ile
                325                 330                 335
Ile His Thr Gly Cys Ser Gln Val Met Thr Asp Glu Glu Gln Ile Leu
                340                 345                 350
Ala Ser Ile Leu Ser Ile Val Gly Phe Arg Pro Thr Leu Val Ser Val
            355                 360                 365
Ala Arg Pro Ile Asn Gly Ile Ser Tyr Asp Met Lys Leu Gln Ala Ala
            370                 375                 380
Pro Tyr Ile Val Val Asn Pro Met Lys Met Ile Thr Thr Ser Asp Ser
385                 390                 395                 400
Pro Ile Ser Ile Asn Ser Lys Asp Ile Tyr Ser Met Ala Phe Asp Gly
                405                 410                 415
Asn Ser Gly Arg Val Val Phe Ala Pro Pro Asn Ile Gly Tyr Gly Arg
                420                 425                 430
Cys Ser Gly Val Thr His Ile Asp Pro Leu Gly Thr Asn Val Met Gly
            435                 440                 445
Ser Ala Val His Ser Pro Val Ile Val Asn Gly Ala Met Met Phe Tyr
            450                 455                 460
Val Glu Arg Arg Gln Asn Lys Asn Met Phe Gly Gly Glu Cys Tyr Thr
465                 470                 475                 480
Gly Phe Arg Ser Leu Ile Asp Asp Thr Pro Ile Asp Val Ser Pro Glu
                485                 490                 495
Ile Met Leu Asn Gly Ile Met Tyr Arg Leu Lys Ser Ala Val Cys Tyr
                500                 505                 510
Lys Leu Gly Asp Gln Phe Phe Asp Cys Gly Ser Ser Asp Ile Phe Leu
            515                 520                 525
Lys Gly His Tyr Thr Ile Leu Phe Thr Glu Asn Gly Pro Trp Met Tyr
            530                 535                 540
```

Asp Pro Leu Ser Val Phe Asn Pro Gly Ala Arg Asn Ala Arg Leu Met
545                 550                 555                 560

Arg Ala Leu Lys Asn Gln Tyr Lys Lys Leu Ser Met Asp Ser Asp Asp
                565                 570                 575

Gly Phe Tyr Glu Trp Leu Asn Gly Asp Gly Ser Val Phe Ala Ala Ser
            580                 585                 590

Lys Gln Gln Met Leu Met Asn His Val Ala Asn Phe Asp Asp Asp Leu
        595                 600                 605

Leu Thr Met Glu Glu Ala Met Ser Met Ile Ser Arg His Cys Cys Ile
    610                 615                 620

Leu Ile Tyr Ala Gln Asp Tyr Asp Gln Tyr Ile Ser Ala Arg Tyr Ile
625                 630                 635                 640

Thr Glu Leu Phe

<210> SEQ ID NO 5
<211> LENGTH: 168
<212> TYPE: PRT
<213> ORGANISM: Artificial Sequence
<220> FEATURE:
<223> OTHER INFORMATION: D86Y mutant of A34R gene product

<400> SEQUENCE: 5

Met Lys Ser Leu Asn Arg Gln Thr Val Ser Arg Phe Lys Lys Leu Ser
1               5                   10                  15

Val Pro Val Ala Ile Met Met Ile Leu Ser Thr Ile Ile Ser Gly Ile
                20                  25                  30

Gly Thr Phe Leu His Tyr Lys Glu Glu Leu Met Pro Ser Ala Cys Ala
            35                  40                  45

Asn Gly Trp Ile Gln Tyr Asp Lys His Cys Tyr Leu Asp Thr Asn Ile
        50                  55                  60

Lys Met Ser Thr Asp Asn Ala Val Tyr Gln Cys Arg Lys Leu Arg Ala
65                  70                  75                  80

Arg Leu Pro Arg Pro Tyr Thr Arg His Leu Arg Val Leu Phe Ser Ile
                85                  90                  95

Phe Tyr Lys Asp Tyr Trp Val Ser Leu Lys Lys Thr Asn Asp Lys Trp
                100                 105                 110

Leu Asp Ile Asn Asn Asp Lys Asp Ile Asp Ile Ser Lys Leu Thr Asn
            115                 120                 125

Phe Lys Gln Leu Asn Ser Thr Thr Asp Ala Glu Ala Cys Tyr Ile Tyr
        130                 135                 140

Lys Ser Gly Lys Leu Val Lys Thr Val Cys Lys Ser Thr Gln Ser Val
145                 150                 155                 160

Leu Cys Val Lys Lys Phe Tyr Lys
                165

<210> SEQ ID NO 6
<211> LENGTH: 94
<212> TYPE: PRT
<213> ORGANISM: Artificial Sequence
<220> FEATURE:
<223> OTHER INFORMATION: K75E mutant of A9L gene product

<400> SEQUENCE: 6

Met Ser Cys Tyr Thr Ala Ile Leu Lys Ser Val Gly Gly Leu Ala Leu
1               5                   10                  15

Phe Gln Val Ala Asn Gly Ala Ile Asp Leu Cys Arg His Phe Phe Met
                20                  25                  30

```
Tyr Phe Cys Glu Gln Lys Leu Arg Pro Asn Ser Phe Trp Phe Val Val
        35                  40                  45

Val Arg Ala Ile Ala Ser Met Ile Met Tyr Leu Val Leu Gly Ile Ala
    50                  55                  60

Leu Leu Tyr Ile Ser Glu Gln Asp Asn Lys Glu Asn Thr Asn Asn Asp
65                  70                  75                  80

Lys Arg Asn Glu Ser Ser Ile Asn Ser Asn Ser Ser Pro Lys
                85                  90

<210> SEQ ID NO 7
<211> LENGTH: 1935
<212> TYPE: DNA
<213> ORGANISM: Vaccinia virus

<400> SEQUENCE: 7
atggaagccg tggtcaatag cgatgttttt ttaacatcta acgcaggact aaaatctagt      60
tatactaatc aaactctttc tttggtagat gaagatcata ttcacacttc tgataaatct     120
ttgtcttgta gtgtatgcaa ttcattatcc aaaattgtag acgatgactt tatatccgca     180
ggggctagaa atcaacgtac caaacctaaa cgtgcaggaa ataatcaatc tcaacagcct     240
atcaaaaagg attgtatggt ttccatcgac gaagtagcat ccacgcatga ttggagtacg     300
agattgagaa atgatgggaa tgcaattgct aaatatctaa ctactaacaa gtatgacaca     360
tctaacttta ctattcagga tatgcttaac attatgaata aactaaatat tgtcagaaca     420
aatagaaacg agctatttca actccttacc catgtaaaga gcacattgaa caatgctagt     480
gtttctgtga aatgtactca tcctttagta cttattcatt ctcgagctag tcctagaatc     540
ggtgaccaac tcaaagagtt agataaaata tactctccat ctaatcatca tattcttctg     600
tcgactacac gattccaatc catgcatttt accgatatgt ctagttcaca agatttgtct     660
tttatttata gaaaaccaga aactaattac tatattcatc ctattctgat ggcactattc     720
ggtattaaac ttcctgcgct cgagaacgcg tatgtacatg gagacaccta tagcctaatc     780
cagcaacttt atgaatttag aaaagtaaag tcttataatt atatgttgtt ggttaatcgt     840
cttacggagg ataatccgat agtgattaca ggtgtatcag atctaatttc cacagagatt     900
cagagagcaa acatgcatac catgattaga aaagcaatta tgaacattag aatgggaatt     960
ttttattgta acgatgatga tgcggtagat ccccatctaa tgaagattat tcatactgga    1020
tgctctcaag ttatgacaga tgaagaacag atattggctt ctattttgtc tatagttgga    1080
tttagaccta cgttggtttc tgtggctaga cctataaacg gcatcagtta cgatatgaaa    1140
cttcaggcgg caccatacat agttgttaat cctatgaaga tgatcacaac atccgacagt    1200
ccgatttcta tcaattccaa ggatatttat tctatggcat tcgatggcaa tagtggaaga    1260
gtggtgttcg ctcctcctaa cataggatat ggaagatgtt ctggagttac acacattgat    1320
ccattgggaa ctaatgtgat gggtagtgct gttcattccc ctgttatcgt taatggagca    1380
atgatgtttt atgtagaacg acgtcagaat aagaatatgt ttggtggaga atgttacacc    1440
ggctttagat ctctaataga tgatactccg attgacgtat caccagaaat catgctaaac    1500
ggtatcatgt ataggttaaa gtccgcagtt tgttacaaac tcggagacca attctttgat    1560
tgtggatcgt ctgatatctt cttgaaggga cattatacga ttctatttac agaaaatgga    1620
ccctggatgt acgatcctct ttctgttttc aatccgggag ctagaaatgc tagattgatg    1680
cgagctctca aaaaccagta caagaaatta tcaatggatt cagacgatgg tttttatgaa    1740
```

```
tggttgaatg gcgacggttc agtatttgct gcctcaaaac agcaaatgtt gatgaatcac    1800
gttgctaact tgacgacga tcttctaact atggaagaag ccatgtcgat gatttcgaga    1860
cattgttgta tcttaattta tgcacaggat tatgatcaat atattagcgc tagacatatt    1920
acagaactat tttag                                                    1935

<210> SEQ ID NO 8
<211> LENGTH: 507
<212> TYPE: DNA
<213> ORGANISM: Vaccinia virus

<400> SEQUENCE: 8
atgaaatcgc ttaatagaca aactgtaagt aggtttaaga agttgtcggt gccggtcgct     60
ataatgatga tactctcaac cattattagt ggcataggaa catttctgca ttacaaagaa    120
gaactgatgc ctagtgcttg cgccaatgga tggatacaat acgataaaca ttgttatta    180 gatactaaca ttaaaatgtc tacagataat gcggtttatc agtgtcgtaa attacgagcc    240
agattgccta gaccggatac tagacatctg agagtattgt ttagtatttt ttataaagat    300
tattgggtaa gtttaaaaaa gaccaatgat aaatggttag atattaataa tgataaagat    360
atagatatta gtaaattaac aaattttaaa caactaaaca gtcgacggga tgctgaagcg    420
tgttatatat acaagtctgg aaaactggtt aaaacagtat gtaaaagtac tcaatctgta    480
ctatgtgtta aaaaattcta caagtga                                       507

<210> SEQ ID NO 9
<211> LENGTH: 285
<212> TYPE: DNA
<213> ORGANISM: Vaccinia virus

<400> SEQUENCE: 9
atgtcatgtt atacagctat attaaaatct gtaggaggac tggcgctatt tcaagtagcc     60
aatggcgcca tagatttatg tagacatttc tttatgtatt tttgtgaaca aaagctacga    120
ccaaattcat tttggttcgt cgttgttaga gccattgcaa gcatgataat gtatttagta    180
ttaggcatag cattgctgta tatttctgaa caagataaca agaagaatac taataatgat    240
aaacgaaatg agtcgtctat aaattctaac tccagtccta agtaa                   285

<210> SEQ ID NO 10
<211> LENGTH: 1935
<212> TYPE: DNA
<213> ORGANISM: Artificial Sequence
<220> FEATURE:
<223> OTHER INFORMATION: A3L gene mutant

<400> SEQUENCE: 10
atggaagccg tggtcaatag cgatgttttt ttaacatcta acgcaggact aaaatctagt     60
tatactaatc aaactctttc tttggtagat gaagatcata ttcacacttc tgataaatct    120
ttgtcttgta gtgtatgcaa ttcattatcc aaaattgtag acgatgactt tatatccgca    180
ggggctagaa atcaacgtac caaacctaaa cgtgcaggaa ataatcaatc tcaacagcct    240
atcaaaaagg attgtatggt ttccatcgac gaagtagcat ccacgcatga ttggagtacg    300
agattgagaa atgatgggaa tgcaattgct aaatatctaa ctactaacaa gtatgacaca    360
tctaacttta ctattcagga tatgcttaac attatgaata aactaaatat tgtcagaaca    420
aatagaaacg agctatttca actccttacc catgtaaaga gcacattgaa caatgctagt    480
gtttctgtga aatgtactca tcctttagta cttattcatt ctcgagctag tcctagaatc    540
```

```
ggtgaccaac tcaaagagtt agataaaata tactctccat ctaatcatca tattcttctg      600
tcgactacac gattccaatc catgcatttt accgatatgt ctagttcaca agatttgtct      660
tttatttata gaaaaccaga aactaattac tatattcatc ctattctgat ggcactattc      720
ggtattaaac ttcctgcgct cgagaacgcg tatgtacatg gagacaccta tagcctaatc      780
cagcaacttt atgaatttag aaaagtaaag tcttataatt atatgttgtt ggttaatcgt      840
cttacggagg ataatccgat agtgattaca ggtgtatcag atctaatttc cacagagatt      900
cagagagcaa acatgcatac catgattaga aaagcaatta tgaacattag aatgggaatt      960
ttttattgta acgatgatga tgcggtagat ccccatctaa tgaagattat tcatactgga     1020
tgctctcaag ttatgacaga tgaagaacag atattggctt ctattttgtc tatagttgga     1080
tttagaccta cgttggtttc tgtggctaga cctataaacg gcatcagtta cgatatgaaa     1140
cttcaggcgg caccatacat agttgttaat cctatgaaga tgatcacaac atccgacagt     1200
ccgatttcta tcaattccaa ggatatttat tctatggcat cgatggcaa tagtggaaga      1260 gtggtgttcg ctcctcctaa cataggatat ggaagatgtt ctggagttac acacattgat     1320
ccattgggaa ctaatgtgat gggtagtgct gttcattccc ctgttatcgt taatggagca     1380
atgatgtttt atgtagaacg acgtcagaat aagaatatgt ttggtggaga atgttacacc     1440
ggctttagat ctctaataga tgatactccg attgacgtat caccagaaat catgctaaac     1500
ggtatcatgt ataggttaaa gtccgcagtt tgttacaaac tcggagacca attctttgat     1560
tgtggatcgt ctgatatctt cttgaaggga cattatacga ttctatttac agaaaatgga     1620
ccctggatgt acgatcctct ttctgttttc aatccgggag ctagaaatgc tagattgatg     1680
cgagctctca aaaccagta caagaaatta tcaatggatt cagacgatgg ttttttatgaa     1740 tggttgaatg gcgacggttc agtatttgct gcctcaaaac agcaaatgtt gatgaatcac     1800
gttgctaact ttgacgacga tcttctaact atggaagaag ccatgtcgat gatttcgaga     1860
cattgttgta tcttaatttta tgcacaggat tatgatcaat atattagcgc tagatatatt     1920
acagaactat tttag                                                       1935

<210> SEQ ID NO 11
<211> LENGTH: 507
<212> TYPE: DNA
<213> ORGANISM: Artificial Sequence
<220> FEATURE:
<223> OTHER INFORMATION: A34R gene mutant

<400> SEQUENCE: 11
atgaaatcgc ttaatagaca aactgtaagt aggtttaaga agttgtcggt gccggtcgct       60
ataatgatga tactctcaac cattattagt ggcataggaa catttctgca ttacaaagaa      120
gaactgatgc ctagtgcttg cgccaatgga tggatacaat acgataaaca ttgttatttta     180 gatactaaca ttaaaatgtc tacagataat gcggtttatc agtgtcgtaa attacgagcc     240
agattgccta gaccgtatac tagacatctg agagtattgt ttagtatttt ttataaagat     300
tattgggtaa gtttaaaaaa gaccaatgat aaatggttag atattaataa tgataaagat     360
atagatatta gtaaattaac aaattttaaa caactaaaca gtacgacgga tgctgaagcg     420
tgttatatat acaagtctgg aaaactggtt aaaacagtat gtaaaagtac tcaatctgta     480
ctatgtgtta aaaaattcta caagtga                                          507

<210> SEQ ID NO 12
```

```
<211> LENGTH: 285
<212> TYPE: DNA
<213> ORGANISM: Artificial Sequence
<220> FEATURE:
<223> OTHER INFORMATION: A9L gene mutant

<400> SEQUENCE: 12
atgtcatgtt atacagctat attaaaatct gtaggaggac tggcgctatt tcaagtagcc      60
aatggcgcca tagatttatg tagacatttc tttatgtatt tttgtgaaca aaagctacga     120
ccaaattcat tttggttcgt cgttgttaga gccattgcaa gcatgataat gtatttagta     180
ttaggcatag cattgctgta tatttctgaa caagataaca aggagaatac taataatgat     240
aaacgaaatg agtcgtctat aaattctaac tccagtccta agtaa                     285

<210> SEQ ID NO 13
<211> LENGTH: 24
<212> TYPE: DNA
<213> ORGANISM: Artificial Sequence
<220> FEATURE:
<223> OTHER INFORMATION: primer for qPCR

<400> SEQUENCE: 13
cgttttgcat catacctcca tctt                                             24

<210> SEQ ID NO 14
<211> LENGTH: 30
<212> TYPE: DNA
<213> ORGANISM: Artificial Sequence
<220> FEATURE:
<223> OTHER INFORMATION: probe for qPCR
<220> FEATURE:
<221> NAME/KEY: misc_feature
<222> LOCATION: (1)..(1)
<223> OTHER INFORMATION: modified with 6FAM
<220> FEATURE:
<221> NAME/KEY: misc_feature
<222> LOCATION: (30)..(30)
<223> OTHER INFORMATION: modified with BHQ1

<400> SEQUENCE: 14
aggcataaac gattgctgct gttcctctgt                                       30

<210> SEQ ID NO 15
<211> LENGTH: 18
<212> TYPE: DNA
<213> ORGANISM: Artificial Sequence
<220> FEATURE:
<223> OTHER INFORMATION: primer for qPCR

<400> SEQUENCE: 15
gcgggtgctg gagtgctt                                                    18

<210> SEQ ID NO 16
<211> LENGTH: 22
<212> TYPE: DNA
<213> ORGANISM: Artificial Sequence
<220> FEATURE:
<223> OTHER INFORMATION: primer for qPCR

<400> SEQUENCE: 16
tgactccggt ccttctaaca ca                                               22

<210> SEQ ID NO 17
<211> LENGTH: 19
<212> TYPE: DNA
<213> ORGANISM: Artificial Sequence
```

```
<220> FEATURE:
<223> OTHER INFORMATION: probe for qPCR
<220> FEATURE:
<221> NAME/KEY: misc_feature
<222> LOCATION: (1)..(1)
<223> OTHER INFORMATION: modified with YAK
<220> FEATURE:
<221> NAME/KEY: misc_feature
<222> LOCATION: (19)..(19)
<223> OTHER INFORMATION: modified with BHQ1

<400> SEQUENCE: 17
cccggtggtc ccgctgtgc                                                19

<210> SEQ ID NO 18
<211> LENGTH: 21
<212> TYPE: DNA
<213> ORGANISM: Artificial Sequence
<220> FEATURE:
<223> OTHER INFORMATION: primer for qPCR

<400> SEQUENCE: 18
tcacggcaac tggtttaatg g                                             21

<210> SEQ ID NO 19
<211> LENGTH: 20
<212> TYPE: DNA
<213> ORGANISM: Artificial Sequence
<220> FEATURE:
<223> OTHER INFORMATION: amplification primer a91f

<400> SEQUENCE: 19
gcaaacgcga taaggatacg                                               20

<210> SEQ ID NO 20
<211> LENGTH: 20
<212> TYPE: DNA
<213> ORGANISM: Artificial Sequence
<220> FEATURE:
<223> OTHER INFORMATION: Amplification primer a91r

<400> SEQUENCE: 20
aagcggatgc agaatagacg                                               20

<210> SEQ ID NO 21
<211> LENGTH: 21
<212> TYPE: DNA
<213> ORGANISM: Artificial Sequence
<220> FEATURE:
<223> OTHER INFORMATION: amplification primer a34rf

<400> SEQUENCE: 21
gcggaatcat caacactacc c                                             21

<210> SEQ ID NO 22
<211> LENGTH: 25
<212> TYPE: DNA
<213> ORGANISM: Artificial Sequence
<220> FEATURE:
<223> OTHER INFORMATION: amplification primer a34rr

<400> SEQUENCE: 22
taataacaaa cgcggcgtcc atggc                                         25

<210> SEQ ID NO 23
<211> LENGTH: 20
<212> TYPE: DNA
```

```
<213> ORGANISM: Artificial Sequence
<220> FEATURE:
<223> OTHER INFORMATION: amplification primer a3lf

<400> SEQUENCE: 23
gcagaagaac accgcttagg                                               20

<210> SEQ ID NO 24
<211> LENGTH: 20
<212> TYPE: DNA
<213> ORGANISM: Artificial Sequence
<220> FEATURE:
<223> OTHER INFORMATION: amplification primer a3lr

<400> SEQUENCE: 24
atggaagccg tggtcaatag                                               20

<210> SEQ ID NO 25
<211> LENGTH: 18
<212> TYPE: DNA
<213> ORGANISM: Artificial Sequence
<220> FEATURE:
<223> OTHER INFORMATION: amplification primer a3lf2

<400> SEQUENCE: 25
tgagagctcg catcaatc                                                 18

<210> SEQ ID NO 26
<211> LENGTH: 21
<212> TYPE: DNA
<213> ORGANISM: Artificial Sequence
<220> FEATURE:
<223> OTHER INFORMATION: amplification primer a3lf3

<400> SEQUENCE: 26
atcggactgt cggatgttgt g                                             21

<210> SEQ ID NO 27
<211> LENGTH: 20
<212> TYPE: DNA
<213> ORGANISM: Artificial Sequence
<220> FEATURE:
<223> OTHER INFORMATION: amplification primer a3lr3

<400> SEQUENCE: 27
ctagaatcgg tgaccaactc                                               20
```